(12) United States Patent
Crooke et al.

(10) Patent No.: US 6,846,667 B1
(45) Date of Patent: Jan. 25, 2005

(54) VIRULENCE GENES AND PROTEINS, AND THEIR USE

(75) Inventors: Helen Rachel Crooke, London (GB); Enda Elizabeth Clarke, London (GB); Paul Howard Everest, London (GB); Gordon Dougan, London (GB); David William Holden, London (GB); Jacqueline Elizabeth Shea, London (GB); Robert Graham Feldman, London (GB)

(73) Assignee: Microscience, Ltd. (GB)

( * ) Notice: Subject to any disclaimer, the term of this patent is extended or adjusted under 35 U.S.C. 154(b) by 0 days.

(21) Appl. No.: 09/830,807

(22) PCT Filed: Nov. 9, 1999

(86) PCT No.: PCT/GB99/03721

§ 371 (c)(1), (2), (4) Date: Jul. 16, 2001

(87) PCT Pub. No.: WO00/28038

PCT Pub. Date: May 18, 2000

(30) Foreign Application Priority Data

| Nov. 9, 1998 | (GB) | 9824569 |
| Nov. 9, 1998 | (GB) | 9824570 |
| Dec. 17, 1998 | (GB) | 9827814 |
| Dec. 17, 1998 | (GB) | 9827815 |
| Dec. 17, 1998 | (GB) | 9827816 |
| Dec. 17, 1998 | (GB) | 9827818 |
| Jan. 13, 1999 | (GB) | 9900708 |
| Jan. 13, 1999 | (GB) | 9900710 |
| Jan. 13, 1999 | (GB) | 9900711 |
| Jan. 28, 1999 | (GB) | 9901915 |

(51) Int. Cl.[7] .................... C12N 1/00; C12N 13/00; C12N 9/00; C12N 9/10; C12N 1/20

(52) U.S. Cl. ............... 435/244; 424/1.69; 435/7.32; 435/41; 435/68.1; 435/69.1; 435/69.2; 435/69.7; 435/69.8; 435/70.2; 435/71.2; 435/91.1; 435/91.4; 435/173.8; 435/183; 435/193; 435/243; 435/252.3; 436/501; 436/815; 530/300; 530/324; 530/333; 530/350; 930/10; 930/200; 930/300; 930/310

(58) Field of Search ............... 424/1.69; 435/7.32, 435/68.1, 69.1, 69.7, 69.8, 70.2, 71.2, 91.1, 91.2, 91.4, 91.41, 91.42, 91.45, 320.1, 480; 530/300, 324–330, 333, 350; 930/10, 200, 300, 310

(56) References Cited

PUBLICATIONS

Database SPTREMBL [Online], Accession No. O69415, Aug. 1, 1998, "tatB protein (mttA2)" (XP002133195).

Database SWISSPROT [Online], Accession No. P27857, Jul. 15, 1998, "tatC protein (mttB)" (XP002133196).

Database Genbank [Online], Accession No. AJ005830, Mar. 29, 1999, Sargent: "E. coli tatABCD operon" (XP002133197).

Vann, W.F. et al. (1997) "Purification and characterization of the *Escherichia coli* K1 neuB gene product N–acetylneuraminic acid synthase" *Glycobiology* 7(5):697–701.

Boyd, E.F. and D.L:. Hartl (Mar. 1998) "Chromosomal regions specific to pathogenic isolates of *Escherichia coli* have a phylogenetically clustered distribution" *J. Bacteriol.* 180(5):1159–1165.

Weiner, J.H. et al. (Apr. 1998) "A novel and ubiquitous system for membrane targeting and secretion of cofactor- -containing proteins" *Cell* 93:93–101.

Bogsch, E.G. et al. (Jul. 1998) "An essential component of a novel bacterial protein export system with homologues in plastids and mitochondria" *J. Biol. Chem.* 273(29):18003–19006.

Cieslewicz, M. and E. Vimr (Jun. 1996) "Thermoregulation of kpsF, the First Region 1 gene . . . *E. coli* K1" *J. Bacteriology* 178(11):3212–3220.

Sargent, F. et al. (Jul. 1998) "Overlapping functions of components of a bacterial Sec–independent protein export pathway" *J. EMBO* 17(13):3640–3650.

Database SPTREMBL [Online], Accession No. O65938, Aug. 1, 1998, "tatA protein (mttA1)" (XP002133194).

*Primary Examiner*—Lynette R. F. Smith
*Assistant Examiner*—J. Hines
(74) *Attorney, Agent, or Firm*—Saliwanchik, Lloyd & Saliwanchik

(57) ABSTRACT

The present invention is based on the identification of a series of virulence genes in *E. coli* K1, the products of which may be implicated in the pathogenicity of the organisms. The identification of the genes allows them, or their expressed products, to be used in a number of ways to treat infection.

4 Claims, No Drawings

VIRULENCE GENES AND PROTEINS, AND THEIR USE

FIELD OF THE INVENTION

This invention relates to the identification of virulence genes and proteins, and their use. More particularly, it relates to their use in therapy and in screening for drugs.

BACKGROUND TO THE INVENTION

*E. coli* is a member of the *Enterobacteriaceae*, or enteric bacteria, which are Gram-negative microorganisms that populate the intestinal tracts of animals. Other members of this bacterial family include *Enterobacter, Klebsielia, Salmonella, Shigella* and *Yersinia*. Although *E. coli* is found normally in the human gastrointestinal tract, it has been implicated in human disease, including septicaemia, meningitis, urinary tract infection, wound infection, abscess formation, peritonitis and cholangitis.

The disease states caused by *E. coli* are dependent upon certain virulence determinants. For example, *E. coli* has been implicated in neonatal meningitis and a major determinant of virulence has been identified as the K1 antigen, which is a homopolymer of sialic acid. The K1 antigen may have a role in avoiding the host's immunological system and preventing phagocytosis.

SUMMARY OF THE INVENTION

The present invention is based on the identification of a series of virulence genes in *E. coli* K1, and also related organisms the products of which may be implicated in the pathogenicity of the organism.

According to one aspect of the present invention, a peptide is encoded by an operon including any of the genes identified herein as mdoG, creC, recg, yggN, tatA, tatB, tatC, tatE, eck1, iroD, iroC, iroE, mtd2 and ms1 to 16, from *E. coli* K1, or a homologue thereof in a Gram-negative bacterium, or a functional fragment thereof. Such a peptide is suitable for therapeutic use, e.g. when isolated.

The term "functional fragments" is used herein to define a part of the gene or peptide which retains similar therapeutic utility as the whole gene or peptide. For example, a functional fragment of the peptide may be used as an antigenic determinant, useful in a vaccine or in the production of antibodies. A gene fragment may be used to encode the active peptide. Alternatively, the gene fragment may have utility in gene therapy, targetting the wild-type gene in vivo to exert a therapeutic effect.

A peptide according to the present invention may comprise any of the amino acid sequences identified herein as SEQ ID NOS. 2, 5, 7, 9, 11, 12, 13, 14, 16, 23, 24, 25, 26, 28, 31, 29, 32 and 35–48.

The identification of these peptides as virulence determinants allows them to be used in a number of ways in the treatment of infection. For example, a host may be transformed to express a peptide according to the invention or modified to disrupt expression of the gene encoding the peptide. A vaccine may also comprise a peptide according to the invention, or the means for its expression, for the treatment of infection. In addition, a vaccine may comprise a microorganism having a virulence gene deletion, wherein the gene encodes a peptide according to the invention.

According to another aspect of the invention, the peptides or genes may be used for screening potential antimicrobial drugs or for the detection of virulence.

A further aspect of this invention is the use of any of the products identified herein, for the treatment or prevention of a condition associated with infection by a Gram-negative bacterium, in particular by *E. coli*.

DESCRIPTION OF THE INVENTION

The present invention has made use of signature-tagged mutagenesis (STM) (Hensel et al., Science, 1995;269:400–403) to screen *E. coli* K1 strain RS228 (Pluschke et al, Infection and Immunity 39:599–608) mini-Tn5 mutant bank for attenuated mutants, to identify virulence genes (and virulence determinants) of *E. coli*.

Although *E. coli* K1 was used as the microorganism to identify the virulence genes, corresponding genes in other enteric bacteria are considered to be within the scope of the present invention. For example, corresponding genes or encoded proteins may be found, based on sequence homology, in *Enterobacter, Klebsiella* and other genera implicated in human intestinal disease, including *Salmonella, Shigella* and *Yersinia*.

The term "virulence determinant" is used herein to define a product, e.g. a peptide or protein that may have a role in the maintenance of pathogenic bacteria. In particular, a virulence determinant is a bacterial protein or peptide that is implicated in the pathogenicity of the infectious or disease-causing microorganism.

A gene that encodes a virulence determinant may be termed a "virulence gene". Disruption of a virulence gene by way of mutation, deletion or insertion, will result in a reduced level of survival of the bacteria in a host, or a general reduction in the pathogenicity of the microorganism.

Signature-tagged mutagenesis has proved a very useful technique for identifying virulence genes, and their products. The technique relies on the ability of transposons to insert randomly into the genome of a microorganism, under permissive conditions. The transposons are individually marked for easy identification, and then introduced separately into a microorganism, resulting in disruption of the genome. Mutated microorganisms with reduced virulence are then detected by negative selection and the genes where insertional inactivation has occurred are identified and characterised.

A first stage in the STM process is the preparation of suitable transposons or transposon-like elements. A library of different transposons are prepared, each being incorporated into a vector or plasmid to facilitate transfer into the microorganism. The preparation of vectors with suitable transposons will be apparent to a skilled person in the art and is further disclosed in WO-A-96/17951. For the Gram-negative bacteria, e.g. *E. coli*, suitable transposons include Tn5 and Tn10. Having prepared the transposons, mutagenesis of a bacterial strain is then carried out to create a library of individually mutated bacteria.

Pools of the mutated microorganisms are then introduced into a suitable host. After a suitable length of time, the microorganisms are recovered from the host and those microorganisms that have survived in the host are identified, thereby also identifying the mutated strains that failed to survive, i.e. avirulent strains. Corresponding avirulent strains in a stored library are then used to identify the genes where insertional inactivation occurred. Usually, the site of transposon insertion is identified by isolating the DNA flanking the transposons insertion site, and this permits characterisation of the genes implicated in virulence.

Once an avirulent microorganism has been identified, it is possible to determine more fully the potential role of the mutated gene in virulence, by infecting a suitable host animal with a lethal dose of the mutant. The survival time of the infected animal is compared with that of a control infected with the wild-type strain, and those animals surviving for longer periods than the control may be said to be infected with microorganisms having mutated virulence genes.

Alternatively, the potential role in virulence can be investigated by infecting an animal host with a mixture of the wild-type and mutant bacteria. After a suitable period of time, bacteria are harvested from organs of the host animal and the ratio of wild-type and mutant bacteria determined. This ratio is divided by the ratio of mutant to wild-type bacteria in the inoculum, to determine the competitive index (CI). Mutants which have a competitive index of less than 1 may be said to be avirulent.

It is possible that the gene which is inactivated by the insertion of the transposon may not be a true virulence gene, but may be having a polar effect on a downstream (virulence) gene. This can be determined by further experimentation, placing non-polar mutations in more defined regions of the gene, or mutating other adjacent genes, and establishing whether or not the mutant is avirulent.

Having characterised a virulence gene in E. coli, it is possible to use the gene sequence to establish homologies in other microorganisms. In this way it is possible to determine whether other microorganisms have similar virulence determinants. Sequence homologies may be established by searching in existing databases, e.g. EMBL or Genbank.

Virulence genes are often clustered together in distinct chromosomal regions called pathogenicity islands. Pathogenicity islands can be recognised as they are usually flanked by repeat sequences, insertion elements or tRNA genes. Also the G+C content is normally different from the remainder of the chromosome, suggesting that they were acquired by horizontal transmission from another organism. For example the G+C content of the E. coli K12 genome is 52%. Any pathogenicity islands found in E. coli strains are likely to have a G+C content that varies from this average.

The identified virulence genes are likely to be useful both in generating attenuated vaccine strains and as a target for antimicrobials. The same may be true for homologues in Gram-negative bacteria in general.

For the purpose of this invention, the appropriate degree of homology is typically at least 30%, preferably at least 50%, 60% or 70%, and more preferably at least 80% or 90% (at the amino acid or nucleotide level).

Proteins according to the invention may be purified and isolated by methods known in the art. In particular, having identified the gene sequence, it will be possible to use recombinant techniques to express the genes in a suitable host. Active fragments and homologues can be identified and may be useful in therapy. For example, the proteins or their active fragments may be used as antigenic determinants in a vaccine, to selicit an immune response. They may also be used in the preparation of antibodies, for passive immunisation, or diagnostic applications. Suitable antibodies include monoclonal antibodies, or fragments thereof, including single chain fv fragments. Methods for the preparation of antibodies will be apparent to those skilled in the art.

The preparation of vaccines based on attenuated microorganisms is known to those skilled in the art. Vaccine compositions can be formulated with suitable carriers or adjuvants, e.g. alum, as necessary or desired, and used in therapy, to provide effective immunisation against E. coli or other Gram-negative bacteria. The preparation of vaccine formulations will be apparent to the skilled person.

More generally, and as is well known to those skilled in the art, a suitable amount of an active component of the invention can be selected, for therapeutic use, as can suitable carriers or excipients, and routes of administration. These factors will be chosen or determined according to known criteria such as the nature/severity of the condition to be treated, the type or health of the subject etc.

The following Examples illustrate the invention. For the Examples, STM was used to screen an E. coli K1 mini-Tn5 mutant bank for attenuated mutants, using a mouse model of systemic infection. The basic procedure followed that disclosed in Hensel et al, supra. E. coli K1 containing a mini-Tn5 insertion within a virulence gene was not recovered from mice inoculated with a mixed population of mutants, and is therefore likely to be attenuated.

The DNA region flanking either side of the mini-Tn5 insertion was cloned by inverse PCR or by rescue of a kanamycin-resistance marker. In the latter case, chromosomal DNA from the STM-derived mutant was digested with restriction enzymes, ligated into the plasmid pUC19, and kanamycin-resistant 14 clones selected after transformation into competent E. coli K12 cells. Subsequent cloning and sequencing was then performed and the gene sequences compared using sequences in publicly available sequence databases (EMBL) to help characterise the putative gene products.

EXAMPLE 1

In a first mutant, two fragments of cloned DNA were sequenced. The nucleotide sequences are shown as SEQ ID NO. 1 and SEQ ID NO. 3 and a translated region of the DNA from SEQ ID NO. 1 is shown as SEQ ID NO. 2. SEQ ID NO. 1 shows 99.8% identity to the mdoGH region from E. coli K12 (EMBL database accession number AE000206) from nucleotides 2577 to 6908. This DNA fragment encodes the 5'-part of the ymdD gene, the entire mdoG gene and the 5'-part of the mdoH gene. The product of the mdoG gene is of unknown function, but is believed to be involved in the biosynthesis of membrane-derived oligosaccharides.

SEQ ID NO. 3 shows 98.3% identity to the 3'-part of the mdoH gene and downstream gene sequences from E. coli K12 (nucleotides 7187 to 7760). SEQ ID NO. 2 shows 99.6% identity to the mdoG protein from E. coli K12 (Swiss Prot accession number P33136) at amino acid 1 to 511.

The nov I gene was tested for attenuation of virulence, using mixed infections, in a murine model of systemic infection (Achtman et al., Infection and Immunity, 1983; Vol. 39:315–335), and shown to be attenuated with a competitive index (CI) of 0.38. This confirms that the attenuation of the original transposon mutant is likely to be due to the disruption of the mdoG gene.

Polar and a non-polar deletion mutants of mdoG were constructed. The mdoG gene and flanking regions were amplified by PCR with oligonucleotides 5'-TGCTCTAGAGCCATTACTCAGAATGGG-3' (SEQ ID NO. 49) and 5'-CGCGAGCTCGACGACTGAATG-ATCCC3' (SEQ ID NO. 50). The product was cloned into pUC19. A PCR product containing 5'- and 3'-terminal fragments of mdoG and the entire pUC19 sequence was then amplified by inverse PCR with the oligonucleotides 5'-TCCCCCGGGTACTGCAGCACTCAACC-3' (SEQ ID NO. 51) and 5'-GATCCCGGGACCACTGAAATG-CGTGC-3' (SEQ ID NO. 52). A non-polar kanamycin resistance cassette (apht) was inserted in both orientations between the mdoG sequences to give a polar and a non-polar construct The mdoG::aphTfusions were then transferred to the suicide vector pCDV442. The chromosomal copy of the mdoG was mutated by allelic transfer after conjugation of the pCDV442 constructs into wild type E. coli K1.

The constructed mutants were tested for attenuation of virulence In a murine model of systemic infection (Achtman et al., supra). Both the polar and the non-polar constructs were attenuated in virulence, with competitive indices of 0.37 and 0.35, respectively (mean Cl from three mice each). This confirms that the attenuation of the original transposon mutant is likely to be due to the disruption of the mdoG gene.

EXAMPLE 2

A second mutant was identified with a virulence gene having the nucleotide sequence shown in SEQ ID NO. 4 and the translated amino acid sequence shown as SEQ ID NO. 5. The mini-Tn5 transposon inserted at nucleotide 581 (SEQ ID NO. 4) and at amino acid 187 (SEQ ID NO. 5).

These sequences show 97.9% identity to the creC gene of E. coli K12 (EMBL and Genbank accession numbers M13608, AE000510 and U14003).

The creC protein from E. coli K12 belongs to the protein family of histidine kinases as well as to a protein family consisting of proteins containing a signal domain.

The novel gene was tested for attenuation of virulence (Achtman et al, supra.), and shown to be attenuated with a competitive index of 0.09.

As the E. coli K12 creC gene is transcribed as part of an operon with the creD gene, it is possible that this attenuation is due to a polar effect on a presumed E. coli K1 creD gene.

EXAMPLE 3

A third mutant had a nucleotide sequence shown as SEQ ID NO. 6 immediately following the mini-Tn5. A translation of this sequence is shown as SEQ ID NO. 7.

The nucleotide sequence shows 93.7% Identity to the recG gene of E. coli K12, at nucleotides 5–146 (EMBL and Genbank accession numbers P24230 and M64367). This demonstrates that the disrupted gene is at least partially identical to the recG gene of E. coli K12. The recG gene of E. coli K12 encodes a 76.4 kD protein which functions as ATP-dependent DNA helicase, and plays a critical role in DNA repair.

In tests for attenuation, the competitive index was shown to be 0.48. The recG gene is transcribed as the terminal gene of an operon, and it is therefore unlikely that this attenuation is due to a polar effect on another E. coli K1 gene.

EXAMPLE 4

A fourth mutant had a transposon inserted within the nucleotide sequence shown as SEQ ID NO. 8, with a translation product shown as SEQ ID NO. 9.

The mini-Tn5 transposon inserted at nucleotide 359 and amino acid 80.

These sequences show 98.5% sequence identity to the yggN gene of E. coli K12 (EMBL accession number AE000378) at nucleotides 339–1054, and 99.6% identity at the amino acid level.

Although the sequence of the yggN gene is known, the function of its encoded protein has not yet been determined.

The novel gene was tested for attenuation of virulence, and shown to be attenuated with a competitive index of 0.43.

EXAMPLE 5

Several mutants were also found with a transposon insertion within the same region. Cloning and sequencing the region revealed a nucleotide sequence shown as SEQ ID NO. 10. This sequence has homology with the tatABCD operon of E. coli K12 (EMBL and Genbank accession numbers AJ005830, AE000459 and AE000167). This operon encodes proteins of predicted mass 9.6 kD, 18.4 kD, 28.9 kD and 29.5 kD, which function as components of a Sec-independent protein export pathway. The pathway permits translocation of fully folded proteins to the periplasm through a gated pore, after the attachment of co-factors in the cytoplasm.

Translation of the nucleotide sequence revealed a protein corresponding to tatA (SEQ ID NO. 11), a sequence corresponding to tatB (SEQ ID NO. 12), a sequence corresponding to tatC (SEQ ID NO. 13) and a sequence corresponding to tatD (SEQ ID NO. 14).

The mini-Tn5 transposons in the mutants identified by STM are located at nucleotides 1429 and 2226 of SEQ ID NO. 10. These transposon insertions disrupt the tatB protein sequence at amino acid 50 and the tatC protein sequence at amino acid 143.

The tatB and tatC genes were tested for attenuation of virulence and were shown to be attenuated with competitive indices of 0.0012 and 0.0039, respectively. These genes were also attenuated in virulence when tested in single infections in the same model of systemic infection.

EXAMPLE 6

A further mutant was insertionally inactivated within a region corresponding to the tatE gene of E. coli K12, shown as SEQ ID NO. 15. A translation of the sequence as shown as SEQ ID NO. 16. The tatE gene shows 98% identity to that of the E. coli K12 gene (accession number AE000167) at nucleotides 6719–7306.

To establish whether the tatA, tatD and tatE genes are required for virulence, non-polar deletion mutations were constructed in each. The regions of DNA flanking either side of the tatA, tatD and tatE genes were amplified with the following primers:

tatA
5'-TCG TCT AGA GAT GAT GGT GAT GGA GCG-3' (SEQ ID NO. 53)
5'-GAA CTG CAG CCA AAT ACT GAT ACC ACC C-3' (SEQ ID NO. 54)
5'-GAA CTG CAG GCT AAA ACA GAA GAC GCG-3' (SEQ ID NO. 55)
5'-CAT GCA TGC ACT CCA TAT GAC MC CGC-3' (SEQ ID NO. 56)
Primers SEQ ID NO. 53 and SEQ ID NO. 54 were used to amplify DNA sequences upstream of tatA, Primers SEQ ID NO. 55 and SEQ ID NO. 56 were used to amplify DNA sequences downstream of tatA.

tatD
5'-TCG TCT AGA ATG AAG CTG CGC ATG AGG-3' (SEQ ID NO. 57)
5'-CAA CTG CAGTCG CAA ATT GCG AAC TGG-3' (SEQ ID NO. 58)
5'-CAA CTG CAG ACC GCA ACT TTT CGA CGC-3' (SEQ ID NO. 59)
5'-CAT GCA TGC CAG TGA GCC ATT GTT CCC-3' (SEQ ID NO. 60)
Primers SEQ ID NO. 57 and SEQ ID NO. 58 were used to amplify DNA sequences upstream of tatD, Primers SEQ ID NO. 59 and SEQ ID NO. 60 were used to amplify DNA sequences downstream of tatD.

tatE

5'-TGC TCT AGA TAC GAC TCT GAC AGG AGG-3' (SEQ ID NO. 61)

5'-TCA GAT ATC AAC TAC CAG CAG TTT GGG-3' (SEQ ID NO. 62)

5'-TCA GAT ATC CAT AAA GAG TGA CGT GGC-3' (SEQ ID NO. 63)

5'-TGC TCT AGA AAA CGT GGC AAC AGA GCG-3' (SEQ ID NO. 64)

Primers SEQ ID NO. 61 and SEQ ID NO. 62 were used to amplify DNA sequences upstream of tat, Primers SEQ ID NO. 63 and SEQ ID NO. 64 were used to amplify DNA sequences downstream of tatE.

After cloning these flanking DNA fragments into pUC19, a non-polar aphT kanamycin resistance cassette (Galan et al, J. Bacteriol, 1992;174:4338–4349) was inserted between the flanking DNA fragments to replace the tatA, tatD and tatE genes. These DNA fragments were then transferred to the suicide vector pCVD442 (Blomfield et. at, Mol. Micro., 1991;5:1447–1457). The chromosomal copies of the E. coli K1 tatA, tatD and tatE genes were then mutated by allelic transfer after conjugation of the pCVD442 constructs in to wild type E. coli K1.

Disruptions of the tatA, latD and tatE genes have been tested for attenuation of virulence (Achtman et al., supra).

None of the genes was attenuated when deleted in isolation. The genes may still play a role in virulence, and to test this, mutants were prepared with deletions in both tatA and tatE genes. The double mutant was tested for attenuation in virulence using mixed infections with the wild-type strain and shown to be attenuated with a competitive index of 0.0017. It seems therefore that the tatA, tatD and tatE genes may be used in combination to create avirulent microorganisms.

Given the similarity of the E. coli K1 tatABCD genes to predicted tatABCD genes present in the S. typhimurium genome and Neisseria meningitidis genome it seemed likely that the tat system may also be required for virulence in these, and other, organisms. A deletion in the S. typhimurium tatC gene (SEQ ID NO. 17) was constructed by amplifying the DNA flanking either side of the tatC gene with the following primers:

5'-TGC TCT AGA AGG CGT TGT CGA TCC TG-3' (SEQ ID NO. 65)

5'-GAA CTG CAG GAA AAG GCC GAG CAG ACT G-3' (SEQ ID NO. 66)

5'-GAA CTG CAG TAC AGC CAT GTT TAC GGT-3' (SEQ ID NO. 67)

5'-CAT GCA TGC GGT GTA CGA CAG TTT GCG-3' (SEQ ID NO. 68)

Primers SEQ ID NO. 65 and SEQ ID NO. 66 were used to amplify DNA sequences downstream of the S. typhimurium tatC gene, Primers SEQ ID NO. 67 and SEQ ID NO. 68 were used to amplify DNA sequences upstream of the S. typhimurium tatC gene.

The encoded amino acid sequences for two regions of the tatC gone are shown as SEQ ID NO. 18 and SEQ ID NO. 19.

After cloning these flanking DNA fragments into pUC19, a non-polar kanamycin resistance cassette (aphT) was inserted between the flanking DNA fragments to replace the S. typhimurium tatC gene. This DNA fragment was then transferred to the suicide vector pCVD442. The chromosomal copy of the S. typhimurium tatC gene was then mutated by allelic transfer after conjugation of the pCVD442 construct into wild type S. typhimurium strains TML and SL1344.

The disrupted S. typhimurium tatC gene was tested for attenuation of virulence, using mixed and single infections in a murine model of systemic infection. For mixed infections. 6–7 week old balbC mice were inoculated intraperitoneally with $10^4$ bacterial cells. Competitive indices were calculated after comparing the numbers of mutant and wild-type bacteria present in spleens after 3 days. For single infections, mice were inoculated either intraperitoneally or orally with varying doses and mouse survival monitored for 17 days. The strains were attenuated in virulence, the competitive indices of the SL1344 tatC and TML tatC deletion strains being 0.078 and 0.098, respectively.

In single infections, mouse survival was extended compared to the wild-type controls.

Sequence homology was also demonstrated with the tat sequence from Neisseria meningitidis. The gene sequence from N. meningitidis is shown as SEQ ID NO. 20 and the encoded amino acid sequence for tatC is shown as SEQ ID NO. 21.

To test for virulence, a deletion mutant was created using the following primers:

5'-TGCTCTAGACACATCATGGGCACACC-3' (SEQ ID NO. 69)

5'-GAACTGCAGAACCGTCCACATCAGGCG3' (SEQ ID NO. 70)

5'-GAACTGCAGACCCTGCTTGCCATTCCG-3' (SEQ ID NO. 71)

5'-GAACTGCAGACCCTGCTTGCCATTCCG-3' (SEQ ID NO. 72)

Cloning of the DNA fragments and the aphT kanamycin resistance cassette into pUC19 followed the procedure outlined above for S. typhimurium. The chromosomal copy of the N. meningitidis tatC gene was mutated by transformation of the pUC19-based constructs into wild-type N. meningitidis cells.

Southern analysis of the resulting transformants indicated that all the transformants were merodiploids and contained both the wild-type and mutated copies of the tatC gene. This indicates that there is some selection against the isolation of mutants in which the tatC gene has been deleted.

Further studies on polar and non-polar constructs showed that transformants did not grow on selective media. This suggests that the N. meningitidis tatC gene is essential for the in vitro growth of this organism.

EXAMPLE 7

A further mutant was identified with a transposon insertion within a nucleotide sequence identified herein as SEQ ID NO. 22, at nucleotide 3981. The sequence defined herein as eck1, shows sequence homology to several Group 1 glycosyltransferases from a number of bacteria. Sequence homology was also shown to the gnd gene of E. coli K12 (at nucleotides 41974604 of SEQ ID NO. 22).

The translation of the E. coli eck1 gene is shown as SEQ ID NO. 26. The gene has been tested for attenuation of virulence, as described above, and is shown to be attenuated with a competitive index of 0.025.

Several open reading frames (ORF) were also identified from the DNA sequence (SEQ ID NO. 22). The first of these is defined herein as MS1 and a translation product shown as SEQ ID NO. 25. The amino acid sequence is shown to have 50.3% identity to a putative glycosyl transferase from E. coli serotype 0111 (TrEMBL database accession number MD46732). The amino acid sequence also shows homology with the eck1 protein from E. coli K1 and also the TrsE protein from Yersinia entercolitica (TrEMBL database accession number 056917).

A second open reading frame identified herein as MS2 had the gene sequence shown as SEQ ID NO. 24. This shows sequence homology to the putative glycosyl transferase TrsC from *Yersinia entercolitica* (TrRMBL database accession number Q56915), and also the glycosyl transferase WbnA from *E. coli* serotype 0113 (TrEMBL database accession number AAD50485).

A third open reading frame encodes a product identified herein as MS3 (SEQ ID NO. 23). The amino acid sequence shows 30.2% identity to a rhamnosyltransferase from *Streptoccus mutans*.

The gene sequence shown as SEQ ID NO. 22 may be at least part of a pathogenicity island, with multiple virulence genes being positioned in a cluster on the microorganism's genome.

EXAMPLE 8

A further mutant was identified having a transposon insertion within the iroCDE operon. The nucleotide sequences flanking either side of the mini-Tn5 insertion are shown as SEQ ID NO. 27 and SEQ ID NO. 30.

The mini-Tn5 transposon is inserted at nucleotide 1272 of SEQ ID NO. 27 and at nucleotide 1 of SEQ ID NO. 30, and interrupts the iroD gene. The N-terminal region of iroD is shown as SEQ ID NO. 29, and the C-terminal region is shown as SEQ ID NO. 31.

In addition to iroD, the gene shown as SEQ ID NO. 27 encodes a partial peptide with the amino acid sequence shown as SEQ ID NO. 28. This amino acid sequence shows 70.9% identity to the putative ATP binding cassette transporter iroC from *Salmonella typhi*.

The gene sequence shown as SEQ ID NO. 30 includes an open reading frame that encodes a peptide with the amino acid sequence shown as SEQ ID NO. 32 and this has sequence homology to the iroE protein from *Salmonella typhi*.

Testing the genes in a model for attenuation of virulence, as described above, showed that the iroD gene was attenuated with a competitive index of 0.107. The mini-Tn5 mutation in the iroD gene has been reintroduced into the wild-type *E. coli* K1 strain by P1 transduction. The resulting transductant is also attenuated in virulence with a competitive index of 0.1. This indicates that the attenuated phenotype is linked to the insertion within iroD. However, it is possible that the attenuation is due to a polar effect on the *E. coli* K1 iroE gene.

EXAMPLE 9

A further mutant was identified with a transposon insertion within the nucleotide sequence shown as SEQ ID NO. 33. The transposon is inserted at nucleotide 2264 of SEQ ID NO. 33. The nucleotide sequence shows sequence homology to the asIA/hemY region of *E. coli* K12 (EMBL accession number AE000456). The asIA encodes an arylsulfatase homologue whereas hemy is involved in the biosynthesis of protoheme IX. This demonstrates that the disrupted region is at least partially identical to the asIA/hemY region of *E. coli* K12.

The transposon is inserted at nucleotide 2264 of SEQ ID NO. 33. This insertion site is 216 nucleotides downstream from the stop codon of the hemY gene and 472 nucleotides upstream from the start codon of the asIA gene.

The novel region has been tested for attenuation of virulence, as described above, and shown to be attenuated with a competitive index of 0.033. The mini-Tn5 mutation in this region has been reintroduced into the wild-type *E. coli* K1 strain by P1 transduction. The resulting transductant is also attenuated in virulence with a competitive index of 0.008. This indicates that the attenuated phenotype is linked to the transposon insertion in this region. However, polar and non-polar deletion mutants of asIA were constructed and tested for attenuation of virulence as described above.

Neither the polar nor the non-polar mutants were attenuated in virulence and this demonstrates that the attenuation of the original transposon mutant is not due to a polar effect on the asIA gene. This indicates that the transposon is disrupting some other function encoded within the intergenic region between asIA and hemY. For example there could be some untranslated RNA molecule, such as a regulatory RNA similar to oxyS (Altuvia et al., Cell, 1997;90:43–53), encoded within this region. Alternatively the transposon could be disrupting some DNA structure that may, for example, be involved in DNA replication. This DNA region is also present in the pathogen *Salmonella typhimurium* suggesting that it may be important for pathogenicity in other organisms. This region (SEQ ID NO. 33) may be used as a target, to identify anti-microbial drugs.

EXAMPLE 10

A further mutant was identified and the DNA region flanking either side of the mini-Tn5 insertion was cloned and had the nucleotide sequence shown as SEQ ID NO. 34. This nucleotide sequence has homology with the mtd2 gene of *Herpetosiphon aurantiacus* (EMBL accession number P25265), with the mtd2 gene product functioning as a cytosine-specific methyltransferase. The mtd2 gene is not found in the *E. coli* K12 genome and may represent a pathogenicity island.

The mini-Tn5 transposon insertions were located at nucleotides 4773 and 3764 of SEQ ID NO. 34 and were shown to interrupt the mtd2 gene.

The amino acid sequence of the mtd2 gene is shown as SEQ ID NO. 43.

The *E. coli* K1 mtd2 gene was tested for attenuation of virulence, as described above, and shown to be attenuated with a competitive index of 0.073.

In addition to the mtd2 gene, a series of open reading frames were also identified with translation products identified herein as MS4 to MS16, SEQ ID NOS. 48–44 and 42–35, respectively. As the open reading frames are located in a potential pathogenicity island, mutations in these genes may also result in attenuation in virulence. Further, since it is known that *E. coli* and other bacteria may encode peptides in different forms in the nucleotide sequence, the coding regions of some of these proteins may overlap. In addition, any aminoacid sequence shown starting with Val may in fact start with Met.

What is claimed is:

1. A method for screening a potential drug using a peptide, said method comprising:
   contacting the peptide with the potential drug, wherein the peptide has the ability to translocate a protein from the bacterial cytoplasm to the periplasm; and
   determining whether the potential drug inhibits the ability of the peptide to translocate a protein from the bacterial cytoplasm to the periplasm, wherein the peptide is encoded by a gene selected from the group consisting of tatA, tatB, tatC, and tatE, or the obtainable from a Gram-negative bacterium nucleotide or amino acid level.

2. The method of claim 1, wherein the peptide is encoded by the tatB gene.

3. The method of claim 1, wherein the peptide comprises an amino acid sequence selected from the group consisting of SEQ ID NO:11, SEQ ID NO:12, SEQ ID NO:13, and SEQ ID NO:15.

4. The method of claim 1, wherein the peptide comprises the amino acid sequence of SEQ ID NO:12.

* * * * *

UNITED STATES PATENT AND TRADEMARK OFFICE
CERTIFICATE OF CORRECTION

PATENT NO. : 6,846,667 B1
DATED : January 25, 2005
INVENTOR(S) : Crooke et al.

It is certified that error appears in the above-identified patent and that said Letters Patent is hereby corrected as shown below:

Column 1,
Line 4, should read -- Cross-Reference to Related Application
This application is the National Stage of International Application Number PCT/GB99/03721, filed November 9, 1999. --

Column 137,
Line 24, "tatE, or the obtainable" should read -- tatE, obtainable --.
Lines 14-15, "bacterium nucleotide of amino acid level." should read -- bacterium. --.

Signed and Sealed this

Tenth Day of May, 2005

JON W. DUDAS
*Director of the United States Patent and Trademark Office*

SEQUENCE LISTING

<160> NUMBER OF SEQ ID NOS: 72

<210> SEQ ID NO 1
<211> LENGTH: 4333
<212> TYPE: DNA
<213> ORGANISM: Escherichia coli
<220> FEATURE:
<221> NAME/KEY: CDS
<222> LOCATION: (1017)..(2549)

<400> SEQUENCE: 1

```
ccattactca gaatgggcgg atacacaata aaaattgttc ttcttattac cgcataaccg      60
atgccgaggc acaaaaaaat caccgatagt tttaccatcg agaatttttt attcgtttta     120 tcagaattt  ctaaattatt tctgatacgt ttgaatatcc agacgcacag cgtcgtcatg     180
accactaaca ccagtaaaaa ccacaggtgt gatattaatt cccaggccaa cgtattatat     240
ttgtcataca atgacagtcc aggccaactt tccgctttcc ctttgacgta ttgcagcata     300
ataaattgcg gcaatgtcag taggggggatg gctgttaaca tcgggatacc tacacgttcg     360
acacgtactt tccaccattt tttcaaggga tagcgtaaaa aaagcatgta ggaaaagtac     420
ccggatataa cgaaaaatac ctgcatgcgg aacgagtgga tgaagtcatt aaaaagggtc     480
agccataatg acggttcggc gctattcaca tgccatgtat ggctcgaata gattaaagaa     540
atatgaaaag ggatccctaa caacatcagc caggcgcgga tggagtcgag gaaatattca     600
cgttgcgcgg gtactgggtt catatatggt taactaatct cggattttc gtcttatccc      660 tgtcgggtta tgcctttagg cttgttgcca tagcgacacc gacctgaccg cgccaggcgc     720
aggcttcaag gttttatgc atagcatcat cgctaccact aaccagaatg gaagcgtctg      780
taagacggtt gataaataaa tttgctggca aaccctacac gaagtcgatg cttctgtctt     840
taggagaagc acggaaagtg aaaacggttg caatcaggtg cttaatccat gagccagtgt     900
gctgaacgat accgggattc tgttgtcgga atggcaggtt atccattaaa atagatcgga     960
tcgatataag cacacaaagg gggaagtgct tactaattat gaaacataaa ctacaa atg    1019
                                                                Met
                                                                  1 atg aaa atg cgt tgg ttg agt gct gca gta atg tta acc ctg tat aca       1067
Met Lys Met Arg Trp Leu Ser Ala Ala Val Met Leu Thr Leu Tyr Thr
          5                  10                  15 tct tca agc tgg gct ttc agt att gat gat gtc gca aag caa gct caa       1115
Ser Ser Ser Trp Ala Phe Ser Ile Asp Asp Val Ala Lys Gln Ala Gln
     20                  25                  30 tcc tta gcc ggg aaa ggc tat gag gcg ccc aaa agc aac ttg ccc tcc       1163
Ser Leu Ala Gly Lys Gly Tyr Glu Ala Pro Lys Ser Asn Leu Pro Ser
 35                  40                  45 gtt ttc cgc gat atg aaa tac gcg gac tat cag cag atc cag ttt aat       1211
Val Phe Arg Asp Met Lys Tyr Ala Asp Tyr Gln Gln Ile Gln Phe Asn
 50                  55                  60                  65 cat gac aaa gcg tac tgg aac aat ctg aag acc cca ttc aaa ctc gag       1259
His Asp Lys Ala Tyr Trp Asn Asn Leu Lys Thr Pro Phe Lys Leu Glu
                 70                  75                  80 ttc tac cat cag ggt atg tac ttc gat acc ccg gtc aaa ata aat gaa       1307
Phe Tyr His Gln Gly Met Tyr Phe Asp Thr Pro Val Lys Ile Asn Glu
             85                  90                  95 gtg act gcc acc gca gtc aaa cga atc aaa tac agc ccg gat tat ttc       1355
Val Thr Ala Thr Ala Val Lys Arg Ile Lys Tyr Ser Pro Asp Tyr Phe
        100                 105                 110
```

-continued

```
act ttc ggc gat gtt cag cat gac aaa gac acg gta aaa gac ctt ggt    1403
Thr Phe Gly Asp Val Gln His Asp Lys Asp Thr Val Lys Asp Leu Gly
    115                 120                 125 ttt gcc ggt ttc aaa gtg ctt tac ccg atc aac agc aaa gat aaa aac    1451
Phe Ala Gly Phe Lys Val Leu Tyr Pro Ile Asn Ser Lys Asp Lys Asn
130                 135                 140                 145 gat gaa atc gtc agc atg ctc ggg gcc agc tat ttc cgc gtg att ggt    1499
Asp Glu Ile Val Ser Met Leu Gly Ala Ser Tyr Phe Arg Val Ile Gly
                150                 155                 160 gca ggt cag gtt tat ggc ctt tct gca cgc ggc ctg gca att gat acc    1547
Ala Gly Gln Val Tyr Gly Leu Ser Ala Arg Gly Leu Ala Ile Asp Thr
165                 170                 175 gcc ttg cca tcg ggt gaa gaa ttt cca cgc ttc aaa gag ttc tgg atc    1595
Ala Leu Pro Ser Gly Glu Glu Phe Pro Arg Phe Lys Glu Phe Trp Ile
        180                 185                 190 gag cgt cca aaa ccg act gat aaa cgt tta acc att tat gca ttg ctt    1643
Glu Arg Pro Lys Pro Thr Asp Lys Arg Leu Thr Ile Tyr Ala Leu Leu
195                 200                 205 gac tcg ccg cgc gcg aca ggt gct tac aaa ttc gta gtt atg cca gga    1691
Asp Ser Pro Arg Ala Thr Gly Ala Tyr Lys Phe Val Val Met Pro Gly
210                 215                 220                 225 cgt gac acg gtt gtg gat gtg cag tcg aaa atc tat ctg cgc gat aaa    1739
Arg Asp Thr Val Val Asp Val Gln Ser Lys Ile Tyr Leu Arg Asp Lys
                230                 235                 240 gtc ggc aaa ctg ggg gtt gca ccg tta acc agt atg ttc ctg ttt ggg    1787
Val Gly Lys Leu Gly Val Ala Pro Leu Thr Ser Met Phe Leu Phe Gly
            245                 250                 255 ccg aac caa ccg tcg cct gca aat aac tat cgt ccg gag ttg cac gac    1835
Pro Asn Gln Pro Ser Pro Ala Asn Asn Tyr Arg Pro Glu Leu His Asp
        260                 265                 270 tct aac ggt ctg tct atc cat gct ggt aat ggc gaa tgg atc tgg cgt    1883
Ser Asn Gly Leu Ser Ile His Ala Gly Asn Gly Glu Trp Ile Trp Arg
275                 280                 285 ccg ttg aat aac ccg aaa cat tta gcg gtc agc agc ttc tcg atg gaa    1931
Pro Leu Asn Asn Pro Lys His Leu Ala Val Ser Ser Phe Ser Met Glu
290                 295                 300                 305 aac ccg caa ggc ttc ggt cta ttg cag cgt ggt cgt gat ttc tcc cgc    1979
Asn Pro Gln Gly Phe Gly Leu Leu Gln Arg Gly Arg Asp Phe Ser Arg
                310                 315                 320 ttt gaa gat ctc gat gat cgt tac gat ctt cgt cca agc gca tgg gtg    2027
Phe Glu Asp Leu Asp Asp Arg Tyr Asp Leu Arg Pro Ser Ala Trp Val
            325                 330                 335 act ccg aaa ggg gag tgg ggc aaa ggc agc gtt gag ctg gtg gaa att    2075
Thr Pro Lys Gly Glu Trp Gly Lys Gly Ser Val Glu Leu Val Glu Ile
        340                 345                 350 cca acc aac gat gaa acc aac gat aac atc gtc gct tac tgg acg ccg    2123
Pro Thr Asn Asp Glu Thr Asn Asp Asn Ile Val Ala Tyr Trp Thr Pro
355                 360                 365 gat cag ctg ccg gag ccg ggt aaa gag atg aac ttt aaa tac acc atc    2171
Asp Gln Leu Pro Glu Pro Gly Lys Glu Met Asn Phe Lys Tyr Thr Ile
370                 375                 380                 385 acc ttc agc cgt gat gaa gac aaa ctg cat gcg cca gat aac gca tgg    2219
Thr Phe Ser Arg Asp Glu Asp Lys Leu His Ala Pro Asp Asn Ala Trp
                390                 395                 400 gtg caa caa acg cgt cgt tca acg ggg gat gtg aag cag tcg aac ctg    2267
Val Gln Gln Thr Arg Arg Ser Thr Gly Asp Val Lys Gln Ser Asn Leu
            405                 410                 415 att cgc cag cct gac ggt act atc gcc ttt gtg gtc gat ttt acc ggc    2315
Ile Arg Gln Pro Asp Gly Thr Ile Ala Phe Val Val Asp Phe Thr Gly
        420                 425                 430
```

```
gct gag atg aaa aaa ctg cca gag gat acc ccg gtc aca gcg caa acc      2363
Ala Glu Met Lys Lys Leu Pro Glu Asp Thr Pro Val Thr Ala Gln Thr
        435                 440                 445 agc att ggt gat aat ggt gag ata gtt gaa agc acg gtg cgt tat aac      2411
Ser Ile Gly Asp Asn Gly Glu Ile Val Glu Ser Thr Val Arg Tyr Asn
450                 455                 460                 465 ccg gtt acc aaa ggc tgg cgt ctg gtg atg cgt gtg aaa gtg aaa gat      2459
Pro Val Thr Lys Gly Trp Arg Leu Val Met Arg Val Lys Val Lys Asp
                470                 475                 480 gcc aag aaa acc act gaa atg cgt gct gcg ctg gtg aat gcc gat cag      2507
Ala Lys Lys Thr Thr Glu Met Arg Ala Ala Leu Val Asn Ala Asp Gln
            485                 490                 495 acg ttg agt gaa acc tgg agc tac cag tta cct gcc aat gaa              2549
Thr Leu Ser Glu Thr Trp Ser Tyr Gln Leu Pro Ala Asn Glu
        500                 505                 510 taagacaact gagtacattg acgcaatgcc catcgccgca agcgagaaag cggcattgcc    2609
gaagactgat atccgcgccg ttcatcaggc gctggatgcc gaacaccgca cctgggcgcg    2669
ggaggatgac tccccgcaag gctcggtaaa ggcgcgtctg gaacaagcct ggccagattc    2729
acttgctgat ggacagttaa ttaaagacga cgaagggcgc gatcagctaa aggcgatgcc    2789
agaagtaaaa cgctcctcga tgtttcccga cccgtggcgt accaacccgg taggccgttt    2849
ctgggatcgc ctgcgtggac gcgatgtgac gccgcgctat ctggctcgtt tgaccaaaga    2909
agagcaggag agtgagcaaa agtggcgtac cgtcggtacc atccgccgtt acattctgtt    2969
gatcctgacg ctcgcgcaaa ctgttgtcgc gacctggtat atgaagacca ttcttcctta    3029 tcagggtgg cgctgatta atcctatgga tatggttggt caggatgtgt gggtttcctt     3089
tatgcagctt ctgccttata tgctgcaaac cggtatcctg atcctctttg cggtactgtt    3149
ctgttgggtg tccgccggat tctggaccgg cgttgatggg cttcctgcaa ctgcttattg    3209
gtcgcgataa atacagtata tctgcgtcaa cagttggcga tgaaccatta aacccggagc    3269
atcgcacggc gttgatcatg cctatctgta acgaagacgt gaaccgtgtt tttgctggct    3329
tgcgtgcaac gtgggaatca gtaaaagcca cgggaatgc caaacatttt gatgtctaca    3389
ttcttagtga cagttataac ccggatatct gcgtcgcaga gcaaaaagcc tggatggagc    3449
ttatcgctga agtcggtggc gaaggtcaga ttttctatcg ccgccgccgc cgtcgcgtga    3509
agcgtaaaag cggtaatatc gatgacttct gccgtcgctg gggcagccag tacagctaca    3569
tggtggtgct ggatgctgac tcggtaatga ccggtgattg tttgtgcggc ctggtgcgcc    3629
tgatggaagc caacccgaac gccgggatca ttcagtcgtc gccgaaagcg tccggcatgg    3689
atacgctgta tgcgcgctgt cagcagttcg cgacccgcgt gtatgggcca ctgtttacag    3749 ccggttttgca cttctggcaa cttggcgagt cgcactactg ggggcataac gcgattatcc    3809
gcgtgaaacc gtttatcgag cactgtgcac tggctccgct gccgggcgaa ggttcttttg    3869
ccggttcaat cctgtcacat gacttcgtgg aagcggcgtt gatgcgccgt gcaggttggg    3929
gggtctggat tgcttacgat ctcccggggtt cttatgaaga attaccgcct aacttgcttg    3989
atgagctaaa acgtgaccgc cgctggtgcc acggtaacct gatgaacttc cgtctgttcc    4049
tggtgaaggg tatgcacccg gttcaccgtg cggtgttcct gacgggcgtg atgtcttatc    4109
tctccgctcc gctgtggttt atgttcctcg cgctctctac tgcattgcag gtagtacatg    4169
cgttgaccga accgcaatac ttcctgcaac cacggcagtt gttcccggta tggccgcagt    4229
ggcgtcctga gctggcgatt gcacttttg cttcgaccat ggtgctgttg ttcctgccga    4289
```

-continued agctattgag cattttgctt atctggtgca aaggaacgaa agaa 4333

<210> SEQ ID NO 2
<211> LENGTH: 511
<212> TYPE: PRT
<213> ORGANISM: Escherichia coli

<400> SEQUENCE: 2

| Met | Met | Lys | Met | Arg | Trp | Leu | Ser | Ala | Ala | Val | Met | Leu | Thr | Leu | Tyr |
|---|---|---|---|---|---|---|---|---|---|---|---|---|---|---|---|
| 1 | | | | 5 | | | | | 10 | | | | | 15 | |

| Thr | Ser | Ser | Ser | Trp | Ala | Phe | Ser | Ile | Asp | Asp | Val | Ala | Lys | Gln | Ala |
|---|---|---|---|---|---|---|---|---|---|---|---|---|---|---|---|
| | | | 20 | | | | | 25 | | | | | 30 | | |

| Gln | Ser | Leu | Ala | Gly | Lys | Gly | Tyr | Glu | Ala | Pro | Lys | Ser | Asn | Leu | Pro |
|---|---|---|---|---|---|---|---|---|---|---|---|---|---|---|---|
| | | 35 | | | | | 40 | | | | | 45 | | | |

| Ser | Val | Phe | Arg | Asp | Met | Lys | Tyr | Ala | Asp | Tyr | Gln | Gln | Ile | Gln | Phe |
|---|---|---|---|---|---|---|---|---|---|---|---|---|---|---|---|
| | 50 | | | | | 55 | | | | | 60 | | | | |

| Asn | His | Asp | Lys | Ala | Tyr | Trp | Asn | Asn | Leu | Lys | Thr | Pro | Phe | Lys | Leu |
|---|---|---|---|---|---|---|---|---|---|---|---|---|---|---|---|
| 65 | | | | | 70 | | | | | 75 | | | | | 80 |

| Glu | Phe | Tyr | His | Gln | Gly | Met | Tyr | Phe | Asp | Thr | Pro | Val | Lys | Ile | Asn |
|---|---|---|---|---|---|---|---|---|---|---|---|---|---|---|---|
| | | | | 85 | | | | | 90 | | | | | 95 | |

| Glu | Val | Thr | Ala | Thr | Ala | Val | Lys | Arg | Ile | Lys | Tyr | Ser | Pro | Asp | Tyr |
|---|---|---|---|---|---|---|---|---|---|---|---|---|---|---|---|
| | | | | 100 | | | | | 105 | | | | | 110 | |

| Phe | Thr | Phe | Gly | Asp | Val | Gln | His | Asp | Lys | Asp | Thr | Val | Lys | Asp | Leu |
|---|---|---|---|---|---|---|---|---|---|---|---|---|---|---|---|
| | | | 115 | | | | | 120 | | | | | 125 | | |

| Gly | Phe | Ala | Gly | Phe | Lys | Val | Leu | Tyr | Pro | Ile | Asn | Ser | Lys | Asp | Lys |
|---|---|---|---|---|---|---|---|---|---|---|---|---|---|---|---|
| | 130 | | | | | 135 | | | | | 140 | | | | |

| Asn | Asp | Glu | Ile | Val | Ser | Met | Leu | Gly | Ala | Ser | Tyr | Phe | Arg | Val | Ile |
|---|---|---|---|---|---|---|---|---|---|---|---|---|---|---|---|
| 145 | | | | | 150 | | | | | 155 | | | | | 160 |

| Gly | Ala | Gly | Gln | Val | Tyr | Gly | Leu | Ser | Ala | Arg | Gly | Leu | Ala | Ile | Asp |
|---|---|---|---|---|---|---|---|---|---|---|---|---|---|---|---|
| | | | | 165 | | | | | 170 | | | | | 175 | |

| Thr | Ala | Leu | Pro | Ser | Gly | Glu | Glu | Phe | Pro | Arg | Phe | Lys | Glu | Phe | Trp |
|---|---|---|---|---|---|---|---|---|---|---|---|---|---|---|---|
| | | | 180 | | | | | 185 | | | | | 190 | | |

| Ile | Glu | Arg | Pro | Lys | Pro | Thr | Asp | Lys | Arg | Leu | Thr | Ile | Tyr | Ala | Leu |
|---|---|---|---|---|---|---|---|---|---|---|---|---|---|---|---|
| | | 195 | | | | | 200 | | | | | 205 | | | |

| Leu | Asp | Ser | Pro | Arg | Ala | Thr | Gly | Ala | Tyr | Lys | Phe | Val | Val | Met | Pro |
|---|---|---|---|---|---|---|---|---|---|---|---|---|---|---|---|
| | 210 | | | | | 215 | | | | | 220 | | | | |

| Gly | Arg | Asp | Thr | Val | Val | Asp | Val | Gln | Ser | Lys | Ile | Tyr | Leu | Arg | Asp |
|---|---|---|---|---|---|---|---|---|---|---|---|---|---|---|---|
| 225 | | | | | 230 | | | | | 235 | | | | | 240 |

| Lys | Val | Gly | Lys | Leu | Gly | Val | Ala | Pro | Leu | Thr | Ser | Met | Phe | Leu | Phe |
|---|---|---|---|---|---|---|---|---|---|---|---|---|---|---|---|
| | | | | 245 | | | | | 250 | | | | | 255 | |

| Gly | Pro | Asn | Gln | Pro | Ser | Pro | Ala | Asn | Asn | Tyr | Arg | Pro | Glu | Leu | His |
|---|---|---|---|---|---|---|---|---|---|---|---|---|---|---|---|
| | | | | 260 | | | | | 265 | | | | | 270 | |

| Asp | Ser | Asn | Gly | Leu | Ser | Ile | His | Ala | Gly | Asn | Gly | Glu | Trp | Ile | Trp |
|---|---|---|---|---|---|---|---|---|---|---|---|---|---|---|---|
| | 275 | | | | | 280 | | | | | 285 | | | | |

| Arg | Pro | Leu | Asn | Asn | Pro | Lys | His | Leu | Ala | Val | Ser | Ser | Phe | Ser | Met |
|---|---|---|---|---|---|---|---|---|---|---|---|---|---|---|---|
| | 290 | | | | | 295 | | | | | 300 | | | | |

| Glu | Asn | Pro | Gln | Gly | Phe | Gly | Leu | Leu | Gln | Arg | Gly | Arg | Asp | Phe | Ser |
|---|---|---|---|---|---|---|---|---|---|---|---|---|---|---|---|
| 305 | | | | | 310 | | | | | 315 | | | | | 320 |

| Arg | Phe | Glu | Asp | Leu | Asp | Asp | Arg | Tyr | Asp | Leu | Arg | Pro | Ser | Ala | Trp |
|---|---|---|---|---|---|---|---|---|---|---|---|---|---|---|---|
| | | | | 325 | | | | | 330 | | | | | 335 | |

| Val | Thr | Pro | Lys | Gly | Glu | Trp | Gly | Lys | Gly | Ser | Val | Glu | Leu | Val | Glu |
|---|---|---|---|---|---|---|---|---|---|---|---|---|---|---|---|
| | | | 340 | | | | | 345 | | | | | 350 | | |

| Ile | Pro | Thr | Asn | Asp | Glu | Thr | Asn | Asp | Asn | Ile | Val | Ala | Tyr | Trp | Thr |
|---|---|---|---|---|---|---|---|---|---|---|---|---|---|---|---|
| | | 355 | | | | | 360 | | | | | 365 | | | |

```
Pro Asp Gln Leu Pro Glu Pro Gly Lys Glu Met Asn Phe Lys Tyr Thr
    370             375                 380
Ile Thr Phe Ser Arg Asp Glu Asp Lys Leu His Ala Pro Asp Asn Ala
385                 390                 395                 400
Trp Val Gln Thr Arg Arg Ser Thr Gly Asp Val Lys Gln Ser Asn
                405                 410                 415
Leu Ile Arg Gln Pro Asp Gly Thr Ile Ala Phe Val Val Asp Phe Thr
            420                 425                 430
Gly Ala Glu Met Lys Lys Leu Pro Glu Asp Thr Pro Val Thr Ala Gln
            435                 440                 445
Thr Ser Ile Gly Asp Asn Gly Glu Ile Val Glu Ser Thr Val Arg Tyr
    450                 455                 460
Asn Pro Val Thr Lys Gly Trp Arg Leu Val Met Arg Val Lys Val Lys
465                 470                 475                 480
Asp Ala Lys Lys Thr Thr Glu Met Arg Ala Ala Leu Val Asn Ala Asp
                485                 490                 495
Gln Thr Leu Ser Glu Thr Trp Ser Tyr Gln Leu Pro Ala Asn Glu
            500                 505                 510
```

<210> SEQ ID NO 3
<211> LENGTH: 574
<212> TYPE: DNA
<213> ORGANISM: Escherichia coli

<400> SEQUENCE: 3

```
ttcgttgatc ctgtcaccgt tgttcggtt atttccagcc gtgccaccgt tggtctgcga      60
accaaacgct ggaaactgtt ccctgatccc ggaagagtat tcaccgccgc aggtgctggt    120
tgataccgat cggttccttg agatgaatcg tcaatgctcc cttgatgatg gttttatgca    180
cgcggtgttt aacccgtcat ttaacgctct ggcaaccgca atggcgaccg cgcgtcaccg    240
cgccagcaag gtgctggaaa tcgcccgtga ccgccacgtt gaacaggcgc tgaacgagac    300
gccagagaag ctgaatcgcg atcgtcgcct ggtgctgcta agcgatccgg tgacgatggc    360
ccgtctgcat ttccgcgtct ggaattcccc ggagagatat tcttcatggg tgagttatta    420
cgaagggata aagctcaatc cactggcatt gcgtaaaccg atgcggctt cgcaataaaa    480
acgtagttgc ctgatgcgct acgcttatca ggcctacatc gttcctgcaa tttattgatt    540
ttgcaagatt ttgtaggtcg gataaggcgt tcac                                574
```

<210> SEQ ID NO 4
<211> LENGTH: 1478
<212> TYPE: DNA
<213> ORGANISM: Escherichia coli
<220> FEATURE:
<221> NAME/KEY: CDS
<222> LOCATION: (25)..(1449)

<400> SEQUENCE: 4

```
gggataatgc ctgaggggcc tgta atg cgt atc ggc atg cgg ttg ttg ctg        51
                          Met Arg Ile Gly Met Arg Leu Leu Leu
                            1               5
ggc tat ttt tta ctg gtg gcg gtg gcg gcc tgg ttc gta ctg gct att       99
Gly Tyr Phe Leu Leu Val Ala Val Ala Ala Trp Phe Val Leu Ala Ile
         10                  15                  20                  25
ttt gtc aaa gaa gtt aaa ccg ggc gtg cga aga gca acc gag ggg acg      147
Phe Val Lys Glu Val Lys Pro Gly Val Arg Arg Ala Thr Glu Gly Thr
             30                  35                  40
tta atc gac acc gca acg ttg ctg gcg gag ctg gcg cgt ccc gat ttg      195
```

```
                Leu Ile Asp Thr Ala Thr Leu Leu Ala Glu Leu Ala Arg Pro Asp Leu
                        45                  50                  55 ctc tct ggg gac cca acg cat ggg caa ctg gcg cag gcg ttt aat cag       243
Leu Ser Gly Asp Pro Thr His Gly Gln Leu Ala Gln Ala Phe Asn Gln
         60                  65                  70 cta caa cat cgc ccg ttt cgc gcc aat atc ggt ggc att aac aaa gtg       291
Leu Gln His Arg Pro Phe Arg Ala Asn Ile Gly Gly Ile Asn Lys Val
     75                  80                  85 cgc aac gaa tat cat gtc tat atg acc gat gcg cag ggc aaa gta ttg       339
Arg Asn Glu Tyr His Val Tyr Met Thr Asp Ala Gln Gly Lys Val Leu
 90                  95                 100                 105 ttc gat tcg gca aat aaa gcc gtt gga cag gat tat tcg cgc tgg aat       387
Phe Asp Ser Ala Asn Lys Ala Val Gly Gln Asp Tyr Ser Arg Trp Asn
                 110                 115                 120 gac gtc tgg cta acg ttg cgt ggt cag tat ggt gcg cgc agc acg ttg       435
Asp Val Trp Leu Thr Leu Arg Gly Gln Tyr Gly Ala Arg Ser Thr Leu
             125                 130                 135 caa aat cct gcc gat ccc gaa agt tct gtg atg tat gtt gcc gcg ccg       483
Gln Asn Pro Ala Asp Pro Glu Ser Ser Val Met Tyr Val Ala Ala Pro
         140                 145                 150 att atg gac ggc tcg cgg ctt att ggc gtt ttg agc gta ggc aaa ccg       531
Ile Met Asp Gly Ser Arg Leu Ile Gly Val Leu Ser Val Gly Lys Pro
     155                 160                 165 aac gcg gcg atg gct ccg gtc att aag cgt agc gag cgg cga att tta       579
Asn Ala Ala Met Ala Pro Val Ile Lys Arg Ser Glu Arg Arg Ile Leu
170                 175                 180                 185 tgg gcc agc gcc att ttg ttg ggg att gca ctg gtg att ggc gca ggc       627
Trp Ala Ser Ala Ile Leu Leu Gly Ile Ala Leu Val Ile Gly Ala Gly
                 190                 195                 200 atg gtt tgg tgg atc aac cgc tct att gcc agg ctc act cgc tat gct       675
Met Val Trp Trp Ile Asn Arg Ser Ile Ala Arg Leu Thr Arg Tyr Ala
             205                 210                 215 gat tcc gtc act gac aat aag ccc gtt cct ctc ccc gat ctc ggt agt       723
Asp Ser Val Thr Asp Asn Lys Pro Val Pro Leu Pro Asp Leu Gly Ser
         220                 225                 230 agc gag ttg cgt aaa ctc gcg cag gcg ctg gaa agt atg cgc gtg aag       771
Ser Glu Leu Arg Lys Leu Ala Gln Ala Leu Glu Ser Met Arg Val Lys
     235                 240                 245 ctg gaa ggg aaa aac tat att gag cag tat gtt tat gcg tta act cat       819
Leu Glu Gly Lys Asn Tyr Ile Glu Gln Tyr Val Tyr Ala Leu Thr His
250                 255                 260                 265 gag cta aaa agc cca ctg gcg gcg att cgt ggc gcg gcg gaa att tta       867
Glu Leu Lys Ser Pro Leu Ala Ala Ile Arg Gly Ala Ala Glu Ile Leu
                 270                 275                 280 cgc gaa ggt ccg ccg ccg gaa gtg gtg gct cgt ttt acc gac aac att       915
Arg Glu Gly Pro Pro Pro Glu Val Val Ala Arg Phe Thr Asp Asn Ile
             285                 290                 295 ctg acg caa aat gcg cga atg cag gca ctg gtg gaa acg tta cta cgc       963
Leu Thr Gln Asn Ala Arg Met Gln Ala Leu Val Glu Thr Leu Leu Arg
         300                 305                 310 cag gca aga ctg gag aat cgt cag gaa gtc gtt ctg act gct gtt gat      1011
Gln Ala Arg Leu Glu Asn Arg Gln Glu Val Val Leu Thr Ala Val Asp
     315                 320                 325 gtg gcg gca tta ttt cgc cgc gtc agc gaa gcg cgc acc gtg cag ttg      1059
Val Ala Ala Leu Phe Arg Arg Val Ser Glu Ala Arg Thr Val Gln Leu
330                 335                 340                 345 gca gaa aaa aac atc act ttg cat gtt atg cct act gag gtt aac gtt      1107
Ala Glu Lys Asn Ile Thr Leu His Val Met Pro Thr Glu Val Asn Val
                 350                 355                 360
```

-continued

```
gct tct gaa ccg gcg tta ctg gag cag gcg ctg ggg aat tta ctg gat    1155
Ala Ser Glu Pro Ala Leu Leu Glu Gln Ala Leu Gly Asn Leu Leu Asp
        365                 370                 375 aac gcc atc gat ttt act ccc gag agc ggt tgc ata acg cta agc gcc    1203
Asn Ala Ile Asp Phe Thr Pro Glu Ser Gly Cys Ile Thr Leu Ser Ala
380                 385                 390 gaa gtg gat cag gaa tac gtc acc ctt aag gtg ctg gat acc ggt agt    1251
Glu Val Asp Gln Glu Tyr Val Thr Leu Lys Val Leu Asp Thr Gly Ser
395                 400                 405 ggg att cct gac tac gcg ctg tca cgt att ttt gaa cgc ttt tac tct    1299
Gly Ile Pro Asp Tyr Ala Leu Ser Arg Ile Phe Glu Arg Phe Tyr Ser
410                 415                 420                 425 ttg ccg cgt gca aat ggg caa aaa agc agc ggt ctg ggg ttg gcg ttt    1347
Leu Pro Arg Ala Asn Gly Gln Lys Ser Ser Gly Leu Gly Leu Ala Phe
                430                 435                 440 gtc agt gag gtc gcc cgt ttg ttt aac ggc gaa gtc acg ctg cgc aac    1395
Val Ser Glu Val Ala Arg Leu Phe Asn Gly Glu Val Thr Leu Arg Asn
            445                 450                 455 gtg cag gaa ggt ggc gtg ctg gcc tcg ctt cga ctt cac cgt cac ttc    1443
Val Gln Glu Gly Gly Val Leu Ala Ser Leu Arg Leu His Arg His Phe
        460                 465                 470 aca tag cttcaaattc ttcccacata gtcttcgta                            1478
Thr
    475
```

<210> SEQ ID NO 5
<211> LENGTH: 474
<212> TYPE: PRT
<213> ORGANISM: Escherichia coli

<400> SEQUENCE: 5

```
Met Arg Ile Gly Met Arg Leu Leu Leu Gly Tyr Phe Leu Leu Val Ala
 1               5                  10                  15

Val Ala Ala Trp Phe Val Leu Ala Ile Phe Val Lys Glu Val Lys Pro
            20                  25                  30

Gly Val Arg Arg Ala Thr Glu Gly Thr Leu Ile Asp Thr Ala Thr Leu
        35                  40                  45

Leu Ala Glu Leu Ala Arg Pro Asp Leu Leu Ser Gly Asp Pro Thr His
    50                  55                  60

Gly Gln Leu Ala Gln Ala Phe Asn Gln Leu Gln His Arg Pro Phe Arg
65                  70                  75                  80

Ala Asn Ile Gly Gly Ile Asn Lys Val Arg Asn Glu Tyr His Val Tyr
                85                  90                  95

Met Thr Asp Ala Gln Gly Lys Val Leu Phe Asp Ser Ala Asn Lys Ala
            100                 105                 110

Val Gly Gln Asp Tyr Ser Arg Trp Asn Asp Val Trp Leu Thr Leu Arg
        115                 120                 125

Gly Gln Tyr Gly Ala Arg Ser Thr Leu Gln Asn Pro Ala Asp Pro Glu
    130                 135                 140

Ser Ser Val Met Tyr Val Ala Ala Pro Ile Met Asp Gly Ser Arg Leu
145                 150                 155                 160

Ile Gly Val Leu Ser Val Gly Lys Pro Asn Ala Ala Met Ala Pro Val
                165                 170                 175

Ile Lys Arg Ser Glu Arg Arg Ile Leu Trp Ala Ser Ala Ile Leu Leu
            180                 185                 190

Gly Ile Ala Leu Val Ile Gly Ala Gly Met Val Trp Trp Ile Asn Arg
        195                 200                 205
```

```
Ser Ile Ala Arg Leu Thr Arg Tyr Ala Asp Ser Val Thr Asp Asn Lys
210                 215                 220

Pro Val Pro Leu Pro Asp Leu Gly Ser Ser Glu Leu Arg Lys Leu Ala
225                 230                 235                 240

Gln Ala Leu Glu Ser Met Arg Val Lys Leu Glu Gly Lys Asn Tyr Ile
                245                 250                 255

Glu Gln Tyr Val Tyr Ala Leu Thr His Glu Leu Lys Ser Pro Leu Ala
            260                 265                 270

Ala Ile Arg Gly Ala Ala Glu Ile Leu Arg Glu Gly Pro Pro Pro Glu
        275                 280                 285

Val Val Ala Arg Phe Thr Asp Asn Ile Leu Thr Gln Asn Ala Arg Met
290                 295                 300

Gln Ala Leu Val Glu Thr Leu Leu Arg Gln Ala Arg Leu Glu Asn Arg
305                 310                 315                 320

Gln Glu Val Val Leu Thr Ala Val Asp Val Ala Ala Leu Phe Arg Arg
                325                 330                 335

Val Ser Glu Ala Arg Thr Val Gln Leu Ala Glu Lys Asn Ile Thr Leu
            340                 345                 350

His Val Met Pro Thr Glu Val Asn Val Ala Ser Glu Pro Ala Leu Leu
        355                 360                 365

Glu Gln Ala Leu Gly Asn Leu Leu Asp Asn Ala Ile Asp Phe Thr Pro
370                 375                 380

Glu Ser Gly Cys Ile Thr Leu Ser Ala Glu Val Asp Gln Glu Tyr Val
385                 390                 395                 400

Thr Leu Lys Val Leu Asp Thr Gly Ser Gly Ile Pro Asp Tyr Ala Leu
                405                 410                 415

Ser Arg Ile Phe Glu Arg Phe Tyr Ser Leu Pro Arg Ala Asn Gly Gln
            420                 425                 430

Lys Ser Ser Gly Leu Gly Leu Ala Phe Val Ser Glu Val Ala Arg Leu
        435                 440                 445

Phe Asn Gly Glu Val Thr Leu Arg Asn Val Gln Glu Gly Gly Val Leu
450                 455                 460

Ala Ser Leu Arg Leu His Arg His Phe Thr
465                 470

<210> SEQ ID NO 6
<211> LENGTH: 128
<212> TYPE: DNA
<213> ORGANISM: Escherichia coli
<220> FEATURE:
<221> NAME/KEY: CDS
<222> LOCATION: (1)..(126)

<400> SEQUENCE: 6 atg aaa ggt cgc ctg tta gat gct gtc ccg ctc agt tcc cta acg ggc    48
Met Lys Gly Arg Leu Leu Asp Ala Val Pro Leu Ser Ser Leu Thr Gly
  1               5                  10                  15 gtt ggc gca gcg ctt agt aac aag ctg gcg aaa atc aac ctg cat acc    96
Val Gly Ala Ala Leu Ser Asn Lys Leu Ala Lys Ile Asn Leu His Thr
                 20                  25                  30 gta cag gat tta ctc tta cac ctt cct ctg cg                        128
Val Gln Asp Leu Leu Leu His Leu Pro Leu
             35                  40

<210> SEQ ID NO 7
<211> LENGTH: 42
<212> TYPE: PRT
```

<213> ORGANISM: Escherichia coli

<400> SEQUENCE: 7

| Met | Lys | Gly | Arg | Leu | Leu | Asp | Ala | Val | Pro | Ser | Ser | Leu | Thr | Gly |
|---|---|---|---|---|---|---|---|---|---|---|---|---|---|---|
| 1 | | | | 5 | | | | | 10 | | | | | 15 |

| Val | Gly | Ala | Ala | Leu | Ser | Asn | Lys | Leu | Ala | Lys | Ile | Asn | Leu | His | Thr |
|---|---|---|---|---|---|---|---|---|---|---|---|---|---|---|---|
| | | | 20 | | | | | 25 | | | | | 30 | | |

| Val | Gln | Asp | Leu | Leu | Leu | His | Leu | Pro | Leu |
|---|---|---|---|---|---|---|---|---|---|
| | | 35 | | | | | 40 | | |

<210> SEQ ID NO 8
<211> LENGTH: 1174
<212> TYPE: DNA
<213> ORGANISM: Escherichia coli
<220> FEATURE:
<221> NAME/KEY: CDS
<222> LOCATION: (121)..(837)

<400> SEQUENCE: 8

```
agatgcacga tcgagtaggc cggataaggc gtttacgccg catccagcat ggaaaacgcg     60
cactttgtta tcaatctggg gccagcaaat gctggcctga tttgttcttg agggaagact    120 atg atg cgc aaa atg ctg ctg gcg gca gca ctt tca gtg acg gca atg    168
Met Met Arg Lys Met Leu Leu Ala Ala Ala Leu Ser Val Thr Ala Met
  1               5                  10                  15 acc gct cac gcc gac tac cag tgc agc gtc acg ccg cgt gac gat gtg    216
Thr Ala His Ala Asp Tyr Gln Cys Ser Val Thr Pro Arg Asp Asp Val
                 20                  25                  30 att gtc agc ccg caa acc gtg cag gtg aag ggc gaa aac ggc aat ctg    264
Ile Val Ser Pro Gln Thr Val Gln Val Lys Gly Glu Asn Gly Asn Leu
         35                  40                  45 gtg atc acg cca gac ggc aac gtg atg tat aac ggt aag caa tat tcc    312
Val Ile Thr Pro Asp Gly Asn Val Met Tyr Asn Gly Lys Gln Tyr Ser
 50                  55                  60 ctg aat gcc gcc cag cgc gag cag gcg aag gat tat cag gct gaa cta    360
Leu Asn Ala Ala Gln Arg Glu Gln Ala Lys Asp Tyr Gln Ala Glu Leu
 65                  70                  75                  80 cgt agc acc ctg ccg tgg att gat gga ggc gcg aaa agc cgc gtc gag    408
Arg Ser Thr Leu Pro Trp Ile Asp Gly Gly Ala Lys Ser Arg Val Glu
                 85                  90                  95 aaa gct cgt att gcg ctg gat aaa att atc gtt cag gag atg ggc gaa    456
Lys Ala Arg Ile Ala Leu Asp Lys Ile Ile Val Gln Glu Met Gly Glu
                100                 105                 110 agc agc aaa atg cgc agc cgt ctg acc aaa ctt gat gcg cag ctg aaa    504
Ser Ser Lys Met Arg Ser Arg Leu Thr Lys Leu Asp Ala Gln Leu Lys
            115                 120                 125 gag cag atg aac cgc att atc gaa acg cgc agc gat ggc ctg acg ttt    552
Glu Gln Met Asn Arg Ile Ile Glu Thr Arg Ser Asp Gly Leu Thr Phe
        130                 135                 140 cac tat aaa gcc att gat cag gtt cgt gcc gaa ggc cag caa tta gtg    600
His Tyr Lys Ala Ile Asp Gln Val Arg Ala Glu Gly Gln Gln Leu Val
145                 150                 155                 160 aat cag gca atg ggc gga att tta cag gac agc att aat gaa atg ggc    648
Asn Gln Ala Met Gly Gly Ile Leu Gln Asp Ser Ile Asn Glu Met Gly
                165                 170                 175 gcg aaa gcg gtg ctg aaa agc ggc ggt aac cca tta cag aac gtg ctg    696
Ala Lys Ala Val Leu Lys Ser Gly Gly Asn Pro Leu Gln Asn Val Leu
            180                 185                 190 gga agc ctg ggc ggc ctg caa tcc tca atc caa acc gag tgg aaa aag    744
Gly Ser Leu Gly Gly Leu Gln Ser Ser Ile Gln Thr Glu Trp Lys Lys
        195                 200                 205
```

```
cag gaa aaa gat ttc cag cag ttt ggc aaa gat gtt tgt agc cgc gtt    792
Gln Glu Lys Asp Phe Gln Gln Phe Gly Lys Asp Val Cys Ser Arg Val
    210             215                 220 gtg act ctg gaa gat agc cgc aaa gcc ctg gtc ggg aat tta aaa        837
Val Thr Leu Glu Asp Ser Arg Lys Ala Leu Val Gly Asn Leu Lys
225             230                 235 taatcctcta tttaagacg gcataatact tttttatgcc gtttaattct tcgttttgtt   897
acctgcctct aactttgtaa gggcgaattc tgcagatatc catcacactg gcggccgctc  957
gagcatgcat ctagagggcc caattcgccc tatagtgagt cgtattacaa ttcactggcc  1017
gtcgttttac aaccgtcgtg actgggaaaa ccctggcgtt acccaactta atcgccttgc  1077
agcacatccc cctttcgcca gctggcgtaa tagcgaaaag gcccgcaccg atcgccttc   1137 caacagttgc gcacctgatg gccaatggac gcgcctg                          1174
```

<210> SEQ ID NO 9
<211> LENGTH: 239
<212> TYPE: PRT
<213> ORGANISM: Escherichia coli

<400> SEQUENCE: 9

```
Met Met Arg Lys Met Leu Leu Ala Ala Leu Ser Val Thr Ala Met
 1               5                  10                  15

Thr Ala His Ala Asp Tyr Gln Cys Ser Val Thr Pro Arg Asp Val
             20                  25                  30

Ile Val Ser Pro Gln Thr Val Gln Val Lys Gly Glu Asn Gly Asn Leu
         35                  40                  45

Val Ile Thr Pro Asp Gly Asn Val Met Tyr Asn Gly Lys Gln Tyr Ser
     50                  55                  60

Leu Asn Ala Ala Gln Arg Glu Gln Ala Lys Asp Tyr Gln Ala Glu Leu
 65                  70                  75                  80

Arg Ser Thr Leu Pro Trp Ile Asp Gly Ala Lys Ser Arg Val Glu
                 85                  90                  95

Lys Ala Arg Ile Ala Leu Asp Lys Ile Ile Val Gln Glu Met Gly Glu
            100                 105                 110

Ser Ser Lys Met Arg Ser Arg Leu Thr Lys Leu Asp Ala Gln Leu Lys
        115                 120                 125

Glu Gln Met Asn Arg Ile Ile Glu Thr Arg Ser Asp Gly Leu Thr Phe
    130                 135                 140

His Tyr Lys Ala Ile Asp Gln Val Arg Ala Glu Gly Gln Gln Leu Val
145                 150                 155                 160

Asn Gln Ala Met Gly Gly Ile Leu Gln Asp Ser Ile Asn Glu Met Gly
                165                 170                 175

Ala Lys Ala Val Leu Lys Ser Gly Gly Asn Pro Leu Gln Asn Val Leu
            180                 185                 190

Gly Ser Leu Gly Gly Leu Gln Ser Ser Ile Gln Thr Glu Trp Lys Lys
        195                 200                 205

Gln Glu Lys Asp Phe Gln Gln Phe Gly Lys Asp Val Cys Ser Arg Val
    210                 215                 220

Val Thr Leu Glu Asp Ser Arg Lys Ala Leu Val Gly Asn Leu Lys
225                 230                 235
```

<210> SEQ ID NO 10
<211> LENGTH: 3406
<212> TYPE: DNA
<213> ORGANISM: Escherichia coli

```
<220> FEATURE:
<221> NAME/KEY: CDS
<222> LOCATION: (1007)..(1276)
<221> NAME/KEY: CDS
<222> LOCATION: (1280)..(1792)
<221> NAME/KEY: CDS
<222> LOCATION: (1798)..(2574)
<221> NAME/KEY: CDS
<222> LOCATION: (2604)..(3398)

<400> SEQUENCE: 10
gatgatggtg atggagcgta tttacggcat tccggtgtct gatgttgcga cgctggagaa      60
aaacggcacc aacatgaaat tgctggcgga acgcggcgtg caggtgttct tcactcaggt     120 cttttcgcgac agcttttttcc atgctgatat gcaccctggc aacatcttcg taagctatga   180
acacccggaa aacccgaaat atatcggcat tgattgcggg attgttggct cgctaaacaa     240
agaagataaa cgctatctgg cggaaaactt tatcgccttc tttaatcgcg actatcgcaa     300
agtggcagag ctacacgtcg attctggttg ggtgccacca gataccaacg ttgaagagtt     360
cgaatttgcc attcgtacgg tctgtgaacc tatctttgag aaaccgctgg ccgaaatttc     420
gtttggacat gtactgttaa atctgtttaa tacggcgcgt cgcttcaata tggaagtgca     480
gccgcaactg gtgttactcc agaaaaccct gctctacgtc gaagggtag acgccagct       540 ttatccgcaa ctcgatttat ggaaaacggc gaagcctttc ctggagtcgt ggattaaaga    600
tcaggtcggt attcctgcgc tggtgagagc atttaaagaa aaagcgccgt tctgggtcga    660
aaaaatgcca gaactgcctg aactggttta cgacagtttg cgccagggca agtatttaca    720
gcatagtgtt ggtaagattg cccgcgagct tcagtcaaat catgtacgtc agggacaatt    780
cgcgttattt tctcggaatt ggcgctacgt tagtatttaa gtggcacatt cttgttggtc    840
agccgacctg aatgggggct gatgcccggc tggttaatgg caggtggtct gatcgcctgg    900
tttgtccggt tggcgcaaaa cacgctgatt ttttcatcgc tcaaggcggg ccgtgtaacg    960
tataatgcgg cttttgtttaa tcatcatcta ccacagagga acatgt atg ggt ggt     1015
                                                     Met Gly Gly
                                                      1 atc agt att tgg cag tta ttg att att gcc gtc atc gtt gta ctg ctt     1063
Ile Ser Ile Trp Gln Leu Leu Ile Ile Ala Val Ile Val Val Leu Leu
    5               10                  15 ttt ggc acc aaa aag ctc ggc tcc atc ggt tcc gat ctt ggt gcg tcg     1111
Phe Gly Thr Lys Lys Leu Gly Ser Ile Gly Ser Asp Leu Gly Ala Ser
20                  25                  30                  35 atc aaa ggc ttt aaa aaa gca atg agc gat gat gaa cca aag cag gat     1159
Ile Lys Gly Phe Lys Lys Ala Met Ser Asp Asp Glu Pro Lys Gln Asp
                40                  45                  50 aaa acc agc cag gat gct gat ttt act gcg aaa act atc gcc gat aag    1207
Lys Thr Ser Gln Asp Ala Asp Phe Thr Ala Lys Thr Ile Ala Asp Lys
            55                  60                  65 cag gcg gat acg aat cag gaa cag gct aaa ata gaa gac gcg aag cgc    1255
Gln Ala Asp Thr Asn Gln Glu Gln Ala Lys Ile Glu Asp Ala Lys Arg
        70                  75                  80 cac gat aaa gag cag gtg taa tct gtg ttt gat atc ggt ttt agc gaa    1303
His Asp Lys Glu Gln Val         Val Phe Asp Ile Gly Phe Ser Glu
    85                  90                  95 ctg cta ttg gtg ttc atc atc ggc ctc gtc gtt ctg ggg cca caa cga    1351
Leu Leu Leu Val Phe Ile Ile Gly Leu Val Val Leu Gly Pro Gln Arg
100                 105                 110 ctg cct gtg gcg gta aaa acg gta gcg ggc tgg att cgc gcg ttg cgt    1399
Leu Pro Val Ala Val Lys Thr Val Ala Gly Trp Ile Arg Ala Leu Arg
115                 120                 125                 130
```

```
                                                       -continued tca ctg gcg aca acg gtg cag aac gaa ctg acc cag gag tta aaa ctc    1447
Ser Leu Ala Thr Thr Val Gln Asn Glu Leu Thr Gln Glu Leu Lys Leu
                135                 140                 145 cag gag ttt cag gac agt ctg aaa aag gtt gaa aag gcg agc ctc act    1495
Gln Glu Phe Gln Asp Ser Leu Lys Lys Val Glu Lys Ala Ser Leu Thr
        150                 155                 160 aac ctg acg ccc gaa ctg aaa gcg tcg atg gat gaa tta cgc cag gct    1543
Asn Leu Thr Pro Glu Leu Lys Ala Ser Met Asp Glu Leu Arg Gln Ala
            165                 170                 175 gcg gag tcg atg aaa cgt tcc tac gtt gca aac gat cct gaa aag gcg    1591
Ala Glu Ser Met Lys Arg Ser Tyr Val Ala Asn Asp Pro Glu Lys Ala
180                 185                 190 agc gat gaa gcg cac acc atc cat aac ccg gtg gtg aaa gac aat gaa    1639
Ser Asp Glu Ala His Thr Ile His Asn Pro Val Val Lys Asp Asn Glu
195                 200                 205                 210 act gcg cat gaa ggc gta acg cct gct gct gca caa acg cag gcc agt    1687
Thr Ala His Glu Gly Val Thr Pro Ala Ala Ala Gln Thr Gln Ala Ser
                215                 220                 225 tcg ccg gaa cag aag cca gaa acc acg cca gag ccg gtg gta aaa cct    1735
Ser Pro Glu Gln Lys Pro Glu Thr Thr Pro Glu Pro Val Val Lys Pro
        230                 235                 240 gct gcg gac gct gaa ccg aaa acc gct gca cct tcc cct tcg tcg agt    1783
Ala Ala Asp Ala Glu Pro Lys Thr Ala Ala Pro Ser Pro Ser Ser Ser
            245                 250                 255 gat aaa ccg taaac atg tct gta gaa gat act caa ccg ctt atc acg cat    1833
Asp Lys Pro       Met Ser Val Glu Asp Thr Gln Pro Leu Ile Thr His
        260             265                 270 ctg att gag ctg cgt aag cgt ctg ctg aac tgc att atc tcg gtg atc    1881
Leu Ile Glu Leu Arg Lys Arg Leu Leu Asn Cys Ile Ile Ser Val Ile
275                 280                 285 gtg ata ttc ctg tgt ctg gtc tat ttc gcc aat gac atc tat cac ctg    1929
Val Ile Phe Leu Cys Leu Val Tyr Phe Ala Asn Asp Ile Tyr His Leu
290                 295                 300                 305 gta tcc gcg cca ctg atc aag cag ttg ccg caa ggt tca acg atg atc    1977
Val Ser Ala Pro Leu Ile Lys Gln Leu Pro Gln Gly Ser Thr Met Ile
                310                 315                 320 gcc acc gac gtg gcc tcg ccg ttc ttt acg ccg atc aag ctg acc ttt    2025
Ala Thr Asp Val Ala Ser Pro Phe Phe Thr Pro Ile Lys Leu Thr Phe
            325                 330                 335 atg gtg tcg ctg att ctg tca gcg ccg gtg att ctc tat cag gtg tgg    2073
Met Val Ser Leu Ile Leu Ser Ala Pro Val Ile Leu Tyr Gln Val Trp
                340                 345                 350 gcg ttt atc gcc cca gcg ctg tat aag cat gaa cgt cgc ctg gtg gtg    2121
Ala Phe Ile Ala Pro Ala Leu Tyr Lys His Glu Arg Arg Leu Val Val
        355                 360                 365 ccg ctg ctg gtt tcc agc tct ctg ctg ttt tat atc ggc atg gcg ttc    2169
Pro Leu Leu Val Ser Ser Ser Leu Leu Phe Tyr Ile Gly Met Ala Phe
370                 375                 380                 385 gcc tac ttt gtg gtc ttt ccg ctg gca ttt ggc ttc ctt gcc aat acc    2217
Ala Tyr Phe Val Val Phe Pro Leu Ala Phe Gly Phe Leu Ala Asn Thr
                390                 395                 400 gcg ccg gaa ggg gta cag gta tcc acc gac atc gcg agc tat tta agc    2265
Ala Pro Glu Gly Val Gln Val Ser Thr Asp Ile Ala Ser Tyr Leu Ser
            405                 410                 415 ttc gtt atg gcg ctg ttt atg gcg ttt ggt gtc tcc ttt gaa gtg ccg    2313
Phe Val Met Ala Leu Phe Met Ala Phe Gly Val Ser Phe Glu Val Pro
        420                 425                 430 gtg gca att gtg ctg ctg tgc tgg atg ggg att acc tcg cca gaa gac    2361
Val Ala Ile Val Leu Leu Cys Trp Met Gly Ile Thr Ser Pro Glu Asp
```

-continued

| | | | |
|---|---|---|---|
| | 435 | 440 | 445 |
| tta cgc aaa aaa cgc ccg tat gtg ctg gtt ggt gca ttc gtt gtc ggg<br>Leu Arg Lys Lys Arg Pro Tyr Val Leu Val Gly Ala Phe Val Val Gly<br>450                 455                460              465 | | | 2409 |
| atg ttg ctg acg ccg ccg gat gtc ttc tcg caa acg ctg ttg gcg atc<br>Met Leu Leu Thr Pro Pro Asp Val Phe Ser Gln Thr Leu Leu Ala Ile<br>            470                475               480 | | | 2457 |
| cct atg tac tgc ctg ttt gaa atc ggt gtc ttc ttc tca cgc ttt tac<br>Pro Met Tyr Cys Leu Phe Glu Ile Gly Val Phe Phe Ser Arg Phe Tyr<br>               485              490               495 | | | 2505 |
| gtt ggt aaa ggg cga aac cgg gaa gag gaa aac gac gct gaa gca gaa<br>Val Gly Lys Gly Arg Asn Arg Glu Glu Glu Asn Asp Ala Glu Ala Glu<br>        500                505              510 | | | 2553 |
| agc gaa aaa act gaa gaa taa attcaaccgc ccgtcagggc ggttgtcat atg<br>Ser Glu Lys Thr Glu Glu                                        Met<br>515                520 | | | 2606 |
| gag tac agg atg ttt gat atc ggc gtt aat ttg acc agt tcg caa ttt<br>Glu Tyr Arg Met Phe Asp Ile Gly Val Asn Leu Thr Ser Ser Gln Phe<br>                525              530              535 | | | 2654 |
| gcg aaa gac cgt gat gat gtt gta gcg cgc gct ttt gac gcg gga gtt<br>Ala Lys Asp Arg Asp Asp Val Val Ala Arg Ala Phe Asp Ala Gly Val<br>            540               545              550 | | | 2702 |
| aat ggg cta ctc atc acc ggt acc aat ctg cgt gaa agc cag cag gcg<br>Asn Gly Leu Leu Ile Thr Gly Thr Asn Leu Arg Glu Ser Gln Gln Ala<br>555                 560               565 | | | 2750 |
| caa aag ctg gcg cgt cag tat tcg tcc tgt tgg tca acg gcg ggc gta<br>Gln Lys Leu Ala Arg Gln Tyr Ser Ser Cys Trp Ser Thr Ala Gly Val<br>570                 575              580              585 | | | 2798 |
| cat cct cac gac agc agc cag tgg caa gct gtg act gaa gaa gcg att<br>His Pro His Asp Ser Ser Gln Trp Gln Ala Val Thr Glu Glu Ala Ile<br>              590              595              600 | | | 2846 |
| att gag ctg gcc gcg cag cca gaa gtg gtg gcg att ggt gaa tgt ggt<br>Ile Glu Leu Ala Ala Gln Pro Glu Val Val Ala Ile Gly Glu Cys Gly<br>            605              610              615 | | | 2894 |
| ctc gac ttt aac cgc aac ttt tcg acg ccg gaa gag cag gaa cgc gct<br>Leu Asp Phe Asn Arg Asn Phe Ser Thr Pro Glu Glu Gln Glu Arg Ala<br>          620              625              630 | | | 2942 |
| ttt gtt gcc cag cta cgc att gcc gca gaa tta aac atg ccg gta ttt<br>Phe Val Ala Gln Leu Arg Ile Ala Ala Glu Leu Asn Met Pro Val Phe<br>            635              640              645 | | | 2990 |
| atg cac tgt cgc gat gcc cac gag cgg ttt atg aca ttg ctg gag ccg<br>Met His Cys Arg Asp Ala His Glu Arg Phe Met Thr Leu Leu Glu Pro<br>650                655              660              665 | | | 3038 |
| tgg ctg gat aaa ctg cct ggt gcg gtt ctt cat tgc ttt acc ggc aca<br>Trp Leu Asp Lys Leu Pro Gly Ala Val Leu His Cys Phe Thr Gly Thr<br>               670              675              680 | | | 3086 |
| cgc gaa gag atg cag gcg tgc gtg gcg tgt gga att tat atc ggc att<br>Arg Glu Glu Met Gln Ala Cys Val Ala Cys Gly Ile Tyr Ile Gly Ile<br>              685              690              695 | | | 3134 |
| acc ggt tgg gtt tgc gat gaa cga cgc ggg ctg gag ctg cgg gaa ttg<br>Thr Gly Trp Val Cys Asp Glu Arg Arg Gly Leu Glu Leu Arg Glu Leu<br>            700              705              710 | | | 3182 |
| ttg ccg ttg att ccg gcg gag aaa ttg ctg atc gaa act gat gcg ccg<br>Leu Pro Leu Ile Pro Ala Glu Lys Leu Leu Ile Glu Thr Asp Ala Pro<br>715                 720              725 | | | 3230 |
| tat ctg ctc cct cgc gat ctc acg cca aag cca tca tcc cgg cgc aac<br>Tyr Leu Leu Pro Arg Asp Leu Thr Pro Lys Pro Ser Ser Arg Arg Asn<br>730                 735               740              745 | | | 3278 |
| gag cca gcc cat ctg ccc cat att ttg caa cgt att gcg cac tgg cgt<br>Glu Pro Ala His Leu Pro His Ile Leu Gln Arg Ile Ala His Trp Arg | | | 3326 |

```
                750             755             760
gga gaa gat gcc gca tgg ctg gct gcc acc acg gat gcc aat gtc aaa    3374
Gly Glu Asp Ala Ala Trp Leu Ala Ala Thr Thr Asp Ala Asn Val Lys
            765             770             775 aca ctg ttt ggg att gcg ttt tag agtttgcg                            3406
Thr Leu Phe Gly Ile Ala Phe
            780             785
```

<210> SEQ ID NO 11
<211> LENGTH: 89
<212> TYPE: PRT
<213> ORGANISM: Escherichia coli

<400> SEQUENCE: 11

```
Met Gly Gly Ile Ser Ile Trp Gln Leu Leu Ile Ile Ala Val Ile Val
 1               5                  10                  15

Val Leu Leu Phe Gly Thr Lys Lys Leu Gly Ser Ile Gly Ser Asp Leu
            20                  25                  30

Gly Ala Ser Ile Lys Gly Phe Lys Lys Ala Met Ser Asp Asp Glu Pro
        35                  40                  45

Lys Gln Asp Lys Thr Ser Gln Asp Ala Asp Phe Thr Ala Lys Thr Ile
    50                  55                  60

Ala Asp Lys Gln Ala Asp Thr Asn Gln Glu Gln Ala Lys Ile Glu Asp
65                  70                  75                  80

Ala Lys Arg His Asp Lys Glu Gln Val
                85
```

<210> SEQ ID NO 12
<211> LENGTH: 171
<212> TYPE: PRT
<213> ORGANISM: Escherichia coli

<400> SEQUENCE: 12

```
Val Phe Asp Ile Gly Phe Ser Glu Leu Leu Leu Val Phe Ile Ile Gly
 1               5                  10                  15

Leu Val Val Leu Gly Pro Gln Arg Leu Pro Val Ala Val Lys Thr Val
            20                  25                  30

Ala Gly Trp Ile Arg Ala Leu Arg Ser Leu Ala Thr Thr Val Gln Asn
        35                  40                  45

Glu Leu Thr Gln Glu Leu Lys Leu Gln Glu Phe Gln Asp Ser Leu Lys
    50                  55                  60

Lys Val Glu Lys Ala Ser Leu Thr Asn Leu Thr Pro Glu Leu Lys Ala
65                  70                  75                  80

Ser Met Asp Glu Leu Arg Gln Ala Ala Glu Ser Met Lys Arg Ser Tyr
                85                  90                  95

Val Ala Asn Asp Pro Glu Lys Ala Ser Asp Glu Ala His Thr Ile His
            100                 105                 110

Asn Pro Val Val Lys Asp Asn Glu Thr Ala His Glu Gly Val Thr Pro
        115                 120                 125

Ala Ala Ala Gln Thr Gln Ala Ser Ser Pro Glu Gln Lys Pro Glu Thr
    130                 135                 140

Thr Pro Glu Pro Val Val Lys Pro Ala Ala Asp Ala Glu Pro Lys Thr
145                 150                 155                 160

Ala Ala Pro Ser Pro Ser Ser Ser Asp Lys Pro
                165                 170
```

<210> SEQ ID NO 13

```
<211> LENGTH: 258
<212> TYPE: PRT
<213> ORGANISM: Escherichia coli

<400> SEQUENCE: 13

Met Ser Val Glu Asp Thr Gln Pro Leu Ile Thr His Leu Ile Glu Leu
 1               5                  10                  15

Arg Lys Arg Leu Leu Asn Cys Ile Ile Ser Val Ile Val Ile Phe Leu
            20                  25                  30

Cys Leu Val Tyr Phe Ala Asn Asp Ile Tyr His Leu Val Ser Ala Pro
        35                  40                  45

Leu Ile Lys Gln Leu Pro Gln Gly Ser Thr Met Ile Ala Thr Asp Val
    50                  55                  60

Ala Ser Pro Phe Phe Thr Pro Ile Lys Leu Thr Phe Met Val Ser Leu
65                  70                  75                  80

Ile Leu Ser Ala Pro Val Ile Leu Tyr Gln Val Trp Ala Phe Ile Ala
                85                  90                  95

Pro Ala Leu Tyr Lys His Glu Arg Arg Leu Val Pro Leu Leu Val
            100                 105                 110

Ser Ser Ser Leu Leu Phe Tyr Ile Gly Met Ala Phe Ala Tyr Phe Val
        115                 120                 125

Val Phe Pro Leu Ala Phe Gly Phe Leu Ala Asn Thr Ala Pro Glu Gly
    130                 135                 140

Val Gln Val Ser Thr Asp Ile Ala Ser Tyr Leu Ser Phe Val Met Ala
145                 150                 155                 160

Leu Phe Met Ala Phe Gly Val Ser Phe Glu Val Pro Val Ala Ile Val
                165                 170                 175

Leu Leu Cys Trp Met Gly Ile Thr Ser Pro Glu Asp Leu Arg Lys Lys
            180                 185                 190

Arg Pro Tyr Val Leu Val Gly Ala Phe Val Val Gly Met Leu Leu Thr
        195                 200                 205

Pro Pro Asp Val Phe Ser Gln Thr Leu Leu Ala Ile Pro Met Tyr Cys
    210                 215                 220

Leu Phe Glu Ile Gly Val Phe Phe Ser Arg Phe Tyr Val Gly Lys Gly
225                 230                 235                 240

Arg Asn Arg Glu Glu Glu Asn Asp Ala Glu Ala Glu Ser Glu Lys Thr
                245                 250                 255

Glu Glu

<210> SEQ ID NO 14
<211> LENGTH: 264
<212> TYPE: PRT
<213> ORGANISM: Escherichia coli

<400> SEQUENCE: 14

Met Glu Tyr Arg Met Phe Asp Ile Gly Val Asn Leu Thr Ser Ser Gln
 1               5                  10                  15

Phe Ala Lys Asp Arg Asp Asp Val Val Ala Arg Ala Phe Asp Ala Gly
            20                  25                  30

Val Asn Gly Leu Leu Ile Thr Gly Thr Asn Leu Arg Glu Ser Gln Gln
        35                  40                  45

Ala Gln Lys Leu Ala Arg Gln Tyr Ser Ser Cys Trp Ser Thr Ala Gly
    50                  55                  60

Val His Pro His Asp Ser Ser Gln Trp Gln Ala Val Thr Glu Glu Ala
65                  70                  75                  80
```

```
Ile Ile Glu Leu Ala Ala Gln Pro Glu Val Ala Ile Gly Glu Cys
             85                  90                  95

Gly Leu Asp Phe Asn Arg Asn Phe Ser Thr Pro Glu Gln Glu Arg
                100                 105                 110

Ala Phe Val Ala Gln Leu Arg Ile Ala Ala Glu Leu Asn Met Pro Val
                115                 120                 125

Phe Met His Cys Arg Asp Ala His Glu Arg Phe Met Thr Leu Leu Glu
        130                 135                 140

Pro Trp Leu Asp Lys Leu Pro Gly Ala Val Leu His Cys Phe Thr Gly
145                 150                 155                 160

Thr Arg Glu Glu Met Gln Ala Cys Val Ala Cys Gly Ile Tyr Ile Gly
                    165                 170                 175

Ile Thr Gly Trp Val Cys Asp Glu Arg Arg Gly Leu Glu Leu Arg Glu
                180                 185                 190

Leu Leu Pro Leu Ile Pro Ala Glu Lys Leu Leu Ile Glu Thr Asp Ala
            195                 200                 205

Pro Tyr Leu Leu Pro Arg Asp Leu Thr Pro Lys Pro Ser Ser Arg Arg
    210                 215                 220

Asn Glu Pro Ala His Leu Pro His Ile Leu Gln Arg Ile Ala His Trp
225                 230                 235                 240

Arg Gly Glu Asp Ala Ala Trp Leu Ala Ala Thr Thr Asp Ala Asn Val
                245                 250                 255

Lys Thr Leu Phe Gly Ile Ala Phe
                260
```

<210> SEQ ID NO 15
<211> LENGTH: 586
<212> TYPE: DNA
<213> ORGANISM: Escherichia coli
<220> FEATURE:
<221> NAME/KEY: CDS
<222> LOCATION: (170)..(370)

<400> SEQUENCE: 15

```
tcttaaacaa ccgtcgcttt gcgccgccgc aattattatg atgttttttt actcggcgct      60
tgattcacct tgttacagat tgctattgtg tgcgcgcgtc gaatgaccgt taatattctc     120 tggttttttaa ggcgcgttct gttgccggtt atatgtcaag aaggtatct atg ggt gag    178
                                                       Met Gly Glu
                                                         1 att agt att acc aaa ctg ctg gta gtt gcg gcg ctg gtc gtt ctg ctg       226
Ile Ser Ile Thr Lys Leu Leu Val Val Ala Ala Leu Val Val Leu Leu
  5                  10                  15 ttt ggg act aag aag tta cgt acg ctg ggc gga gac ctt gga gcg gcc       274
Phe Gly Thr Lys Lys Leu Arg Thr Leu Gly Gly Asp Leu Gly Ala Ala
 20                  25                  30                  35 att aaa ggg ttc aag aag gcg atg aat gat gac gat gct gcg gcg aaa       322
Ile Lys Gly Phe Lys Lys Ala Met Asn Asp Asp Asp Ala Ala Ala Lys
                 40                  45                  50 aaa ggc gca gac gtt gat ctt cag gct gaa aag ctc tct cat aaa gag       370
Lys Gly Ala Asp Val Asp Leu Gln Ala Glu Lys Leu Ser His Lys Glu
             55                  60                  65 tgacgtggcg agcaggacgc tccctcaata tcttgttcga tacaaaaacc cgcttcaaaa     430
agcgggtttt ttatcagaca gatgtaagta attattacag gattacttaa cttccatccc     490
tttcgcctgc aaatcggcgt ggtaagaaga gcggacaaac ggaccgcatg cagcatgggt     550
aaagcccatc gccagcgctt cgctttcatt tcgtcg                              586
```

-continued

<210> SEQ ID NO 16
<211> LENGTH: 67
<212> TYPE: PRT
<213> ORGANISM: Escherichia coli

<400> SEQUENCE: 16

Met Gly Glu Ile Ser Ile Thr Lys Leu Leu Val Val Ala Ala Leu Val
 1               5                  10                  15

Val Leu Leu Phe Gly Thr Lys Lys Leu Arg Thr Leu Gly Gly Asp Leu
            20                  25                  30

Gly Ala Ala Ile Lys Gly Phe Lys Lys Ala Met Asn Asp Asp Asp Ala
        35                  40                  45

Ala Ala Lys Lys Gly Ala Asp Val Asp Leu Gln Ala Glu Lys Leu Ser
    50                  55                  60

His Lys Glu
 65

<210> SEQ ID NO 17
<211> LENGTH: 4200
<212> TYPE: DNA
<213> ORGANISM: Salmonella typhimurium
<220> FEATURE:
<221> NAME/KEY: CDS
<222> LOCATION: (947)..(1444)
<221> NAME/KEY: CDS
<222> LOCATION: (1450)..(1722)

<400> SEQUENCE: 17
cgcaagtcaa tgtcgtcccg gtcgtatgta aaagtatgtg aataggggcgg gcgaaagcgg        60 ctaacaaaga ggcagcgtga aggataatgt gtataatgcg ccctaataa ttcatcatct        120 atcacagagg aacatgtatg ggtggtatca gtatttggca gttgttgatt gttgccgtta       180
tcgtcgtact gctgttcggc accaaaaaac tcggttccat cggttccgat cttggcgcgt       240
ctatcaaagg cttttaaaaag gccatgagcg atgatgatgc caaacaggat aaaaccagtc       300
aggacgctga ttttaccgct aaatctatcg cggataagca aggcgaagcg aaaaaggaag       360
acgctaaaag ccaagataaa gagcaggtat aatccgtgtt tgatatcggt tttagcgaac       420
tgctgttagt gttcgttatc ggcctcattg tgttggggcc gcaacgattg ccagtagcgg       480
taaaaacggt agcgggctgg attcgcgcgt tgcggtccct tgcgacaacg gttcagaatg       540
aactgactca ggaactgaaa cttcaggagt tccaggacag tctgaaaaaa gtcgaaaagg       600
cgagcctgga aaatctgact cccgaactga agcatctat ggatgaactg cgtcaggcgg       660
cggagtcgat gaaacgcacc tacagcgcta cgatcccga caagcgagc gatgaagcgc       720 ataccatcca taatccggtg gtaaaaggga acgaaacgca gcatgagggc gtcacccctg       780
ccgccgctga aacacaggcg agcgcgccgg aacaaaagcc ggagcccgtt aaagctaacg       840
tgcctgagtc gacggaaacc gcttccgtag ccacgataga cgccgagaag aaatccgctg       900
cgcctgttgt cgaatcttcc ccctcgtcga gtgataaacc gtaaac atg gct gta       955
                                                    Met Ala Val
                                                     1 gaa gat act caa ccg ctt atc acg cat ctg atc gag ttg cgt aag cgc      1003
Glu Asp Thr Gln Pro Leu Ile Thr His Leu Ile Glu Leu Arg Lys Arg
      5                  10                  15 ctg cta aac tgc atc gtc gca gta ctt ctg att ttt ctg gcg tta att      1051
Leu Leu Asn Cys Ile Val Ala Val Leu Leu Ile Phe Leu Ala Leu Ile
 20                  25                  30                  35 tat ttc gcc aat gat att tat cat tta gtc gcc gca ccg ctg att aaa      1099

-continued

```
                Tyr Phe Ala Asn Asp Ile Tyr His Leu Val Ala Ala Pro Leu Ile Lys
                                40                  45                  50 cag atg ccg caa ggg gcg aca atg att gcg acg gat gtg gcg tcg ccg          1147
Gln Met Pro Gln Gly Ala Thr Met Ile Ala Thr Asp Val Ala Ser Pro
                55                  60                  65 ttt ttt acg cct atc aaa ctc acc ttc atg gtg tct ttg atc tta tcc          1195
Phe Phe Thr Pro Ile Lys Leu Thr Phe Met Val Ser Leu Ile Leu Ser
        70                  75                  80 gcg cct gtc att ttg tac cag gtt tgg gcc ttt atc gcc ccg gcg ctg          1243
Ala Pro Val Ile Leu Tyr Gln Val Trp Ala Phe Ile Ala Pro Ala Leu
    85                  90                  95 tat aag cat gag cgt cgt ctg gtc gta cct ctg ctg gta tcc agc tcg          1291
Tyr Lys His Glu Arg Arg Leu Val Val Pro Leu Leu Val Ser Ser Ser
100                 105                 110                 115 ctg ctt ttc tat att ggt atg gcc ttc gcc tat ttt gtc gta ttc cct          1339
Leu Leu Phe Tyr Ile Gly Met Ala Phe Ala Tyr Phe Val Val Phe Pro
                120                 125                 130 ttg gcc ttt ggt ttc ctg acg cat acg gcg ccg gaa ggg gta cag gtt          1387
Leu Ala Phe Gly Phe Leu Thr His Thr Ala Pro Glu Gly Val Gln Val
            135                 140                 145 tcg aca gat atc gcc agc tat ctt agc ttt gtc atg gcg ctt ttt atg          1435
Ser Thr Asp Ile Ala Ser Tyr Leu Ser Phe Val Met Ala Leu Phe Met
        150                 155                 160 gcc ttt gcg tagcc ttt gaa gtg ccg gtg gcg att gtg ttg ctg tgc tgg        1485
Ala Phe Ala     Phe Glu Val Pro Val Ala Ile Val Leu Leu Cys Trp
    165                 170                 175 atg ggc atc acc acg cca gaa gat ttg cgt aaa aaa cgg cct tat atc          1533
Met Gly Ile Thr Thr Pro Glu Asp Leu Arg Lys Lys Arg Pro Tyr Ile
180                 185                 190 ctg gtc ggg gca ttc att gtg gga atg ctg ctt acg ccg cca gat gtt          1581
Leu Val Gly Ala Phe Ile Val Gly Met Leu Leu Thr Pro Pro Asp Val
                195                 200                 205                 210 ttc tcg caa acg ttg ctg gcg ata ccg atg tac tgc ctg ttt gaa att          1629
Phe Ser Gln Thr Leu Leu Ala Ile Pro Met Tyr Cys Leu Phe Glu Ile
            215                 220                 225 ggc gtt ttc tgc tca cgc ttt tat gtc ggt aag cga cgg acg cgc gac          1677
Gly Val Phe Cys Ser Arg Phe Tyr Val Gly Lys Arg Arg Thr Arg Asp
        230                 235                 240 gaa gat aac gag gcc gaa acc gaa aag gcc gag cac act gaa gac              1722
Glu Asp Asn Glu Ala Glu Thr Glu Lys Ala Glu His Thr Glu Asp
    245                 250                 255 taaacacaac cgcccgccag ggcggttgtc atatgggggc aagcatgttt gatattggcg        1782
ttaatttaac cagtagccag tttgcaaaag atcgtgatga tgtggtcgcc cgtgcgtttg        1842
cggcgggagt aaaggtatg ctactgaccg gaacgaacat ccatgaaagt cagcaggcgt         1902
taaaactggc gcggcgctac ccccattgtt ggtcgacggc tggcgtccat ccccatgaca        1962
gcagtcagtg gtcacccgcg tctgaagacg ccattattgc gctggcgaac cagccggaag       2022
tcgtcgctat cggtgagtgc gggctggatt tcaatcgcaa ttttccacg ccgcaggagc        2082 aggagcgtgc ctttcaggcg cagctacaaa ttgccgccga attgcagata ccaatctttta      2142 tgcactgccg ggacgcgcat gagcgatttc tggtattgct tgatccctgg ctggatagtc       2202
ttcctggtgc aatactgcac tgctttaccg gttcacgcca gcaaatgcag gcctgtgtgg       2262
atagagggct ctatatcggt attaccgggt gggtttgcga cgaacgacgc gggcttgagc       2322
tacgtgaact cttaccgttt attccagcgg aaaagctact gatagaaacc gacgcgccgt       2382
atctgttgcc tcgcgatctt acgccgaaac caacgtcacg acgcaacgag cccgcgtatc       2442
```

-continued

```
tgcctcacat cctggagcgc atagcgctat ggcgtggtga agatccgcaa tggttagcgg    2502
cgatgacaga tgccaacgcc agaaccttat ttgaggttgt attctgaacg atcgctaaat    2562
cttgcgaaaa ccggtgtttt ttacgctctg cttcacttct ttattgagta aattaagcag    2622
taacatcgaa cgcgtttcgc catccggttc ggtaaaaatc gctttcagcc cttcaaatgc    2682
gccttccgtg atgatgacgc tatcgccggg ataggggggtt tcaggatcga caacgccttc    2742
gggcttgtag atagaaagct gatgaataac gctggaaggc acgatcgcag gatgccgcca    2802
aagcgcacaa aatggctgac gccgcgcgtg gcgttgattg tagtggtatg tatcacttcc    2862
ggatcaaatt caacgaacag ataattagga agagcggtt cgctgacgga ggtacgtttt     2922
ccgcgtacca tttttccag ggtgatcatc ggtgtcaggc aacttaccgc ttgtctttcg      2982
aggtgttcct gagcacgctg aagttgcccg cgtttgcagt acagtaaata ccaggattgc    3042
ataatgactc ttatccgctt gttcggggcg caagcatagc aaaagccatg cgcgaagtta    3102
attatacact tcatccttta agccgtatct ggattagcgt tggttgccag agttcacgct    3162
aatttaacaa aaatacagca tcccgatgat gaacgccgta taatgatgcg cttaccaaga    3222
ggctacaatg gacgccatga aatatcacga tttacgcgac ttcctgacgc tacttgagca    3282
gcaggggaa ctaaaacgca tcacgctacc tgtggatcct catctggaaa tcacggaaat    3342
cgctgaccgc acgctgcgtg ccggtggacc ggcgttgctg tttgaaaatc ctaaaggtta    3402
cgccatgccg gtgctgtgca acctttttgg cacgccaaaa cgcgtggcga tgggcatggg    3462
gcaggatgat gtttccgcct tacgggaagt gggtaaatta ttagcgtttc ttaaagaacc    3522
tgagccgccg aaagcgtttc gcgatctgtt tgacaagctg ccgcagttta agcaagtgct    3582
gaatatgccg acgaaacggt tacgcggcgc gccttgccag cagaaaatcg cgtctggcga    3642
tgatgtcgat ttaacgcgtc ttcctgtcat gacctgttgg ccggacgacg ccgcgccgct    3702
gattacctgg ggactgacgg taacgcgtgg tccgcacaaa gagcggcaaa acctgggcat    3762
ttatcgtcag cagttgatag gtaaaaataa gctgattatg cgctggctgt ctcaccgcgg    3822
cggcgcgctg gattttcagg agtggttagc cgcgcgtccg ggtgaacgtt tcccggtctc    3882
cgtcgcattg ggcgccgatc cggcacgata cttggcgccg tgactcctgt tcccgatact    3942
ctgtcggagt atgcctttgc gggcctgctg cgcggcacga aaactgaagt ggttaatgct    4002
ttctacgatc tggagtgctg cagcgcgaga tatcttgaag tacatgagcg gagagatgcg    4062
cggagacgta tgcgatcata cggcatatat gagtgatagc tcgtcttacg tcacgcaata    4122
acagcgtaga tgcatctata tcactatacg cgcgcatgag ctcgtatagg tgcctcatat    4182
ctcgtctatc tcaaagtc                                                  4200
```

<210> SEQ ID NO 18
<211> LENGTH: 166
<212> TYPE: PRT
<213> ORGANISM: Salmonella typhimurium

<400> SEQUENCE: 18

```
Met Ala Val Glu Asp Thr Gln Pro Leu Ile Thr His Leu Ile Glu Leu
 1               5                  10                  15

Arg Lys Arg Leu Leu Asn Cys Ile Val Ala Val Leu Leu Ile Phe Leu
                20                  25                  30

Ala Leu Ile Tyr Phe Ala Asn Asp Ile Tyr His Leu Val Ala Ala Pro
            35                  40                  45

Leu Ile Lys Gln Met Pro Gln Gly Ala Thr Met Ile Ala Thr Asp Val
        50                  55                  60
```

-continued

Ala Ser Pro Phe Phe Thr Pro Ile Lys Leu Thr Phe Met Val Ser Leu
 65                  70                  75                  80

Ile Leu Ser Ala Pro Val Ile Leu Tyr Gln Val Trp Ala Phe Ile Ala
                 85                  90                  95

Pro Ala Leu Tyr Lys His Glu Arg Arg Leu Val Val Pro Leu Leu Val
            100                 105                 110

Ser Ser Ser Leu Leu Phe Tyr Ile Gly Met Ala Phe Ala Tyr Phe Val
        115                 120                 125

Val Phe Pro Leu Ala Phe Gly Phe Leu Thr His Thr Ala Pro Glu Gly
130                 135                 140

Val Gln Val Ser Thr Asp Ile Ala Ser Tyr Leu Ser Phe Val Met Ala
145                 150                 155                 160

Leu Phe Met Ala Phe Ala
                165

<210> SEQ ID NO 19
<211> LENGTH: 91
<212> TYPE: PRT
<213> ORGANISM: Salmonella typhimurium

<400> SEQUENCE: 19

Phe Glu Val Pro Val Ala Ile Val Leu Leu Cys Trp Met Gly Ile Thr
  1               5                  10                  15

Thr Pro Glu Asp Leu Arg Lys Lys Arg Pro Tyr Ile Leu Val Gly Ala
                 20                  25                  30

Phe Ile Val Gly Met Leu Leu Thr Pro Pro Asp Val Phe Ser Gln Thr
            35                  40                  45

Leu Leu Ala Ile Pro Met Tyr Cys Leu Phe Glu Ile Gly Val Phe Cys
        50                  55                  60

Ser Arg Phe Tyr Val Gly Lys Arg Arg Thr Arg Asp Glu Asp Asn Glu
 65                  70                  75                  80

Ala Glu Thr Glu Lys Ala Glu His Thr Glu Asp
                 85                  90

<210> SEQ ID NO 20
<211> LENGTH: 2601
<212> TYPE: DNA
<213> ORGANISM: Neisseria meningitidis
<220> FEATURE:
<221> NAME/KEY: CDS
<222> LOCATION: (1572)..(2339)

<400> SEQUENCE: 20
agacaaaatc ctaaaaaaag tgattgaaga ggcgggcgaa gtgttgatgg catccaaaga      60
caaaaacccg tcccacctgg tttacgaagt tgccgactta tggtttcaca ccatgattct     120
tctgacacac cacgacctga aggcggaaga cgtattggac gaacttgcgc gccgccaagg     180
tttgtcgggc ttggccgaaa aagccgctcg cacagaatct tgaatttata ttaaaatccg     240
cactttccca cattcaatcc gtctgaccgc tgttcagacg gcatcggagc cgttatggac     300
aactgtattt tctgcaaaat cgccgccaaa gacattccgg cgcaaaccgt ctatgaagac     360
ggcgaaatgg tttgtttcaa agacatcaac cccgctgctc cggttcatct gctgctgatt     420
cccaaagtcc atttcgattc gttggcacac gccgcgcccg aacatcagcc cttttggga      480 aaaatgatgc tgaaagttcc cgaaatcgcc aaagcggcag gactggcaga cggcttcaaa     540
accctgatca caccggaaa aggcggcgga caagaggtct tccacctgca tatacacatc      600

```
atgggcacac ccgtataaac cgttatttca caatcaaccc ctaatactta cttaaggata   660
catcatgggc agtttttctc tgacgcactg gattatcgta ctgattatcg tcgttttgat   720
attcggcacc aaaaaactgc gcaacgtcgg caaagacctc ggcggtgcgg ttcatgactt   780
caaacagggg ctgaacgaag gtacagacgg caaagaagcc caaaaagacg atgtaatcga   840
acacaaaaaa gacgaagaca aagcgtaatt tatgtttgat ttcggtttgg gcgagctggt   900
ttttgtcggc attatcgccc tgattgtcct cggccccgaa cgcctgcccg aggccgcccg   960
caccgccgga cggctcatcg gcaggctgca acgctttgtc ggcagcgtca acaggaatt  1020
tgacacgcaa atcgaactgg aagaactaag gaaggcaaag caggaatttg aagctgccgc  1080
tgctcaggtt cgagacagcc tcaaagaaac cggtacggat atggagggta atctgcacga  1140
catttccgac ggtctgaagc cttgggaaaa actgcccgaa cagcgcacgc ctgctgattt  1200
cggtgtcgat gaaaacggca atcccttttcc cgatgcggca acaccctat agacggcat  1260
ttccgacgtt atgccgtccg aacgttccta cgcttccgcc gaaaccttg gggacagcgg  1320
gcaaaccggc agtacagccg aacccgcgga accgaccaa gaccgtgcat ggcgggaata  1380
cctgactgct tctgccgccg cacccgtcgt acagaccgtc gaagtcagct atatcgatac  1440
cgctgttgaa ccccctgttc cgcataccac ttcgctgcgt aaacaggcaa taagccgcaa  1500
acgcgatttg cgtcctaaat cccgcgccaa acctaaattg cgcgtccgta atcataaag  1560 aggcaatcc g gtg tcc gaa aca caa aac gaa caa ccc gtc caa ccg ctt  1610
            Val Ser Glu Thr Gln Asn Glu Gln Pro Val Gln Pro Leu
              1               5                  10 gtc gag cat ctc atc gag ctg cgc cgc cgc ctg atg tgg acg gtt gtc  1658
Val Glu His Leu Ile Glu Leu Arg Arg Arg Leu Met Trp Thr Val Val
 15              20                  25 ggt atc tta gtc tgc ttt ttc ggc cta atg ccg ttt gcc caa caa ctc  1706
Gly Ile Leu Val Cys Phe Phe Gly Leu Met Pro Phe Ala Gln Gln Leu
 30              35                  40                      45 tat act ttt atc gcc gac ccg ctg atg gca aac ctg ccc aaa gac acc  1754
Tyr Thr Phe Ile Ala Asp Pro Leu Met Ala Asn Leu Pro Lys Asp Thr
             50                  55                  60 agc atg att gcc acc gat gtc atc gca cca ttt ttc gtg ccg gtc aaa  1802
Ser Met Ile Ala Thr Asp Val Ile Ala Pro Phe Phe Val Pro Val Lys
         65                  70                  75 gtt acc ctg atg gcg gca ttt tta att tcg ctg ccg cat acg ctc tac  1850
Val Thr Leu Met Ala Ala Phe Leu Ile Ser Leu Pro His Thr Leu Tyr
     80                  85                  90 caa atc tgg gca ttc gtc gcc ccc gca ctc tac caa aac gaa aaa cgc  1898
Gln Ile Trp Ala Phe Val Ala Pro Ala Leu Tyr Gln Asn Glu Lys Arg
 95                 100                 105 ctg att acg ccg ctc gtc ctc tcc agc gtc agc ctg ttt ttc atc ggc  1946
Leu Ile Thr Pro Leu Val Leu Ser Ser Val Ser Leu Phe Phe Ile Gly
110                 115                 120                 125 atg gca ttt gcc tac ttt ttg gtt ttc ccc gtc att ttc aaa ttc ctt  1994
Met Ala Phe Ala Tyr Phe Leu Val Phe Pro Val Ile Phe Lys Phe Leu
                130                 135                 140 gcc agc gtt acc cct gtc ggt gtc aat atg gcg aca gac atc gac aaa  2042
Ala Ser Val Thr Pro Val Gly Val Asn Met Ala Thr Asp Ile Asp Lys
            145                 150                 155 tac ctc tcc ttc atc ttg ggg atg ttt gtc gca ttc ggt aca acg ttt  2090
Tyr Leu Ser Phe Ile Leu Gly Met Phe Val Ala Phe Gly Thr Thr Phe
            160                 165                 170 gaa gtc ccc att gtc gtt atc ctg tta acc aaa att ggt gtg gta aca  2138
Glu Val Pro Ile Val Val Ile Leu Leu Thr Lys Ile Gly Val Val Thr
175                 180                 185
```

-continued

```
acc gaa cag ctc aaa cgc gcc cgc ccc tat gtg att gtc ggc gcg ttt      2186
Thr Glu Gln Leu Lys Arg Ala Arg Pro Tyr Val Ile Val Gly Ala Phe
190             195                 200                 205 gtc att gcc gcc atc atc acg ccg ccc gat gtg att tca caa acc ctg      2234
Val Ile Ala Ala Ile Ile Thr Pro Pro Asp Val Ile Ser Gln Thr Leu
                210                 215                 220 ctt gcc att ccg ctg att ctc tta tac gaa gca ggt att tgg ttc gga      2282
Leu Ala Ile Pro Leu Ile Leu Leu Tyr Glu Ala Gly Ile Trp Phe Gly
            225                 230                 235 cgc ttt ttc acg cca cgt tca gaa cag gat ggc gac ata cag ccg cct      2330
Arg Phe Phe Thr Pro Arg Ser Glu Gln Asp Gly Asp Ile Gln Pro Pro
        240                 245                 250 gca aca acc tgacactatg ccgtccgaac ctccgcctca taccgccaca              2379
Ala Thr Thr
    255 gattaaggaa tacctttgaa taccctctat ttaggttcaa acagcccgcg ccgaatggaa    2439 atcctgacac agttgggcta tcaggtcgtc aagctgcctg ccaacatcga cgaaacggtc    2499 agacagaacg aagaccctgc cgttacgtt caaaggatgg cagaagaaaa aaaccgaacc     2559 gccctgaccc tcttttgcga aaccaacggc acaatgcccg at                      2601
```

<210> SEQ ID NO 21
<211> LENGTH: 256
<212> TYPE: PRT
<213> ORGANISM: Neisseria meningitidis

<400> SEQUENCE: 21

```
Val Ser Glu Thr Gln Asn Glu Gln Pro Val Gln Pro Leu Val Glu His
  1               5                  10                  15

Leu Ile Glu Leu Arg Arg Arg Leu Met Trp Thr Val Val Gly Ile Leu
                 20                  25                  30

Val Cys Phe Phe Gly Leu Met Pro Phe Ala Gln Gln Leu Tyr Thr Phe
             35                  40                  45

Ile Ala Asp Pro Leu Met Ala Asn Leu Pro Lys Asp Thr Ser Met Ile
         50                  55                  60

Ala Thr Asp Val Ile Ala Pro Phe Phe Val Pro Val Lys Val Thr Leu
 65                  70                  75                  80

Met Ala Ala Phe Leu Ile Ser Leu Pro His Thr Leu Tyr Gln Ile Trp
                 85                  90                  95

Ala Phe Val Ala Pro Ala Leu Tyr Gln Asn Glu Lys Arg Leu Ile Thr
            100                 105                 110

Pro Leu Val Leu Ser Ser Val Ser Leu Phe Phe Ile Gly Met Ala Phe
        115                 120                 125

Ala Tyr Phe Leu Val Phe Pro Val Ile Phe Lys Phe Leu Ala Ser Val
    130                 135                 140

Thr Pro Val Gly Val Asn Met Ala Thr Asp Ile Asp Lys Tyr Leu Ser
145                 150                 155                 160

Phe Ile Leu Gly Met Phe Val Ala Phe Gly Thr Thr Phe Glu Val Pro
                165                 170                 175

Ile Val Val Ile Leu Leu Thr Lys Ile Gly Val Val Thr Thr Glu Gln
            180                 185                 190

Leu Lys Arg Ala Arg Pro Tyr Val Ile Gly Ala Phe Val Ile Ala
        195                 200                 205

Ala Ile Ile Thr Pro Pro Asp Val Ile Ser Gln Thr Leu Leu Ala Ile
    210                 215                 220

Pro Leu Ile Leu Leu Tyr Glu Ala Gly Ile Trp Phe Gly Arg Phe Phe
```

-continued

```
              225                 230                 235                 240
        Thr Pro Arg Ser Glu Gln Asp Gly Asp Ile Gln Pro Pro Ala Thr Thr
                          245                 250                 255

<210> SEQ ID NO 22
<211> LENGTH: 4604
<212> TYPE: DNA
<213> ORGANISM: Escherichia coli
<220> FEATURE:
<221> NAME/KEY: CDS
<222> LOCATION: (2982)..(4082)
<221> NAME/KEY: CDS
<222> LOCATION: (1534)..(2637)
<221> NAME/KEY: CDS
<222> LOCATION: (749)..(1531)
<221> NAME/KEY: CDS
<222> LOCATION: (6)..(746)

<400> SEQUENCE: 22 ggcta gtt gat gat aat ttg aaa ggt caa ggt gca gga aaa aat ttt tta      50
      Val Asp Asp Asn Leu Lys Gly Gln Gly Ala Gly Lys Asn Phe Leu
        1               5                  10                  15 tcg ctg ata aag tac agc gag aca gat tat aca att tat tgt gac caa        98
Ser Leu Ile Lys Tyr Ser Glu Thr Asp Tyr Thr Ile Tyr Cys Asp Gln
             20                  25                  30 gat gat att tgg tta gaa aac aaa ata ttt gaa tta gta aag tat gca       146
Asp Asp Ile Trp Leu Glu Asn Lys Ile Phe Glu Leu Val Lys Tyr Ala
     35                  40                  45 aat gaa att aaa ttg aat gta tca gat gcg cct tcg cta gtt tat gct       194
Asn Glu Ile Lys Leu Asn Val Ser Asp Ala Pro Ser Leu Val Tyr Ala
 50                  55                  60 gat ggc tat gct tat atg gat ggt gag ggt aca atc gat ttt tct ggg       242
Asp Gly Tyr Ala Tyr Met Asp Gly Glu Gly Thr Ile Asp Phe Ser Gly
             65                  70                  75 ata tct aac aat cat gct gat caa tta aag gat ttt ctt ttt ttt aat       290
Ile Ser Asn Asn His Ala Asp Gln Leu Lys Asp Phe Leu Phe Phe Asn
 80                  85                  90                  95 ggt gga tac caa gga tgt tct att atg ttc aat cgt gca atg acc aaa       338
Gly Gly Tyr Gln Gly Cys Ser Ile Met Phe Asn Arg Ala Met Thr Lys
            100                 105                 110 ttt ctt ctg aat tat cga gga ttt gta tat cta cat gac gat atc aca       386
Phe Leu Leu Asn Tyr Arg Gly Phe Val Tyr Leu His Asp Asp Ile Thr
            115                 120                 125 aca tta gct gca tac gct ctt ggt aaa gtt tat ttt ctc ccg aaa tac       434
Thr Leu Ala Ala Tyr Ala Leu Gly Lys Val Tyr Phe Leu Pro Lys Tyr
        130                 135                 140 ctt atg tta tat aga cag cac acg aat gcg gta act ggt atc aaa aca       482
Leu Met Leu Tyr Arg Gln His Thr Asn Ala Val Thr Gly Ile Lys Thr
    145                 150                 155 ttc cgc aat gga ttg act tct aaa ttt aaa tca cca gta aac tat ctt       530
Phe Arg Asn Gly Leu Thr Ser Lys Phe Lys Ser Pro Val Asn Tyr Leu
160                 165                 170                 175 tta tca cga aaa cat tat cag gta aaa aaa tct ttt ttt gaa tgt aac       578
Leu Ser Arg Lys His Tyr Gln Val Lys Lys Ser Phe Phe Glu Cys Asn
                180                 185                 190 agc tct atc tta tca gag acg aat aaa aaa gtt ttt ttg gat ttt att       626
Ser Ser Ile Leu Ser Glu Thr Asn Lys Lys Val Phe Leu Asp Phe Ile
            195                 200                 205 tca ttt tgt gaa tca aat aat aaa ttt aca gat ttt ttt aag tta tgg       674
Ser Phe Cys Glu Ser Asn Asn Lys Phe Thr Asp Phe Phe Lys Leu Trp
        210                 215                 220 cga ggt ggg ttt aga tta aat aac agt aga act aaa tta tta tta aaa       722
```

```
Arg Gly Gly Phe Arg Leu Asn Asn Ser Arg Thr Lys Leu Leu Leu Lys
    225                 230                 235 ttc tta ata cgg aga aaa ttt agc ga  atg att tca ata ctt aca cct        769
Phe Leu Ile Arg Arg Lys Phe Ser     Met Ile Ser Ile Leu Thr Pro
240                 245                 250 act ttt aat cgg caa cat act tta tca agg cta ttc aat tct ctt ata        817
Thr Phe Asn Arg Gln His Thr Leu Ser Arg Leu Phe Asn Ser Leu Ile
255                 260                 265                 270 tta caa act gat aaa gat ttt gag tgg ata ata att gat gat ggt agt        865
Leu Gln Thr Asp Lys Asp Phe Glu Trp Ile Ile Ile Asp Asp Gly Ser
                275                 280                 285 ata gat gca aca gcg gta ctt gta gaa gat ttt aga aaa aaa tgt gat        913
Ile Asp Ala Thr Ala Val Leu Val Glu Asp Phe Arg Lys Lys Cys Asp
            290                 295                 300 ttt gac ttg att tat tgc tat cag gaa aat aat ggt aag ccc atg gct        961
Phe Asp Leu Ile Tyr Cys Tyr Gln Glu Asn Asn Gly Lys Pro Met Ala
        305                 310                 315 tta aac gct ggt gtt aaa gct tgt aga ggc gat tat atc ttt att gtt       1009
Leu Asn Ala Gly Val Lys Ala Cys Arg Gly Asp Tyr Ile Phe Ile Val
    320                 325                 330 gac agt gat gat gca cta act ccc gat gcc ata aaa tta att aaa gaa       1057
Asp Ser Asp Asp Ala Leu Thr Pro Asp Ala Ile Lys Leu Ile Lys Glu
335                 340                 345                 350 tca ata cat gat tgc tta tct gag aag gaa agt ttc agc gga gtc ggt       1105
Ser Ile His Asp Cys Leu Ser Glu Lys Glu Ser Phe Ser Gly Val Gly
                355                 360                 365 ttt aga aaa gca tat ata aaa ggg ggg att att ggt aat gat tta aat       1153
Phe Arg Lys Ala Tyr Ile Lys Gly Gly Ile Ile Gly Asn Asp Leu Asn
            370                 375                 380 aat tct tca gaa cat ata tac tat tta aat gcg act gag att agc aat       1201
Asn Ser Ser Glu His Ile Tyr Tyr Leu Asn Ala Thr Glu Ile Ser Asn
        385                 390                 395 tta ata aat ggt gat gtt gca tat tgt ttt aaa aaa gaa agt ttg gta       1249
Leu Ile Asn Gly Asp Val Ala Tyr Cys Phe Lys Lys Glu Ser Leu Val
    400                 405                 410 aaa aat cca ttc ccc cgt ata gaa gat gaa aaa ttt gtt cca gaa tta       1297
Lys Asn Pro Phe Pro Arg Ile Glu Asp Glu Lys Phe Val Pro Glu Leu
415                 420                 425                 430 tat att tgg aat aaa ata act gac aag gcg aag att cga ttt aac ata       1345
Tyr Ile Trp Asn Lys Ile Thr Asp Lys Ala Lys Ile Arg Phe Asn Ile
                435                 440                 445 agc aaa gtt ata tat ctt tgt gag tat ctt gat gat ggt ctt tct aaa       1393
Ser Lys Val Ile Tyr Leu Cys Glu Tyr Leu Asp Asp Gly Leu Ser Lys
            450                 455                 460 aat ttc cat aac cag ctt aaa aaa tac cca aag ggg ttt aag att tat       1441
Asn Phe His Asn Gln Leu Lys Lys Tyr Pro Lys Gly Phe Lys Ile Tyr
        465                 470                 475 tac aaa gat caa aga aaa cga gag aaa act tat ata aaa aaa aca aag       1489
Tyr Lys Asp Gln Arg Lys Arg Glu Lys Thr Tyr Ile Lys Lys Thr Lys
    480                 485                 490 atg cta att aga tat ttg caa tgt tgt tat tat gag aaa ata aa atg       1536
Met Leu Ile Arg Tyr Leu Gln Cys Cys Tyr Tyr Glu Lys Ile    Met
495                 500                 505 aaa ata cta ttt gtc att aca ggt tta ggc ctt gga ggt gct gag aag       1584
Lys Ile Leu Phe Val Ile Thr Gly Leu Gly Leu Gly Gly Ala Glu Lys
510                 515                 520                 525 cag gtt tgt ctt tta gct gat aaa tta agt tta agc ggg cac cat gta       1632
Gln Val Cys Leu Leu Ala Asp Lys Leu Ser Leu Ser Gly His His Val
                530                 535                 540
```

-continued

| | | |
|---|---|---|
| aag att att tca ctt gga cat atg tct aat aat aaa gtc ttt cct agc<br>Lys Ile Ile Ser Leu Gly His Met Ser Asn Asn Lys Val Phe Pro Ser<br>545 550 555 | 1680 |
| gaa aat aat gtt aat gtc att aat gta aat atg tca aaa aac att tct<br>Glu Asn Asn Val Asn Val Ile Asn Val Asn Met Ser Lys Asn Ile Ser<br>560 565 570 | 1728 |
| gga gtt ata aaa ggt tgt gtc aga att aga gat gtt ata gct aat ttc<br>Gly Val Ile Lys Gly Cys Val Arg Ile Arg Asp Val Ile Ala Asn Phe<br>575 580 585 | 1776 |
| aaa cca gac att gta cac agt cat atg ttt cat gca aac att atc act<br>Lys Pro Asp Ile Val His Ser His Met Phe His Ala Asn Ile Ile Thr<br>590 595 600 605 | 1824 |
| aga ttg tct gta att gga atc aaa aac aga cct ggt att ata tca act<br>Arg Leu Ser Val Ile Gly Ile Lys Asn Arg Pro Gly Ile Ile Ser Thr<br>610 615 620 | 1872 |
| gca cat aat aaa aat gaa ggt ggg tat ttc aga atg ctc aca tat aga<br>Ala His Asn Lys Asn Glu Gly Gly Tyr Phe Arg Met Leu Thr Tyr Arg<br>625 630 635 | 1920 |
| ata acc gat tgt tta agt gat tgt tgt aca aat gtt agc aaa gaa gca<br>Ile Thr Asp Cys Leu Ser Asp Cys Cys Thr Asn Val Ser Lys Glu Ala<br>640 645 650 | 1968 |
| gtg gat gag ttt tta cgg ata aaa gcc ttt aat ccc gct aaa gca att<br>Val Asp Glu Phe Leu Arg Ile Lys Ala Phe Asn Pro Ala Lys Ala Ile<br>655 660 665 | 2016 |
| act atg tat aat ggg ata gat acc aat aaa ttt aaa ttt gat tta ttg<br>Thr Met Tyr Asn Gly Ile Asp Thr Asn Lys Phe Lys Phe Asp Leu Leu<br>670 675 680 685 | 2064 |
| gca agg agg gaa att cga gac ggt att aat ata aaa aat gat gat ata<br>Ala Arg Arg Glu Ile Arg Asp Gly Ile Asn Ile Lys Asn Asp Asp Ile<br>690 695 700 | 2112 |
| tta tta ctt gct gca ggt cgt tta acg tta gct aaa gat tat cct aat<br>Leu Leu Leu Ala Ala Gly Arg Leu Thr Leu Ala Lys Asp Tyr Pro Asn<br>705 710 715 | 2160 |
| tta ttg aat gca atg act ctg ctt cct gaa cac ttt aaa ctt att att<br>Leu Leu Asn Ala Met Thr Leu Leu Pro Glu His Phe Lys Leu Ile Ile<br>720 725 730 | 2208 |
| att ggt gat ggt gaa ttg cgt gac gaa att aat atg ctt ata aaa aaa<br>Ile Gly Asp Gly Glu Leu Arg Asp Glu Ile Asn Met Leu Ile Lys Lys<br>735 740 745 | 2256 |
| ttg caa tta tct aat agg gtg tcc ttg ttg gga gtt aaa aaa aat att<br>Leu Gln Leu Ser Asn Arg Val Ser Leu Leu Gly Val Lys Lys Asn Ile<br>750 755 760 765 | 2304 |
| gct ccc tat ttt tct gca tgt gat att ttt gtt ctc tct tct cgt tgg<br>Ala Pro Tyr Phe Ser Ala Cys Asp Ile Phe Val Leu Ser Ser Arg Trp<br>770 775 780 | 2352 |
| gaa gga ttt gga tta gtc gtg gca gaa gct atg tca tgt gag cga att<br>Glu Gly Phe Gly Leu Val Val Ala Glu Ala Met Ser Cys Glu Arg Ile<br>785 790 795 | 2400 |
| gtt gtt ggc acg gat tca ggg gga gta aga gaa gtt att ggt gac gat<br>Val Val Gly Thr Asp Ser Gly Gly Val Arg Glu Val Ile Gly Asp Asp<br>800 805 810 | 2448 |
| gat ttt ctt gta ccc ata tct gat tca aca caa ctt gca agc aaa att<br>Asp Phe Leu Val Pro Ile Ser Asp Ser Thr Gln Leu Ala Ser Lys Ile<br>815 820 825 | 2496 |
| gaa aaa ttg tct ttg agc cag ata cgt gat cac att ggt ttt cgg aat<br>Glu Lys Leu Ser Leu Ser Gln Ile Arg Asp His Ile Gly Phe Arg Asn<br>830 835 840 845 | 2544 |
| cgt gag cgt att tta aaa aat ttc tca ata gat act att att atg cag<br>Arg Glu Arg Ile Leu Lys Asn Phe Ser Ile Asp Thr Ile Ile Met Gln<br>850 855 860 | 2592 |

```
tgg caa gaa ctc tat gga act ata att tgc tca aaa cat gaa agg         2637
Trp Gln Glu Leu Tyr Gly Thr Ile Ile Cys Ser Lys His Glu Arg
            865                 870                 875 tagatttata tttggaacgt gtcttttgtt tgaatttaat tcaatctcaa ttgagatttt    2697
tgtatttcaa aaataccatc atagctaacg atgattggta tttattttaa gatgctttct   2757
ataaatatat tgacgttttt aatgcgccga acgattggg ctgggaacag agaagtaaaa    2817
ctgttttgag aatgaagagt ttttgagatg tttatggata ttaaaaattg atccagtgaa   2877
ttaattattt ataataaatc aagatttaat gttaataaat gataatcttt tctgacactc   2937
atattaatta tgagtggtac gtttggtaaa cggtaaacta ttat atg aca gct aga    2993
                                                Met Thr Ala Arg
                                                            880 aca act aaa gtt ttg cac tta caa tta ctc cca ctc tta agt ggc gtt     3041
Thr Thr Lys Val Leu His Leu Gln Leu Leu Pro Leu Leu Ser Gly Val
            885                 890                 895 caa agg gta aca tta aac gaa att agt gcg tta tat act gat tat gat     3089
Gln Arg Val Thr Leu Asn Glu Ile Ser Ala Leu Tyr Thr Asp Tyr Asp
            900                 905                 910 tat aca cta gtt tgc tca aaa aaa ggt cca cta aca aaa gca ttg ctg     3137
Tyr Thr Leu Val Cys Ser Lys Lys Gly Pro Leu Thr Lys Ala Leu Leu
            915                 920                 925 gaa tat gat gtc gat tgt cat tgt atc ccc gaa ctt acg aga gaa att     3185
Glu Tyr Asp Val Asp Cys His Cys Ile Pro Glu Leu Thr Arg Glu Ile
        930                 935                 940 acc gta aag aat gat ttt aaa gca ttg ttc aag ctt tat aag ttc ata     3233
Thr Val Lys Asn Asp Phe Lys Ala Leu Phe Lys Leu Tyr Lys Phe Ile
945                 950                 955                 960 aaa aaa gaa aaa ttt gac att gtg cat aca cat tct tca aaa aca ggt     3281
Lys Lys Glu Lys Phe Asp Ile Val His Thr His Ser Ser Lys Thr Gly
            965                 970                 975 att ttg ggg cga gtt gct gcc aaa tta gca cgt gtt gga aag gtg atc     3329
Ile Leu Gly Arg Val Ala Ala Lys Leu Ala Arg Val Gly Lys Val Ile
            980                 985                 990 cac act gta cat ggt ttt tct ttt cca gcc gca tct agt aaa aaa agt     3377
His Thr Val His Gly Phe Ser Phe Pro Ala Ala Ser Ser Lys Lys Ser
            995                 1000                1005 tat tac ctt tat ttt ttc atg gaa tgg ata gca aag ttc ttt acg gat     3425
Tyr Tyr Leu Tyr Phe Phe Met Glu Trp Ile Ala Lys Phe Phe Thr Asp
      1010                1015                1020 aag tta atc gtc ttg aat gta gat gat gaa tat ata gca ata aac aaa     3473
Lys Leu Ile Val Leu Asn Val Asp Asp Glu Tyr Ile Ala Ile Asn Lys
1025                1030                1035                1040 tta aaa ttc aag cgg gat aaa gtt ttt tta att cct aat gga gta gac     3521
Leu Lys Phe Lys Arg Asp Lys Val Phe Leu Ile Pro Asn Gly Val Asp
                1045                1050                1055 act gat aag ttt tct cct tta gaa aat aaa att tat agt agc acc ttg     3569
Thr Asp Lys Phe Ser Pro Leu Glu Asn Lys Ile Tyr Ser Ser Thr Leu
                1060                1065                1070 aat cta gta atg gtt ggt aga tta tcc aag caa aaa gat cct gag aca     3617
Asn Leu Val Met Val Gly Arg Leu Ser Lys Gln Lys Asp Pro Glu Thr
            1075                1080                1085 tta ttg ctt gct gtt gaa aaa ctg ctg aat gaa aat gtt aat gtt aag     3665
Leu Leu Leu Ala Val Glu Lys Leu Leu Asn Glu Asn Val Asn Val Lys
            1090                1095                1100 ctg aca ctt gta gga gat ggt gaa cta aaa gaa cag tta gaa agc agg     3713
Leu Thr Leu Val Gly Asp Gly Glu Leu Lys Glu Gln Leu Glu Ser Arg
1105                1110                1115                1120
```

-continued

| | | |
|---|---|---|
| ttc aaa cgg caa gat gga cgt ata att ttt cat gga tgg tca gat aac<br>Phe Lys Arg Gln Asp Gly Arg Ile Ile Phe His Gly Trp Ser Asp Asn<br>    1125                1130                1135 | | 3761 |
| att gtt aat att tta aaa gtt aat gat ctt ttt ata tta cct tct ctt<br>Ile Val Asn Ile Leu Lys Val Asn Asp Leu Phe Ile Leu Pro Ser Leu<br>        1140                1145                1150 | | 3809 |
| tgg gag ggt atg cca tta gca att tta gaa gca ttg agc tgt gga ctt<br>Trp Glu Gly Met Pro Leu Ala Ile Leu Glu Ala Leu Ser Cys Gly Leu<br>    1155                1160                1165 | | 3857 |
| cca tgt ata gtc act aat att cca ggt aat aat agc tta ata gaa gat<br>Pro Cys Ile Val Thr Asn Ile Pro Gly Asn Asn Ser Leu Ile Glu Asp<br>1170                1175                1180 | | 3905 |
| ggc tat aat ggt tgt ttg ttt gaa att aga gat tgt cag tta tta tct<br>Gly Tyr Asn Gly Cys Leu Phe Glu Ile Arg Asp Cys Gln Leu Leu Ser<br>1185                1190                1195                1200 | | 3953 |
| caa aaa atc atg tca tat gtt ggt aag cca gaa ctg att gca cag caa<br>Gln Lys Ile Met Ser Tyr Val Gly Lys Pro Glu Leu Ile Ala Gln Gln<br>        1205                1210                1215 | | 4001 |
| tct acc aat gca cga tca ttt att ctg aaa aat tat gga tta gtt aaa<br>Ser Thr Asn Ala Arg Ser Phe Ile Leu Lys Asn Tyr Gly Leu Val Lys<br>    1220                1225                1230 | | 4049 |
| aga aat aat aag gtc aga cag cta tat gat aat taaatgaaac cgaaaagtta<br>Arg Asn Asn Lys Val Arg Gln Leu Tyr Asp Asn<br>1235                1240 | | 4102 |
| aaaaagaaca ggttttttcaa agtgaaaata aaattacagt ttttttattg caatgattaa | | 4162 |
| cgtaacatct gcattacatt caagccgcac aaccccgcgg tgaccacccc tgacaggagt | | 4222 |
| aaacaatgtc aaagcaacag atcggcgtcg tcggtatggc agtgatggga cgcaacctcg | | 4282 |
| cgctcaacat cgaaagccgt ggttataccg tctctatttt caaccgttcc cgtgaaaaga | | 4342 |
| cggaagaagt tattgccgaa atccaggca agaaactggt tccttactat acggtgaaag | | 4402 |
| agttcgttga atctcttgaa acgcctcgtc gcatcctgtt aatgggttaa agcaggtgca | | 4462 |
| ggcacggatg ctgctattga ttccctgaaa ccatatctcg ataaaggcga tatcatcatt | | 4522 |
| gatgggtggg taataccttc tttcaggaca ccattcgtcg taaccgcgag ctttctgcac | | 4582 |
| aaggctttac ttcatcggta cc | | 4604 |

<210> SEQ ID NO 23
<211> LENGTH: 247
<212> TYPE: PRT
<213> ORGANISM: Escherichia coli

<400> SEQUENCE: 23

Val Asp Asp Asn Leu Lys Gly Gln Gly Ala Gly Lys Asn Phe Leu Ser
 1               5                  10                  15

Leu Ile Lys Tyr Ser Glu Thr Asp Tyr Thr Ile Tyr Cys Asp Gln Asp
            20                  25                  30

Asp Ile Trp Leu Glu Asn Lys Ile Phe Glu Leu Val Lys Tyr Ala Asn
        35                  40                  45

Glu Ile Lys Leu Asn Val Ser Asp Ala Pro Ser Leu Val Tyr Ala Asp
    50                  55                  60

Gly Tyr Ala Tyr Met Asp Gly Glu Gly Thr Ile Asp Phe Ser Gly Ile
65                  70                  75                  80

Ser Asn Asn His Ala Asp Gln Leu Lys Asp Phe Leu Phe Phe Asn Gly
                85                  90                  95

Gly Tyr Gln Gly Cys Ser Ile Met Phe Asn Arg Ala Met Thr Lys Phe
            100                 105                 110

```
Leu Leu Asn Tyr Arg Gly Phe Val Tyr Leu His Asp Asp Ile Thr Thr
        115                 120                 125

Leu Ala Ala Tyr Ala Leu Gly Lys Val Tyr Phe Leu Pro Lys Tyr Leu
130                 135                 140

Met Leu Tyr Arg Gln His Thr Asn Ala Val Thr Gly Ile Lys Thr Phe
145                 150                 155                 160

Arg Asn Gly Leu Thr Ser Lys Phe Lys Ser Pro Val Asn Tyr Leu Leu
                165                 170                 175

Ser Arg Lys His Tyr Gln Val Lys Lys Ser Phe Phe Glu Cys Asn Ser
                180                 185                 190

Ser Ile Leu Ser Glu Thr Asn Lys Val Phe Leu Asp Phe Ile Ser
        195                 200                 205

Phe Cys Glu Ser Asn Asn Lys Phe Thr Asp Phe Lys Leu Trp Arg
210                 215                 220

Gly Gly Phe Arg Leu Asn Asn Ser Arg Thr Lys Leu Leu Lys Phe
225                 230                 235                 240

Leu Ile Arg Arg Lys Phe Ser
                245

<210> SEQ ID NO 24
<211> LENGTH: 261
<212> TYPE: PRT
<213> ORGANISM: Escherichia coli

<400> SEQUENCE: 24

Met Ile Ser Ile Leu Thr Pro Thr Phe Asn Arg Gln His Thr Leu Ser
1               5                   10                  15

Arg Leu Phe Asn Ser Leu Ile Leu Gln Thr Asp Lys Asp Phe Glu Trp
                20                  25                  30

Ile Ile Ile Asp Asp Gly Ser Ile Asp Ala Thr Ala Val Leu Val Glu
            35                  40                  45

Asp Phe Arg Lys Lys Cys Asp Phe Asp Leu Ile Tyr Cys Tyr Gln Glu
        50                  55                  60

Asn Asn Gly Lys Pro Met Ala Leu Asn Ala Gly Val Lys Ala Cys Arg
65                  70                  75                  80

Gly Asp Tyr Ile Phe Ile Val Asp Ser Asp Asp Ala Leu Thr Pro Asp
                85                  90                  95

Ala Ile Lys Leu Ile Lys Glu Ser Ile His Asp Cys Leu Ser Glu Lys
                100                 105                 110

Glu Ser Phe Ser Gly Val Gly Phe Arg Lys Ala Tyr Ile Lys Gly Gly
            115                 120                 125

Ile Ile Gly Asn Asp Leu Asn Asn Ser Ser Glu His Ile Tyr Tyr Leu
130                 135                 140

Asn Ala Thr Glu Ile Ser Asn Leu Ile Asn Gly Asp Val Ala Tyr Cys
145                 150                 155                 160

Phe Lys Lys Glu Ser Leu Val Lys Asn Pro Phe Pro Arg Ile Glu Asp
                165                 170                 175

Glu Lys Phe Val Pro Glu Leu Tyr Ile Trp Asn Lys Ile Thr Asp Lys
            180                 185                 190

Ala Lys Ile Arg Phe Asn Ile Ser Lys Val Ile Tyr Leu Cys Glu Tyr
        195                 200                 205

Leu Asp Asp Gly Leu Ser Lys Asn Phe His Asn Gln Leu Lys Lys Tyr
210                 215                 220

Pro Lys Gly Phe Lys Ile Tyr Tyr Lys Asp Gln Arg Lys Arg Glu Lys
225                 230                 235                 240
```

```
Thr Tyr Ile Lys Lys Thr Lys Met Leu Ile Arg Tyr Leu Gln Cys Cys
                245                 250                 255
Tyr Tyr Glu Lys Ile
            260

<210> SEQ ID NO 25
<211> LENGTH: 368
<212> TYPE: PRT
<213> ORGANISM: Escherichia coli

<400> SEQUENCE: 25

Met Lys Ile Leu Phe Val Ile Thr Gly Leu Gly Gly Ala Glu
  1               5                  10                  15

Lys Gln Val Cys Leu Leu Ala Asp Lys Leu Ser Leu Ser Gly His His
                 20                  25                  30

Val Lys Ile Ile Ser Leu Gly His Met Ser Asn Asn Lys Val Phe Pro
             35                  40                  45

Ser Glu Asn Asn Val Asn Val Ile Asn Val Asn Met Ser Lys Asn Ile
 50                  55                  60

Ser Gly Val Ile Lys Gly Cys Val Arg Ile Arg Asp Val Ile Ala Asn
 65                  70                  75                  80

Phe Lys Pro Asp Ile Val His Ser His Met Phe His Ala Asn Ile Ile
                 85                  90                  95

Thr Arg Leu Ser Val Ile Gly Ile Lys Asn Arg Pro Gly Ile Ile Ser
                100                 105                 110

Thr Ala His Asn Lys Asn Glu Gly Gly Tyr Phe Arg Met Leu Thr Tyr
            115                 120                 125

Arg Ile Thr Asp Cys Leu Ser Asp Cys Cys Thr Asn Val Ser Lys Glu
130                 135                 140

Ala Val Asp Glu Phe Leu Arg Ile Lys Ala Phe Asn Pro Ala Lys Ala
145                 150                 155                 160

Ile Thr Met Tyr Asn Gly Ile Asp Thr Asn Lys Phe Lys Phe Asp Leu
                165                 170                 175

Leu Ala Arg Arg Glu Ile Arg Asp Gly Ile Asn Ile Lys Asn Asp Asp
                180                 185                 190

Ile Leu Leu Leu Ala Ala Gly Arg Leu Thr Leu Ala Lys Asp Tyr Pro
            195                 200                 205

Asn Leu Leu Asn Ala Met Thr Leu Leu Pro Glu His Phe Lys Leu Ile
210                 215                 220

Ile Ile Gly Asp Gly Glu Leu Arg Asp Glu Ile Asn Met Leu Ile Lys
225                 230                 235                 240

Lys Leu Gln Leu Ser Asn Arg Val Ser Leu Leu Gly Val Lys Lys Asn
                245                 250                 255

Ile Ala Pro Tyr Phe Ser Ala Cys Asp Ile Phe Val Leu Ser Ser Arg
                260                 265                 270

Trp Glu Gly Phe Gly Leu Val Val Ala Glu Ala Met Ser Cys Glu Arg
            275                 280                 285

Ile Val Val Gly Thr Asp Ser Gly Gly Val Arg Glu Val Ile Gly Asp
            290                 295                 300

Asp Asp Phe Leu Val Pro Ile Ser Asp Ser Thr Gln Leu Ala Ser Lys
305                 310                 315                 320

Ile Glu Lys Leu Ser Leu Ser Gln Ile Arg Asp His Ile Gly Phe Arg
                325                 330                 335

Asn Arg Glu Arg Ile Leu Lys Asn Phe Ser Ile Asp Thr Ile Ile Met
```

```
                    340              345              350
Gln Trp Gln Glu Leu Tyr Gly Thr Ile Ile Cys Ser Lys His Glu Arg
            355              360              365
```

<210> SEQ ID NO 26
<211> LENGTH: 367
<212> TYPE: PRT
<213> ORGANISM: Escherichia coli

<400> SEQUENCE: 26

```
Met Thr Ala Arg Thr Thr Lys Val Leu His Leu Gln Leu Leu Pro Leu
  1               5                  10                  15

Leu Ser Gly Val Gln Arg Val Thr Leu Asn Glu Ile Ser Ala Leu Tyr
                 20                  25                  30

Thr Asp Tyr Asp Tyr Thr Leu Val Cys Ser Lys Lys Gly Pro Leu Thr
             35                  40                  45

Lys Ala Leu Leu Glu Tyr Asp Val Asp Cys His Cys Ile Pro Glu Leu
         50                  55                  60

Thr Arg Glu Ile Thr Val Lys Asn Asp Phe Lys Ala Leu Phe Lys Leu
 65                  70                  75                  80

Tyr Lys Phe Ile Lys Lys Glu Lys Phe Asp Ile Val His Thr His Ser
                 85                  90                  95

Ser Lys Thr Gly Ile Leu Gly Arg Val Ala Ala Lys Leu Ala Arg Val
                100                 105                 110

Gly Lys Val Ile His Thr Val His Gly Phe Ser Phe Pro Ala Ala Ser
            115                 120                 125

Ser Lys Lys Ser Tyr Tyr Leu Tyr Phe Phe Met Glu Trp Ile Ala Lys
        130                 135                 140

Phe Phe Thr Asp Lys Leu Ile Val Leu Asn Val Asp Asp Glu Tyr Ile
145                 150                 155                 160

Ala Ile Asn Lys Leu Lys Phe Lys Arg Asp Lys Val Phe Leu Ile Pro
                165                 170                 175

Asn Gly Val Asp Thr Asp Lys Phe Ser Pro Leu Glu Asn Lys Ile Tyr
            180                 185                 190

Ser Ser Thr Leu Asn Leu Val Met Val Gly Arg Leu Ser Lys Gln Lys
        195                 200                 205

Asp Pro Glu Thr Leu Leu Ala Val Glu Lys Leu Leu Asn Glu Asn
    210                 215                 220

Val Asn Val Lys Leu Thr Leu Val Gly Asp Gly Glu Leu Lys Glu Gln
225                 230                 235                 240

Leu Glu Ser Arg Phe Lys Arg Gln Asp Gly Arg Ile Ile Phe His Gly
                245                 250                 255

Trp Ser Asp Asn Ile Val Asn Ile Leu Lys Val Asn Asp Leu Phe Ile
            260                 265                 270

Leu Pro Ser Leu Trp Glu Gly Met Pro Leu Ala Ile Leu Glu Ala Leu
        275                 280                 285

Ser Cys Gly Leu Pro Cys Ile Val Thr Asn Ile Pro Gly Asn Asn Ser
    290                 295                 300

Leu Ile Glu Asp Gly Tyr Asn Gly Cys Leu Phe Glu Ile Arg Asp Cys
305                 310                 315                 320

Gln Leu Leu Ser Gln Lys Ile Met Ser Tyr Val Gly Lys Pro Glu Leu
                325                 330                 335

Ile Ala Gln Gln Ser Thr Asn Ala Arg Ser Phe Ile Leu Lys Asn Tyr
            340                 345                 350
```

```
              Gly Leu Val Lys Arg Asn Asn Lys Val Arg Gln Leu Tyr Asp Asn
                              355                 360                 365

<210> SEQ ID NO 27
<211> LENGTH: 1272
<212> TYPE: DNA
<213> ORGANISM: Escherichia coli
<220> FEATURE:
<221> NAME/KEY: CDS
<222> LOCATION: (319)..(1269)
<221> NAME/KEY: CDS
<222> LOCATION: (3)..(215)

<400> SEQUENCE: 27 cc ggg aag cac tcg gcg ctg att gtt gca cat cgt ctg acc acc gcg         47
   Gly Lys His Ser Ala Leu Ile Val Ala His Arg Leu Thr Thr Ala
    1               5                  10                  15 caa cgc tgc gat ctg att gcc gtt att gat aag ggg tta ctt gcg gaa       95
Gln Arg Cys Asp Leu Ile Ala Val Ile Asp Lys Gly Leu Leu Ala Glu
             20                  25                  30 tac gga acc cac gaa cag ctg tta tct gcg ggc ggc ctc tat acc cgc      143
Tyr Gly Thr His Glu Gln Leu Leu Ser Ala Gly Gly Leu Tyr Thr Arg
         35                  40                  45 tta tgg cat gac agc gtc agc agt act gct ctc cat cgc cag cac aac      191
Leu Trp His Asp Ser Val Ser Ser Thr Ala Leu His Arg Gln His Asn
     50                  55                  60 atg aag gag gaa acc ccg gga tag ttactggaca cgtaatgtat taaaaacaca     245
Met Lys Glu Glu Thr Pro Gly
 65                 70 gtcagaagcg gcggtaccgt gaatagccgc tttaattatt tatactgaca tccttaattt    305
ttaaagagta tga atg ctg aac atg caa caa cat ctc tct gct atc gcc       354
               Met Leu Asn Met Gln Gln His Leu Ser Ala Ile Ala
                                75                  80 agc ctg cgc aac caa ctg gca gcg ggc cac att gct aac ctt act gac      402
Ser Leu Arg Asn Gln Leu Ala Ala Gly His Ile Ala Asn Leu Thr Asp
         85                  90                  95 ttc tgg cgc gaa gct gag tcg ctg aat gtt cct ctt gtg acg cca gtc      450
Phe Trp Arg Glu Ala Glu Ser Leu Asn Val Pro Leu Val Thr Pro Val
100                 105                 110                 115 gaa gga gcg gaa gat gag cga gaa gtg acc ttt ctg tgg cgc gcc cga      498
Glu Gly Ala Glu Asp Glu Arg Glu Val Thr Phe Leu Trp Arg Ala Arg
                120                 125                 130 cat cct ctg cag ggc gtt tat ctg cgt ctg aac cgg gtg acg gat aaa      546
His Pro Leu Gln Gly Val Tyr Leu Arg Leu Asn Arg Val Thr Asp Lys
            135                 140                 145 gag cac gta gaa aaa gga atg atg agc gcc ctt ccc gaa acg gat atc      594
Glu His Val Glu Lys Gly Met Met Ser Ala Leu Pro Glu Thr Asp Ile
        150                 155                 160 tgg aca ctg aca ctg cgt tta ccc gca agt tac tgc ggc tcc tat tcg      642
Trp Thr Leu Thr Leu Arg Leu Pro Ala Ser Tyr Cys Gly Ser Tyr Ser
    165                 170                 175 ctg ctg gaa atc ccc ccc ggc act acg gct gag acg att gca ctg tcc      690
Leu Leu Glu Ile Pro Pro Gly Thr Thr Ala Glu Thr Ile Ala Leu Ser
180                 185                 190                 195 gga ggc cgt ttt gcc acc ctt gcc gga aag gcc gat ccg cta aac aaa      738
Gly Gly Arg Phe Ala Thr Leu Ala Gly Lys Ala Asp Pro Leu Asn Lys
                200                 205                 210 atg ccg gag atc aac gtt cgg gga aac gca aag gaa tca gtg ctg aca      786
Met Pro Glu Ile Asn Val Arg Gly Asn Ala Lys Glu Ser Val Leu Thr
            215                 220                 225 ctt gat aaa gct ccc gcc ctg tcg gaa tgg aac ggc ggc ttc cac acc      834
```

| | | | | | | | | | | | | |
|---|---|---|---|---|---|---|---|---|---|---|---|---|
| Leu | Asp | Lys | Ala | Pro | Ala | Leu | Ser | Glu | Trp | Asn | Gly | Gly Phe His Thr |
| | | 230 | | | | 235 | | | | 240 | | |

```
gga caa ctg ctt acc tcc atg cgc att atc gcc ggg aaa tct cgc cag      882
Gly Gln Leu Leu Thr Ser Met Arg Ile Ile Ala Gly Lys Ser Arg Gln
    245                 250                 255 gtt cgg ctc tat att ccg gat gtt gat att tct cag ccc ctc ggg ctg      930
Val Arg Leu Tyr Ile Pro Asp Val Asp Ile Ser Gln Pro Leu Gly Leu
260                 265                 270                 275 gtc gtg ctg ccc gat ggt gaa acc tgg ttt gat cac ctt ggc gta tgc      978
Val Val Leu Pro Asp Gly Glu Thr Trp Phe Asp His Leu Gly Val Cys
                280                 285                 290 gcg gca att gac gcc gcc ata aat aat ggg cgc atc gtg ccc gtg gct     1026
Ala Ala Ile Asp Ala Ala Ile Asn Asn Gly Arg Ile Val Pro Val Ala
            295                 300                 305 gta ctg ggc att gac aac att aat gaa cat gaa cgc act gag ata ctc     1074
Val Leu Gly Ile Asp Asn Ile Asn Glu His Glu Arg Thr Glu Ile Leu
        310                 315                 320 ggc ggg cgc agc aaa ctg ata aag gat atc gcc gga cat ctg ctg ccg     1122
Gly Gly Arg Ser Lys Leu Ile Lys Asp Ile Ala Gly His Leu Leu Pro
    325                 330                 335 atg att cgc gct gaa caa ccg cag cgt cag tgg gca gac cgt tcg cgc     1170
Met Ile Arg Ala Glu Gln Pro Gln Arg Gln Trp Ala Asp Arg Ser Arg
340                 345                 350                 355 aca gtg ctg gcc ggg cag agc ctc ggg ggg atc agt gcg cta atg ggg     1218
Thr Val Leu Ala Gly Gln Ser Leu Gly Gly Ile Ser Ala Leu Met Gly
                360                 365                 370 gct cgt tac gca ccg gaa acg ttc ggt ctg gtg ctc agc cac tct cct     1266
Ala Arg Tyr Ala Pro Glu Thr Phe Gly Leu Val Leu Ser His Ser Pro
            375                 380                 385 caa tgc                                                              1272
Gln

<210> SEQ ID NO 28
<211> LENGTH: 70
<212> TYPE: PRT
<213> ORGANISM: Escherichia coli

<400> SEQUENCE: 28

Gly Lys His Ser Ala Leu Ile Val Ala His Arg Leu Thr Thr Ala Gln
1               5                   10                  15

Arg Cys Asp Leu Ile Ala Val Ile Asp Lys Gly Leu Leu Ala Glu Tyr
            20                  25                  30

Gly Thr His Glu Gln Leu Leu Ser Ala Gly Gly Leu Tyr Thr Arg Leu
        35                  40                  45

Trp His Asp Ser Val Ser Ser Thr Ala Leu His Arg Gln His Asn Met
    50                  55                  60

Lys Glu Glu Thr Pro Gly
65                  70

<210> SEQ ID NO 29
<211> LENGTH: 317
<212> TYPE: PRT
<213> ORGANISM: Escherichia coli

<400> SEQUENCE: 29

Met Leu Asn Met Gln Gln His Leu Ser Ala Ile Ala Ser Leu Arg Asn
1               5                   10                  15

Gln Leu Ala Ala Gly His Ile Ala Asn Leu Thr Asp Phe Trp Arg Glu
            20                  25                  30
```

-continued

```
Ala Glu Ser Leu Asn Val Pro Leu Val Thr Pro Val Glu Gly Ala Glu
         35                  40                  45

Asp Glu Arg Glu Val Thr Phe Leu Trp Arg Ala Arg His Pro Leu Gln
     50                  55                  60

Gly Val Tyr Leu Arg Leu Asn Arg Val Thr Asp Lys Glu His Val Glu
 65                  70                  75                  80

Lys Gly Met Met Ser Ala Leu Pro Glu Thr Asp Ile Trp Thr Leu Thr
                 85                  90                  95

Leu Arg Leu Pro Ala Ser Tyr Cys Gly Ser Tyr Ser Leu Leu Glu Ile
            100                 105                 110

Pro Pro Gly Thr Thr Ala Glu Thr Ile Ala Leu Ser Gly Gly Arg Phe
        115                 120                 125

Ala Thr Leu Ala Gly Lys Ala Asp Pro Leu Asn Lys Met Pro Glu Ile
130                 135                 140

Asn Val Arg Gly Asn Ala Lys Glu Ser Val Leu Thr Leu Asp Lys Ala
145                 150                 155                 160

Pro Ala Leu Ser Glu Trp Asn Gly Gly Phe His Thr Gly Gln Leu Leu
                165                 170                 175

Thr Ser Met Arg Ile Ile Ala Gly Lys Ser Arg Gln Val Arg Leu Tyr
            180                 185                 190

Ile Pro Asp Val Asp Ile Ser Gln Pro Leu Gly Leu Val Val Leu Pro
        195                 200                 205

Asp Gly Glu Thr Trp Phe Asp His Leu Gly Val Cys Ala Ala Ile Asp
210                 215                 220

Ala Ala Ile Asn Asn Gly Arg Ile Val Pro Val Ala Val Leu Gly Ile
225                 230                 235                 240

Asp Asn Ile Asn Glu His Glu Arg Thr Glu Ile Leu Gly Gly Arg Ser
                245                 250                 255

Lys Leu Ile Lys Asp Ile Ala Gly His Leu Leu Pro Met Ile Arg Ala
            260                 265                 270

Glu Gln Pro Gln Arg Gln Trp Ala Asp Arg Ser Arg Thr Val Leu Ala
        275                 280                 285

Gly Gln Ser Leu Gly Gly Ile Ser Ala Leu Met Gly Ala Arg Tyr Ala
    290                 295                 300

Pro Glu Thr Phe Gly Leu Val Leu Ser His Ser Pro Gln
305                 310                 315
```

<210> SEQ ID NO 30
<211> LENGTH: 4039
<212> TYPE: DNA
<213> ORGANISM: Escherichia coli
<220> FEATURE:
<221> NAME/KEY: CDS
<222> LOCATION: (1)..(285)
<221> NAME/KEY: CDS
<222> LOCATION: (370)..(1326)

<400> SEQUENCE: 30

```
cct tca atg tgg tgg acg cca gaa aga acc agt cga cca ggc ttg ttc       48
Pro Ser Met Trp Trp Thr Pro Glu Arg Thr Ser Arg Pro Gly Leu Phe
  1               5                  10                  15 agc gaa acc gat acc tca tgg gtg agt gag cat ctg ctt tct gcc cca      96
Ser Glu Thr Asp Thr Ser Trp Val Ser Glu His Leu Leu Ser Ala Pro
             20                  25                  30 ccg cag ggc gta cgt atc agc ctg tgc gtg gga tcg ctg gaa ggt tcg    144
Pro Gln Gly Val Arg Ile Ser Leu Cys Val Gly Ser Leu Glu Gly Ser
         35                  40                  45
```

| | | | | | | | | | | | | | | |
|---|---|---|---|---|---|---|---|---|---|---|---|---|---|---|
| aca | gtg | cct | cac | gtt | cag | cag | ctt | cac | cag | cgg | ctg | att | acc | gct ggc |
| Thr | Val | Pro | His | Val | Gln | Gln | Leu | His | Gln | Arg | Leu | Ile | Thr | Ala Gly |
| | 50 | | | | 55 | | | | 60 | | | | | |

192

| gtc | gaa | agc | cat | tgc | gca | atc | tac | acc | ggt | ggt | cac | gat | tac | gca tgg |
|---|---|---|---|---|---|---|---|---|---|---|---|---|---|---|
| Val | Glu | Ser | His | Cys | Ala | Ile | Tyr | Thr | Gly | Gly | His | Asp | Tyr | Ala Trp |
| 65 | | | | 70 | | | | | 75 | | | | | 80 |

240

| tgg | cgc | ggt | gca | ctg | att | gac | ggg | att | ggt | tta | cta | cag | ggt | tga |
|---|---|---|---|---|---|---|---|---|---|---|---|---|---|---|
| Trp | Arg | Gly | Ala | Leu | Ile | Asp | Gly | Ile | Gly | Leu | Leu | Gln | Gly | |
| | | | | 85 | | | | | 90 | | | | | 95 |

285 gttgacccac aaacactttc aggaaacggt acagacttcc tgaataaatc aaatagtcac    345 ctgcggaaaa ggaataatca tcag atg tat gcc cgc gag tat cgc tca aca       396
                       Met Tyr Ala Arg Glu Tyr Arg Ser Thr
                                              100

| cgc | ccg | cat | aaa | gcg | att | ttc | ttt | cat | ctt | tct | tgc | ctc | acc | ctt atc |
|---|---|---|---|---|---|---|---|---|---|---|---|---|---|---|
| Arg | Pro | His | Lys | Ala | Ile | Phe | Phe | His | Leu | Ser | Cys | Leu | Thr | Leu Ile |
| 105 | | | | | 110 | | | | | 115 | | | | 120 |

444

| tgt | agt | gcg | caa | gtt | tat | gcg | aag | ccg | gat | atg | cgg | cca | ctg | ggg ccg |
|---|---|---|---|---|---|---|---|---|---|---|---|---|---|---|
| Cys | Ser | Ala | Gln | Val | Tyr | Ala | Lys | Pro | Asp | Met | Arg | Pro | Leu | Gly Pro |
| | | | | 125 | | | | | 130 | | | | | 135 |

492

| aat | ata | gcc | gat | aaa | ggc | tcc | gtg | ttt | tac | cat | ttc | agc | gtc | acc tct |
|---|---|---|---|---|---|---|---|---|---|---|---|---|---|---|
| Asn | Ile | Ala | Asp | Lys | Gly | Ser | Val | Phe | Tyr | His | Phe | Ser | Val | Thr Ser |
| | | | 140 | | | | | 145 | | | | | 150 | |

540

| ttc | gac | tct | gtc | gat | ggc | aca | cgc | cat | tat | cgg | gta | tgg | acg | gcc gtg |
|---|---|---|---|---|---|---|---|---|---|---|---|---|---|---|
| Phe | Asp | Ser | Val | Asp | Gly | Thr | Arg | His | Tyr | Arg | Val | Trp | Thr | Ala Val |
| | | | 155 | | | | | 160 | | | | | 165 | |

588

| ccg | aat | aca | acc | gca | ccg | gca | tcg | ggt | tac | ccg | att | tta | tat | atg ctt |
|---|---|---|---|---|---|---|---|---|---|---|---|---|---|---|
| Pro | Asn | Thr | Thr | Ala | Pro | Ala | Ser | Gly | Tyr | Pro | Ile | Leu | Tyr | Met Leu |
| | 170 | | | | | 175 | | | | | 180 | | | |

636

| gac | ggt | aac | gca | gtt | atg | gat | cgc | ctg | gat | gac | gaa | ctg | ctc | aaa caa |
|---|---|---|---|---|---|---|---|---|---|---|---|---|---|---|
| Asp | Gly | Asn | Ala | Val | Met | Asp | Arg | Leu | Asp | Asp | Glu | Leu | Leu | Lys Gln |
| 185 | | | | | 190 | | | | | 195 | | | | | 200 |

684

| ttg | tca | gaa | aaa | aca | ccg | cca | gtg | atc | gtg | gct | gtc | ggg | tat | cag acc |
|---|---|---|---|---|---|---|---|---|---|---|---|---|---|---|
| Leu | Ser | Glu | Lys | Thr | Pro | Pro | Val | Ile | Val | Ala | Val | Gly | Tyr | Gln Thr |
| | | | | 205 | | | | | 210 | | | | | 215 |

732

| aac | ctc | cct | ttc | gat | ctc | aac | agc | agg | gct | tac | gac | tat | acg | cca gca |
|---|---|---|---|---|---|---|---|---|---|---|---|---|---|---|
| Asn | Leu | Pro | Phe | Asp | Leu | Asn | Ser | Arg | Ala | Tyr | Asp | Tyr | Thr | Pro Ala |
| | | | 220 | | | | | 225 | | | | | 230 | |

780

| gca | gaa | agc | aga | aaa | aca | gat | ctc | cac | tca | ggg | cgt | ttt | agc | cgt aag |
|---|---|---|---|---|---|---|---|---|---|---|---|---|---|---|
| Ala | Glu | Ser | Arg | Lys | Thr | Asp | Leu | His | Ser | Gly | Arg | Phe | Ser | Arg Lys |
| | 235 | | | | | 240 | | | | | 245 | | | |

828

| agt | ggt | ggc | agc | aac | aac | ttc | cgc | cag | tta | ctg | gaa | acg | cgt | att gcc |
|---|---|---|---|---|---|---|---|---|---|---|---|---|---|---|
| Ser | Gly | Gly | Ser | Asn | Asn | Phe | Arg | Gln | Leu | Leu | Glu | Thr | Arg | Ile Ala |
| 250 | | | | | 255 | | | | | 260 | | | | | |

876

| cca | aaa | gtg | gaa | cag | gga | ctg | aat | atc | gat | cgg | caa | cgc | cgc | ggc tta |
|---|---|---|---|---|---|---|---|---|---|---|---|---|---|---|
| Pro | Lys | Val | Glu | Gln | Gly | Leu | Asn | Ile | Asp | Arg | Gln | Arg | Arg | Gly Leu |
| 265 | | | | 270 | | | | | 275 | | | | | 280 | |

924

| tgg | ggc | cac | tcc | tac | ggc | ggc | ctc | ttc | gtg | ctg | gat | tcc | tgg | ctg tcc |
|---|---|---|---|---|---|---|---|---|---|---|---|---|---|---|
| Trp | Gly | His | Ser | Tyr | Gly | Gly | Leu | Phe | Val | Leu | Asp | Ser | Trp | Leu Ser |
| | | | | 285 | | | | | 290 | | | | | 295 |

972

| tcc | tct | tac | ttc | cgg | tcg | tac | tac | agc | gcc | agc | ccg | tcg | ttg | ggc aga |
|---|---|---|---|---|---|---|---|---|---|---|---|---|---|---|
| Ser | Ser | Tyr | Phe | Arg | Ser | Tyr | Tyr | Ser | Ala | Ser | Pro | Ser | Leu | Gly Arg |
| | | | 300 | | | | | 305 | | | | | 310 | |

1020

| ggt | tat | gat | gct | ttg | cta | agc | cgc | gtt | acg | gcg | gtt | gag | cct | ctg caa |
|---|---|---|---|---|---|---|---|---|---|---|---|---|---|---|
| Gly | Tyr | Asp | Ala | Leu | Leu | Ser | Arg | Val | Thr | Ala | Val | Glu | Pro | Leu Gln |
| | | | 315 | | | | | 320 | | | | | 325 | |

1068

| ttc | tgc | gcc | aaa | cac | ctg | gcg | ata | atg | gaa | ggc | tcg | gcg | aca | cag ggt |
|---|---|---|---|---|---|---|---|---|---|---|---|---|---|---|
| Phe | Cys | Ala | Lys | His | Leu | Ala | Ile | Met | Glu | Gly | Ser | Ala | Thr | Gln Gly |
| | 330 | | | | | 335 | | | | | 340 | | | |

1116

| gat | aac | cgg | gaa | acg | cat | gct | gtc | ggg | gtg | ctg | tcg | aaa | att | cat acc |

1164

-continued

| | | | | | | | | | | | | | | | |
|---|---|---|---|---|---|---|---|---|---|---|---|---|---|---|---|
| Asp | Asn | Arg | Glu | Thr | His | Ala | Val | Gly | Val | Leu | Ser | Lys | Ile | His | Thr |
| 345 | | | | 350 | | | | | 355 | | | | | 360 | |

| acc | ctc | act | ata | ctg | aaa | gat | aaa | ggc | gtc | aat | gcc | gta | ttt | tgg | gat | 1212 |
|---|---|---|---|---|---|---|---|---|---|---|---|---|---|---|---|---|
| Thr | Leu | Thr | Ile | Leu | Lys | Asp | Lys | Gly | Val | Asn | Ala | Val | Phe | Trp | Asp | |
| | | | | 365 | | | | | 370 | | | | | 375 | | |

| ttc | ccc | aac | ctg | gga | cac | ggg | ccg | atg | ttc | aat | gcc | tcc | ttt | cgc | cag | 1260 |
|---|---|---|---|---|---|---|---|---|---|---|---|---|---|---|---|---|
| Phe | Pro | Asn | Leu | Gly | His | Gly | Pro | Met | Phe | Asn | Ala | Ser | Phe | Arg | Gln | |
| | | | 380 | | | | | 385 | | | | | 390 | | | |

| gca | ctg | tta | gat | atc | agt | ggt | gaa | aac | gca | aat | tac | aca | gca | ggt | tgt | 1308 |
|---|---|---|---|---|---|---|---|---|---|---|---|---|---|---|---|---|
| Ala | Leu | Leu | Asp | Ile | Ser | Gly | Glu | Asn | Ala | Asn | Tyr | Thr | Ala | Gly | Cys | |
| | | 395 | | | | | 400 | | | | | 405 | | | | |

| cat | gag | tta | agc | cac | taa | acactgcccg | cttttacgcg | ggcagtacgc | | 1356 |
|---|---|---|---|---|---|---|---|---|---|---|
| His | Glu | Leu | Ser | His | | | | | | |
| | 410 | | | | | | | | | |

| | | | | |
|---|---|---|---|---|
| ctgaaacact | acgatcagaa | tgatgcggta | actccggcat | agtaagcccg | gcctggctcg | 1416 |
| ttataggtat | tcgccccttc | agaagatcgg | aagatctgtt | tattgaggat | attactgacg | 1476 |
| ccgacattaa | gacgcagatt | tttattaata | tcgtaattga | agttcgtccc | caccagtgaa | 1536 |
| taagcgccca | gctctttacc | tgacagaccg | ccagtatctt | cactgcgggt | tccgcatga | 1596 |
| gtacgcggtt | tttgtctgcc | atataacgtc | cagttgacgc | tggcagaaaa | cgcctgggtg | 1656 |
| atggtccagt | taagcgagtt | attgatagta | tatttcggga | tgaccgacag | aggattaccg | 1716 |
| gtgtctttt | gctccgaagt | gatcatccat | gtggcattgg | tattccagtt | cagacgatct | 1776 |
| ttcaccagtg | ggaaagacat | actggcttcg | ataccgtcca | ccagagcttt | ccgccattc | 1836 |
| tgccacttga | ggatatatgc | gcctgaagcg | gtttgcccga | taacgttatc | cccggccacg | 1896 |
| atcttattct | ggtaatcatt | gcggaagtag | gtcacacttg | cgtggtaatc | ttcccaggtg | 1956 |
| aactccagcc | caatttcttt | attgacgctg | atttccggat | cgagatcttt | attaccgatc | 2016 |
| aggtagcacc | cgcctgatgt | aatatctttt | ggacagccat | tgcctttcga | gtagagcaga | 2076 |
| tagccttcac | tggattgata | caggtttggg | gctttaaagg | ttcgggcaac | ccctgctttg | 2136 |
| actttgaaat | aatcgcccaa | ttcctgcgaa | agattcagac | tggggctgaa | gttcccgccg | 2196 |
| gagtcgctga | gataatcaaa | gcgcaggccg | ggaatgatat | tcgtgccagg | aaccggctca | 2256 |
| atgttatctt | caatatacag | cgcactgatt | tgagaatgat | ttttactgct | gcgatccgca | 2316 |
| gcagagccag | aaataccgct | gatatcactg | tcattcaccg | tcaggctggt | agaggaagga | 2376 |
| tcatcgagct | tatcgcggtt | ccactctgca | ccaacggtca | gcgtttgatc | aaccatcaca | 2436 |
| ttcaaaggaa | tattaagctc | gccgctggtt | cgccaggaac | tcaggcgatt | ggtcgtaaac | 2496 |
| ttttcacccg | ctaaaatacg | cccttcacca | ccgccggata | tccttcatt | catgcgggta | 2556 |
| ttattggttt | tctcgtaata | aacaccaaag | cgactttgtc | cccagtccca | gataccatta | 2616 |
| tgcgtaatgc | cataattctg | tcggtacagg | cggctcgtct | cttgtgccgg | attttgccag | 2676 |
| gcttttcggt | aactgcactg | gaagaactgt | tttgcgtatc | gccgcataga | tattcccctg | 2736 |
| gcggctatat | ccggcttcga | aatcgagaat | ctgctgcgga | tttaatttcc | acgagacaac | 2796 |
| gccgttaata | tctttgttac | gtaccccttc | atgcccggct | gcgttttttcg | taccgaccgg | 2856 |
| agaattaata | tcccaactgt | cagcatccgt | tttattcaga | ttaccataca | aacgcgtggt | 2916 |
| aagagcatta | ccagccagag | gcccactaag | gctgaaattg | gcgcgacgcg | tagcgccctc | 2976 |
| atcgctactt | tccggctgat | tggtgtataa | cgacagcgaa | ccgtgccagt | cgttggtggg | 3036 |
| acgtttggta | atgatgttca | ccaccccccc | ggctgcccc | gaaccgtagc | gcgccgccgc | 3096 |
| agggccgcgg | atcacttcaa | tacgctcaac | ctgttccggt | ggcacccagt | tggtgtcacc | 3156 |

-continued

```
gcgggtatca cgctctccac gccagctata acgcacggag ttacgtgacg tcaccggtac    3216
accatcaatt aaaattaagg tgttttccgg ccccatacca cgaatatcga tctggcggtt    3276
gttaccgcgt gtgcccgagg cgctattgcc ggtaagattg acgccaggca ttttacgaat    3336
aatatctgaa aggtcgttta ccggagggt cttttttaata tcctcgctgg taataaccga    3396
cacgcccggc tgctgtttta atacctgctc agcggtggct tccaccacca gagtctcgtc    3456
attatcatcg tcggaggatt tggctactga tacctggcta ttcaacccaa ccaggagcac    3516
agttagcgac cagaggattt tgttaattct catacctatt ccctaataaa tgcctaactt    3576
aaaatgtttg atcgttaagc tcacatcctt gccagatatt ttttactgcc attattgttt    3636
ttatataaga atgataatta atatcattta gcaaagaaaa aagcaatccc tcacaagata    3696
aatatatcga tttttcataa atatcaaatt gatatataac atatgttttt tatttcattg    3756
tacttcagtc aaataaattt ctgaagcact gctagtagtg ccagttcagc tttcttttg    3816 actcattccg gcaaagtcag taccgttcat cttttgtact gatgttgcca ctggaaaatc    3876
ggtgcgcttg tcgatcatcg ggaattttgt cacaatttct aacggatagt gttcacattg    3936 tttctaaccct gcattttcag acacgggcgc tgcttatgta tataagatca gcatcactag    3996
gtctttctgc aacactactg ctttcaacaa ggtcaggcat ttc                       4039
```

<210> SEQ ID NO 31
<211> LENGTH: 94
<212> TYPE: PRT
<213> ORGANISM: Escherichia coli

<400> SEQUENCE: 31

```
Pro Ser Met Trp Trp Thr Pro Glu Arg Thr Ser Arg Pro Gly Leu Phe
  1               5                  10                  15

Ser Glu Thr Asp Thr Ser Trp Val Ser Glu His Leu Leu Ser Ala Pro
             20                  25                  30

Pro Gln Gly Val Arg Ile Ser Leu Cys Val Gly Ser Leu Glu Gly Ser
         35                  40                  45

Thr Val Pro His Val Gln Gln Leu His Gln Arg Leu Ile Thr Ala Gly
     50                  55                  60

Val Glu Ser His Cys Ala Ile Tyr Thr Gly Gly His Asp Tyr Ala Trp
 65                  70                  75                  80

Trp Arg Gly Ala Leu Ile Asp Gly Ile Gly Leu Leu Gln Gly
                 85                  90
```

<210> SEQ ID NO 32
<211> LENGTH: 318
<212> TYPE: PRT
<213> ORGANISM: Escherichia coli

<400> SEQUENCE: 32

```
Met Tyr Ala Arg Glu Tyr Arg Ser Thr Arg Pro His Lys Ala Ile Phe
  1               5                  10                  15

Phe His Leu Ser Cys Leu Thr Leu Ile Cys Ser Ala Gln Val Tyr Ala
             20                  25                  30

Lys Pro Asp Met Arg Pro Leu Gly Pro Asn Ile Ala Asp Lys Gly Ser
         35                  40                  45

Val Phe Tyr His Phe Ser Val Thr Ser Phe Asp Ser Val Asp Gly Thr
     50                  55                  60

Arg His Tyr Arg Val Trp Thr Ala Val Pro Asn Thr Thr Ala Pro Ala
 65                  70                  75                  80
```

```
Ser Gly Tyr Pro Ile Leu Tyr Met Leu Asp Gly Asn Ala Val Met Asp
                85                  90                  95

Arg Leu Asp Asp Glu Leu Leu Lys Gln Leu Ser Glu Lys Thr Pro Pro
            100                 105                 110

Val Ile Val Ala Val Gly Tyr Gln Thr Asn Leu Pro Phe Asp Leu Asn
            115                 120                 125

Ser Arg Ala Tyr Asp Tyr Thr Pro Ala Ala Glu Ser Arg Lys Thr Asp
130                 135                 140

Leu His Ser Gly Arg Phe Ser Arg Lys Ser Gly Ser Asn Asn Phe
145                 150                 155                 160

Arg Gln Leu Leu Glu Thr Arg Ile Ala Pro Lys Val Glu Gln Gly Leu
            165                 170                 175

Asn Ile Asp Arg Gln Arg Arg Gly Leu Trp Gly His Ser Tyr Gly Gly
            180                 185                 190

Leu Phe Val Leu Asp Ser Trp Leu Ser Ser Ser Tyr Phe Arg Ser Tyr
            195                 200                 205

Tyr Ser Ala Ser Pro Ser Leu Gly Arg Gly Tyr Asp Ala Leu Leu Ser
210                 215                 220

Arg Val Thr Ala Val Glu Pro Leu Gln Phe Cys Ala Lys His Leu Ala
225                 230                 235                 240

Ile Met Glu Gly Ser Ala Thr Gln Gly Asp Asn Arg Glu Thr His Ala
            245                 250                 255

Val Gly Val Leu Ser Lys Ile His Thr Thr Leu Thr Ile Leu Lys Asp
            260                 265                 270

Lys Gly Val Asn Ala Val Phe Trp Asp Phe Pro Asn Leu Gly His Gly
            275                 280                 285

Pro Met Phe Asn Ala Ser Phe Arg Gln Ala Leu Leu Asp Ile Ser Gly
            290                 295                 300

Glu Asn Ala Asn Tyr Thr Ala Gly Cys His Glu Leu Ser His
305                 310                 315

<210> SEQ ID NO 33
<211> LENGTH: 3292
<212> TYPE: DNA
<213> ORGANISM: Escherichia coli

<400> SEQUENCE: 33
ccgctgcggt tgattgccgg atgcggcgtg aacgccttat ccggcctaca atcattgcaa     60
attcaataaa ttgcagcgtt ctgtaggctg gataagatgc gtcagcatcg catccggcaa    120
aggcagatct cagcgatagc gccggcttag tcagatttaa tctgcgcgcg tggtggatat    180
tttttcagga tctccatata cgcgtgcatt tcggtctgta gcggtacacc catcggaata    240
tggcgcacgc cgatagagtc gctttcctgc ggatcggtgt acaggttaaa caccgacgat    300
cccgccgttt gcattactgt gccggtgaat ccaccctgat atccgctctg ggtataagcg    360
taaggttgct gaatcaggac gtgatacttg aactcatcca tacgcacagc agaaagttta    420
ccgttgagga agtagtgctc ggccttacgg ttagactgac catttgttcc caggaagaaa    480
gatgtctggt ccacaccatc gataaaggtg gttttcggta ctaaattcgc tactttcgcc    540
ccaggatgcc ccgccagatc cagcgccgta gggaagagat ccgccagatc gacaatgccg    600
tcagatttac gcggttggat catgcctttc cagtaaacga aggttggcac acgaacgccg    660
ccttcccatg tagaaccttt cgcaccgcgg aacggcgtgc gaccgtgcgg cggaacttcg    720
gcttccggac cgttatcaga ggtgaacaca atcagcgtgt tatcaagctg accgttttc    780
```

```
tccagtgctt tatacagatt ggcgaagata tcgttcatct ccaccatgca gtcgccgtaa      840
gaggtgcgcg ccggagagct acccgcatat ttggcgttcg ggtagttatc gaagtgacag      900
ccgcgagtgc cgtaatagag gaagaaaggc ttatcactct tcgccatctt gtcgaggaac      960
ttaacgccat attccatcca gcgttgatcc aggtcttcca tatatttcgg cgtaatgtcg     1020
gcaatggctt cctgttcacc gccgcgcacg gcatgaacgt catctttgct gaacggcagt     1080
ttttggatgt attcagaacg agccgggctc agggcgactt ccgggttgac atgaacatca     1140
cgccattcgg tatacatatc ggacaccgag ttaaagccgc ggaaatcatc aaagccaacg     1200
ttctgcggct gcgactcttt gttttccccc atatgccatt tcccgatagc ctgggtgacg     1260
tagccctgat cgtgcagcaa ctgcggcagc gtggttaacc cttgcagacc gcccggttgc     1320
ccgtacattg gcggcatcag aatgccgtgg tggatggagt attgtccggt gagaatcgtg     1380
gcgcgggttg gggaagaact cggttgagaa tacgccgaag ttaaaatcag cccctggctg     1440
gcaacggcgt cgatatctgg tgtagggtta cccaccgcca cgccgccgcc gttaaagcca     1500
acgtccatcc agcccacatc atccagcaag aaaacaacca cgttcggttt cttaccggtt     1560 ttttttctcaa gttccgccag tttctgctgg gtttcttttgt cttgtgcagg atgctgcatc     1620
accggcatca tgttgtcggc aatagtggtc gccggtttaa ccagatactg gtttgggtga     1680
tcgtatccgg caaagccttt gcgtgcggtg gcggttgacg gggtatctgc tgcgctggct     1740
atgagaggaa gagctgcggc gacagcaaca caagaagtt tgggtgaaaa cgaaaattcc     1800
atgcaaaatg ctccggtttc atgtcgtcaa aatgatgacg taattaagca ttgataattg     1860
agatccctct ccctgacagg atgattgcat aaataatagt gataaaaata aattatttat     1920
ttatccagaa atgaattgaa aaatcaggag agcattttca atcctacctc tggcgcaggt     1980
gatattgtaa ggcggtgatg ttatatcgcg ttgattattg atgctgtttt tagttttaac     2040
ggcattaata tatatgttat taattgaatg acttttatta ttcattatat atatgtgtag     2100
aattgtgcgc aggagaaata ttcactcagg aagttattac tcaggaagca aagaggatta     2160
cagaattatc tcataacaag tgttaaggga tgttatttcc cggttctctg tggcataata     2220
aacgagtaga tgctcattcc atctcttatg ttcgccttag tgcctcataa actccggaat     2280
gacgcagagc cgtttacggt gcttatcgtc cactgacaga tgtcgcttat gcctcatcag     2340
acaccatgga cacaacgttg agtgaagcac ccacttgttg tcatacagac ctgttttaac     2400
gcctgctccg taataagagc aggcgttttt ttatatatca gaaaggcccc ggaggtgctt     2460
gcctccgggt gagaaagagc tactgtggcg ggttgttctg caacgttaac atcaaaccgt     2520
cgcgacgcat cgctgcggct tcttccggct tgtgcagtct gtccagcgcg tcggcaagcc     2580
atgcgtaatc gtaggcgtcc ggacgttgtt tcagcgctgc gcggaaggcg agcgatgctt     2640
cctgccattc tccgtgtttc atcagcgact gacccagtgt gctccacaac agcgggcgat     2700
cgcccacgtt tttgatctgt tggcgcagca cttttttccaa gctgttcccg ggttaattgg     2760
gttttcagac gccggggatc ggcagcagca ggccgaatcg tcatactggc gtttcaggcc     2820
atcgatgata atttgctggg cagtatcatg atcgtcacac tcaataagat gttccgccat     2880
tgccacctgc aaggccacct gatgacgcgt tttccggctt tggttttttcc accagttacg     2940 caaaccttca ctaccgttat cggcacgcgc ctgatccatc aggccaatcc atgcctgttg     3000
ttccagcatt gcacgatgtt cttcatcacc aacatgggct ttcgccattg atgggatgat     3060
atccagcagc gaactccatg caccagtgcg gatatacgcc tgttccgcca gacgtaatac     3120
ttccggatgg cgtggcgtaa cttccagcag cttatccacg ccgtgacgtg ctgcatggtt     3180
```

```
ttcattacgg gccagttgca gacgtacacg ggtgatttct accggaatgg tgtcattgcc      3240
ggccagctcc gctgcgcgtt ccagatgttg gttggcgcgt gcttcagcat cc              3292
```

```
<210> SEQ ID NO 34
<211> LENGTH: 11165
<212> TYPE: DNA
<213> ORGANISM: Escherichia coli
<220> FEATURE:
<221> NAME/KEY: CDS
<222> LOCATION: (3791)..(4834)
<221> NAME/KEY: CDS
<222> LOCATION: (10459)..(10776)
<221> NAME/KEY: CDS
<222> LOCATION: (10134)..(10427)
<221> NAME/KEY: CDS
<222> LOCATION: (9836)..(10081)
<221> NAME/KEY: CDS
<222> LOCATION: (7816)..(9480)
<221> NAME/KEY: CDS
<222> LOCATION: (4878)..(7802)
<221> NAME/KEY: CDS
<222> LOCATION: (3460)..(3702)
<221> NAME/KEY: CDS
<222> LOCATION: (3054)..(3407)
<221> NAME/KEY: CDS
<222> LOCATION: (2613)..(3041)
<221> NAME/KEY: CDS
<222> LOCATION: (2198)..(2530)
<221> NAME/KEY: CDS
<222> LOCATION: (1939)..(2196)
<221> NAME/KEY: CDS
<222> LOCATION: (1573)..(1893)
<221> NAME/KEY: CDS
<222> LOCATION: (1102)..(1485)
<221> NAME/KEY: CDS
<222> LOCATION: (2)..(1099)

<400> SEQUENCE: 34
```

```
c agc gat atg cag cgc ggt atc cag gct gca acg gct gca ctt cag ggc     49
  Ser Asp Met Gln Arg Gly Ile Gln Ala Ala Thr Ala Ala Leu Gln Gly
   1               5                  10                  15 ctg gtg ggc ggc aat atg gca ggc gcg ctg gca ggt gct tca gcg ccg       97
Leu Val Gly Gly Asn Met Ala Gly Ala Leu Ala Gly Ala Ser Ala Pro
             20                  25                  30 gag ctg gcg aac atc atc ggt cat cac gcg ggt att gat gac aat aca      145
Glu Leu Ala Asn Ile Ile Gly His His Ala Gly Ile Asp Asp Asn Thr
 35                  40                  45 gcg gca aaa gcc att gcc cat gcc att ctc ggt ggt gtg aca gca gcc      193
Ala Ala Lys Ala Ile Ala His Ala Ile Leu Gly Gly Val Thr Ala Ala
         50                  55                  60 ctt cag ggc aac agt gcg gca gca ggc gca att ggt gcg ggt act ggt      241
Leu Gln Gly Asn Ser Ala Ala Ala Gly Ala Ile Gly Ala Gly Thr Gly
 65                  70                  75                  80 gaa gtg atc gcg tca gcc att gcg aaa agc ctc tac ccg ggc gta gat      289
Glu Val Ile Ala Ser Ala Ile Ala Lys Ser Leu Tyr Pro Gly Val Asp
                 85                  90                  95 ccg tcg aaa ctg aca gaa gat cag aag caa act gta agc acg ctg gca      337
Pro Ser Lys Leu Thr Glu Asp Gln Lys Gln Thr Val Ser Thr Leu Ala
            100                 105                 110 acg ctg tca gcg ggt atg gcc ggc ggc att gcc agt ggc gat gtg gct      385
Thr Leu Ser Ala Gly Met Ala Gly Gly Ile Ala Ser Gly Asp Val Ala
        115                 120                 125 ggc gcg gct gct gga gct ggt gcc ggg aag aac gtt gtt gag aat aat      433
Gly Ala Ala Ala Gly Ala Gly Ala Gly Lys Asn Val Val Glu Asn Asn
    130                 135                 140 gcg ctg agt ctg gtt gcc aga ggc tgt gcg gtc gca gca cct tgc agg      481
```

|   |   |   |   |   |   |   |   |   |   |   |   |   |   |   |   |   |
|---|---|---|---|---|---|---|---|---|---|---|---|---|---|---|---|---|
| Ala | Leu | Ser | Leu | Val | Ala | Arg | Gly | Cys | Ala | Val | Ala | Ala | Pro | Cys | Arg | |
| 145 | | | | 150 | | | | 155 | | | | 160 | | | | |

```
act aaa gtt gca gag cag ttg cta gaa atc ggg gcg aaa gcg ggc atg      529
Thr Lys Val Ala Glu Gln Leu Leu Glu Ile Gly Ala Lys Ala Gly Met
            165                 170                 175 gcc ggg ctt gcc ggg gcg gca gtc aag gat atg gcc gac agg atg acc      577
Ala Gly Leu Ala Gly Ala Ala Val Lys Asp Met Ala Asp Arg Met Thr
        180                 185                 190 tcc gat gaa ctg gag cat ctg att acc ctg caa atg atg ggt aat gat      625
Ser Asp Glu Leu Glu His Leu Ile Thr Leu Gln Met Met Gly Asn Asp
    195                 200                 205 gag atc act act aag tat ctc agt tcg ttg cat gat aag tac ggt tcc      673
Glu Ile Thr Thr Lys Tyr Leu Ser Ser Leu His Asp Lys Tyr Gly Ser
210                 215                 220 ggg gct gcc tcg aat ccg aat atc ggt aaa gat ctg acc gat gcg gaa      721
Gly Ala Ala Ser Asn Pro Asn Ile Gly Lys Asp Leu Thr Asp Ala Glu
225                 230                 235                 240 aaa gta gaa ctg ggc ggt tcc ggc tca gga acc ggt aca cca cca cca      769
Lys Val Glu Leu Gly Gly Ser Gly Ser Gly Thr Gly Thr Pro Pro Pro
                245                 250                 255 tcg gaa aat gat cct aag cag caa aat gaa aaa act gta gat aag ctt      817
Ser Glu Asn Asp Pro Lys Gln Gln Asn Glu Lys Thr Val Asp Lys Leu
            260                 265                 270 aat cag aag caa gaa agt gcg att aag aag atc gat aac act ata aaa      865
Asn Gln Lys Gln Glu Ser Ala Ile Lys Lys Ile Asp Asn Thr Ile Lys
        275                 280                 285 aat gct ctg aaa gat cat gat att att gga act ctc aag gat atg gat      913
Asn Ala Leu Lys Asp His Asp Ile Ile Gly Thr Leu Lys Asp Met Asp
    290                 295                 300 ggt aag cca gtt cct aaa gag aat gga gga tat tgg gat cat atg cag      961
Gly Lys Pro Val Pro Lys Glu Asn Gly Gly Tyr Trp Asp His Met Gln
305                 310                 315                 320 gaa atg caa aat acg ctc aga gga tta aga aat cat gcg gat acg ttg     1009
Glu Met Gln Asn Thr Leu Arg Gly Leu Arg Asn His Ala Asp Thr Leu
                325                 330                 335 aaa aac gtc aac aat cct gaa gct cag gct gcg tat ggc aga gca aca     1057
Lys Asn Val Asn Asn Pro Glu Ala Gln Ala Ala Tyr Gly Arg Ala Thr
            340                 345                 350 gat gct att aat aaa ata gaa tca gcc ttg aaa gga tat gga at atg     1104
Asp Ala Ile Asn Lys Ile Glu Ser Ala Leu Lys Gly Tyr Gly     Met
        355                 360                 365 att acc tta cgt aaa ttg att gga aac atc aat atg aca aaa gag cct     1152
Ile Thr Leu Arg Lys Leu Ile Gly Asn Ile Asn Met Thr Lys Glu Pro
    370                 375                 380 gag caa caa tca ccg ctt gaa ctc tgg ttc gaa cgt atc ata gat gtg     1200
Glu Gln Gln Ser Pro Leu Glu Leu Trp Phe Glu Arg Ile Ile Asp Val
385                 390                 395 cct ctt gaa aag tta aca gtg gaa gat ctt tgc cgc gct atc cga caa     1248
Pro Leu Glu Lys Leu Thr Val Glu Asp Leu Cys Arg Ala Ile Arg Gln
400                 405                 410                 415 aat tta tgt att gat cag ttg atg cca aga gtg ttg gaa gtt cta act     1296
Asn Leu Cys Ile Asp Gln Leu Met Pro Arg Val Leu Glu Val Leu Thr
                420                 425                 430 aaa gag ccg tta gcg ggt gaa tat tac gat ggt gaa cta att gca gct     1344
Lys Glu Pro Leu Ala Gly Glu Tyr Tyr Asp Gly Glu Leu Ile Ala Ala
            435                 440                 445 tta tca acg ata aaa gga gaa gat cta aaa gat cag aaa agt acc ttt     1392
Leu Ser Thr Ile Lys Gly Glu Asp Leu Lys Asp Gln Lys Ser Thr Phe
        450                 455                 460
```

```
acc caa ata agg caa ctt ata aac cag cta gaa ccg tca gat att aac     1440
Thr Gln Ile Arg Gln Leu Ile Asn Gln Leu Glu Pro Ser Asp Ile Asn
    465                 470                 475 gat gat tta aga aaa gat ata tta aaa atc aat cag ata att gta         1485
Asp Asp Leu Arg Lys Asp Ile Leu Lys Ile Asn Gln Ile Ile Val
480                 485                 490 taactaatcc cggccactga gccgagatct tctttgtgtg ccgggcatgt tcagcagctt   1545
gggggtgaaa gtccctgtc cagcctg atg gtg gcg aag gcg ttc gcg tac gca   1599
                              Met Val Ala Lys Ala Phe Ala Tyr Ala
                                      495                 500 ctt aac cag tgg ccg gca ctg acg tac tat gcg aac gat ggc tgg gtg    1647
Leu Asn Gln Trp Pro Ala Leu Thr Tyr Tyr Ala Asn Asp Gly Trp Val
        505                 510                 515 gaa atc gac aac aac atc gct gaa aat gcc ctg cgg gcg gtc agt ctg    1695
Glu Ile Asp Asn Asn Ile Ala Glu Asn Ala Leu Arg Ala Val Ser Leu
520                 525                 530                 535 ggt cgt aaa aac ttc ctg ttc ttc ggc tct gac cat ggt ggt gag cgg    1743
Gly Arg Lys Asn Phe Leu Phe Phe Gly Ser Asp His Gly Gly Glu Arg
                540                 545                 550 gga gcg cta ctg tac agc ctg atc ggg acg tgc aaa ctg aat gac gtg    1791
Gly Ala Leu Leu Tyr Ser Leu Ile Gly Thr Cys Lys Leu Asn Asp Val
            555                 560                 565 gat cca gaa agc tac ctt cgc cat gtg ctt gcc gtc ata gca gac tgg    1839
Asp Pro Glu Ser Tyr Leu Arg His Val Leu Ala Val Ile Ala Asp Trp
        570                 575                 580 ccg gtc aac cgg gtc agc gaa ctg ctt ccg tgg cgc ata gca ctg cca    1887
Pro Val Asn Arg Val Ser Glu Leu Leu Pro Trp Arg Ile Ala Leu Pro
585                 590                 595 gct gaa taacacatcc ccgtcaatac ggccctcgct gtacgcttac agaaa atg ctg  1944
Ala Glu                                                    Met Leu
600 atg tct gta cag aaa gaa aag aac gtc gca gag agt gtg gta tct gaa    1992
Met Ser Val Gln Lys Glu Lys Asn Val Ala Glu Ser Val Val Ser Glu
        605                 610                 615 acg cat acc ggc gac agc gta tat gct tcc ctg ttt gaa aaa att aac    2040
Thr His Thr Gly Asp Ser Val Tyr Ala Ser Leu Phe Glu Lys Ile Asn
620                 625                 630                 635 ctg aat ccg gta tct gcc ctg agt gca ctg gat aac cct ttc cgg tca    2088
Leu Asn Pro Val Ser Ala Leu Ser Ala Leu Asp Asn Pro Phe Arg Ser
                640                 645                 650 gca gat aac gcg act ggc aga att acc tcc agc ata caa cct gcg gtg    2136
Ala Asp Asn Ala Thr Gly Arg Ile Thr Ser Ser Ile Gln Pro Ala Val
            655                 660                 665 cag tgc gca gct gct gca gca act gag ggt tct tgt ccc cgg caa tcc    2184
Gln Cys Ala Ala Ala Ala Thr Glu Gly Ser Cys Pro Arg Gln Ser
        670                 675                 680 ccg tgt tca gga a atg gtg gat aac tgg cag aag agt gta agg agt cgt  2233
Pro Cys Ser Gly   Met Val Asp Asn Trp Gln Lys Ser Val Arg Ser Arg
685                   690                 695 gcg ctc ccg gaa gag gcg atg acg ggc tgg aac gaa ggc atg atc cgc    2281
Ala Leu Pro Glu Glu Ala Met Thr Gly Trp Asn Glu Gly Met Ile Arg
700                 705                 710                 715 tta cag cag ttg gct gag cgc ctg aac cgt cag gat gaa cag cgg gga    2329
Leu Gln Gln Leu Ala Glu Arg Leu Asn Arg Gln Asp Glu Gln Arg Gly
                720                 725                 730 aaa tac atg acg gtc agt gaa ctg aaa acg gag gtg ttt ggc atc atg    2377
Lys Tyr Met Thr Val Ser Glu Leu Lys Thr Glu Val Phe Gly Ile Met
            735                 740                 745 cag gct ttt aac cgg cat atc ccg gcg gaa gag cag tta cgt cgc tac    2425
```

-continued

```
            Gln Ala Phe Asn Arg His Ile Pro Ala Glu Glu Gln Leu Arg Arg Tyr
                            750                 755                 760 ggt gaa gtc cgt aac cag aat ggc agt gaa cag cag caa aaa cag gct        2473
Gly Glu Val Arg Asn Gln Asn Gly Ser Glu Gln Gln Gln Lys Gln Ala
765                 770                 775 gaa atg gcg cta aat cag tta att aac cgt tat cag atg ata cgt gca        2521
Glu Met Ala Leu Asn Gln Leu Ile Asn Arg Tyr Gln Met Ile Arg Ala
780                 785                 790                 795 ggc aaa caa tagtggtagc cataatgcag gagcaaagcc tgaatcagga                2570
Gly Lys Gln agagttattc tgactgagtt tggttttctg gcgattcttg tg atg gtg gga tgt         2624
                                               Met Val Gly Cys
                                                           800 gct tgg tta gct gaa cag gcc ttt tcc gac cat gcg ctt tca cca cac        2672
Ala Trp Leu Ala Glu Gln Ala Phe Ser Asp His Ala Leu Ser Pro His
            805                 810                 815 agt gct tgg ccg tac agt gca tcg cgc gat gcc ggg ctg gcc gat acg        2720
Ser Ala Trp Pro Tyr Ser Ala Ser Arg Asp Ala Gly Leu Ala Asp Thr
820                 825                 830 ggc gcg ggc ggc tat ccc act tgt aaa cag cgg tgg gcc gac gac acc        2768
Gly Ala Gly Gly Tyr Pro Thr Cys Lys Gln Arg Trp Ala Asp Asp Thr
835                 840                 845                 850 gtt ggg ctg aaa gcc cgt cta ctg caa ctt cct gcc cta gat atc tgg        2816
Val Gly Leu Lys Ala Arg Leu Leu Gln Leu Pro Ala Leu Asp Ile Trp
            855                 860                 865 acg gcg ttt aaa aaa atc gac cag tcg cag gta gtg tat gaa gag gcc        2864
Thr Ala Phe Lys Lys Ile Asp Gln Ser Gln Val Val Tyr Glu Glu Ala
870                 875                 880 gtg ctg cgc tcg cgg gtc agt gaa cga aat atg cag gta tcg cag aat        2912
Val Leu Arg Ser Arg Val Ser Glu Arg Asn Met Gln Val Ser Gln Asn
            885                 890                 895 ggg cgc gtt tat cca agc tat ggc ggt aac gtt gat ggc acc gtc gcc        2960
Gly Arg Val Tyr Pro Ser Tyr Gly Gly Asn Val Asp Gly Thr Val Ala
900                 905                 910 aat gcc gcc acc cgg ttg gca tcc ggc gct aga aat atc ctc ggc agc        3008
Asn Ala Ala Thr Arg Leu Ala Ser Gly Ala Arg Asn Ile Leu Gly Ser
915                 920                 925                 930 ata gcg gca tgt acg gca ttc gac agc gtg cgt taggcactac cg atg gta     3059
Ile Ala Ala Cys Thr Ala Phe Asp Ser Val Arg                Met Val
            935                 940 cag gcg cag ctg caa ata gcg ctg gtg atc tgt att ccg ctg ata acg        3107
Gln Ala Gln Leu Gln Ile Ala Leu Val Ile Cys Ile Pro Leu Ile Thr
945                 950                 955 ctc tgt tcg gcg tgg gat gtg aaa gta gtg atg acg ctg acg ttt gtg        3155
Leu Cys Ser Ala Trp Asp Val Lys Val Val Met Thr Leu Thr Phe Val
960                 965                 970                 975 cag ttt gca cta ttt ttc ctc acc ttt tgg tgg gaa ctg gca cgg tgg        3203
Gln Phe Ala Leu Phe Phe Leu Thr Phe Trp Trp Glu Leu Ala Arg Trp
            980                 985                 990 ctt gat agc tgg ctg ctg gat gtg ctc tac aac agc gat acc cac agt        3251
Leu Asp Ser Trp Leu Leu Asp Val Leu Tyr Asn Ser Asp Thr His Ser
            995                 1000                1005 agc tgg aat tta gcc ggg atc cag aat acg cag gat gac gtg att atc        3299
Ser Trp Asn Leu Ala Gly Ile Gln Asn Thr Gln Asp Asp Val Ile Ile
        1010                1015                1020 aat ctg gtg atg agg ttg atg ttt ctg gtg ttg ccg aca ttc tgg ctg        3347
Asn Leu Val Met Arg Leu Met Phe Leu Val Leu Pro Thr Phe Trp Leu
    1025                1030                1035 ggg gcg atg acg tgg gct gga gtg agg gtt ggc gtg gcg ctg aat gga        3395
```

-continued

```
Gly Ala Met Thr Trp Ala Gly Val Arg Val Gly Val Ala Leu Asn Gly
1040                1045                1050                1055 gcg ctg gcg gga tgattgggag gtgattcgcc aatctcactt tcctatacac          3447
Ala Leu Ala Gly atataaaatg ta atg aaa tat ctc ttt ttt gag aat ata cat tct ata ttt    3498
              Met Lys Tyr Leu Phe Phe Glu Asn Ile His Ser Ile Phe
              1060                1065                1070 tta aca ttc agt ctc ttc cga aca tct gtg tcg cct gat ttc cca atg      3546
Leu Thr Phe Ser Leu Phe Arg Thr Ser Val Ser Pro Asp Phe Pro Met
1075                1080                1085 att ttt gca ttg ccc tca atc att tta ggt caa ttt acg acc aac caa      3594
Ile Phe Ala Leu Pro Ser Ile Ile Leu Gly Gln Phe Thr Thr Asn Gln
    1090                1095                1100 tta act aac ttt gtg ata tgt atg ggt aac acc gtt gaa cgt cgg ctg      3642
Leu Thr Asn Phe Val Ile Cys Met Gly Asn Thr Val Glu Arg Arg Leu
1105                1110                1115                1120 ggt gtt gtt cat aat ccc ttt aaa agg tct ggg gat ggc cat gac ctc      3690
Gly Val Val His Asn Pro Phe Lys Arg Ser Gly Asp Gly His Asp Leu
                1125                1130                1135 agg gcg gta gcg tgaccaaagt tcatatccat accaattatt tttatttaaa          3742
Arg Ala Val Ala
            1140 atatcaactt attcgagttg ttttatttag ttcaaagaag gtatcaaa ttg ata gtt     3799
                                                     Leu Ile Val ata gat ttt ttt tgt ggc tgt ggt gga gcc agt gaa ggg cta cgt cag      3847
Ile Asp Phe Phe Cys Gly Cys Gly Gly Ala Ser Glu Gly Leu Arg Gln
    1145                1150                1155 gct ggc ttt gat atc gag ctt gga tta gat att gac caa caa gca tca      3895
Ala Gly Phe Asp Ile Glu Leu Gly Leu Asp Ile Asp Gln Gln Ala Ser
1160                1165                1170                1175 gaa aca ttt aaa gct aat ttc cct gat gca aaa ttc atc caa gat gat      3943
Glu Thr Phe Lys Ala Asn Phe Pro Asp Ala Lys Phe Ile Gln Asp Asp
                1180                1185                1190 att agg aaa atc gaa cct caa gat atc tcc gac atc att gat att aaa      3991
Ile Arg Lys Ile Glu Pro Gln Asp Ile Ser Asp Ile Ile Asp Ile Lys
                1195                1200                1205 gct aaa cgg cct ttg tta ctg agt gca tgt gca cca tgt caa cca ttt      4039
Ala Lys Arg Pro Leu Leu Leu Ser Ala Cys Ala Pro Cys Gln Pro Phe
1210                1215                1220 tcg caa cag aat aaa aat aaa act agt gac gac tca agg aga aat cta      4087
Ser Gln Gln Asn Lys Asn Lys Thr Ser Asp Asp Ser Arg Arg Asn Leu
    1225                1230                1235 cta aat gaa act cat cgt ttt att aga gaa ctt ctt cct gaa tat att      4135
Leu Asn Glu Thr His Arg Phe Ile Arg Glu Leu Leu Pro Glu Tyr Ile
1240                1245                1250                1255 atg ctt gaa aat gtt cct gga atg caa aaa att gat gaa gaa aaa gaa      4183
Met Leu Glu Asn Val Pro Gly Met Gln Lys Ile Asp Glu Glu Lys Glu
                1260                1265                1270 ggc cca ttt cag gag ttt att aag cta ctt aaa gag tta gag tat aac      4231
Gly Pro Phe Gln Glu Phe Ile Lys Leu Leu Lys Glu Leu Glu Tyr Asn
                1275                1280                1285 tat ata tct ttt ata gcc aat gct gag aac tat ggg att ccc caa aga      4279
Tyr Ile Ser Phe Ile Ala Asn Ala Glu Asn Tyr Gly Ile Pro Gln Arg
    1290                1295                1300 aga aaa aga ctc gtg ctc tta gct agt cga gta ggt aaa gtt acc cta      4327
Arg Lys Arg Leu Val Leu Leu Ala Ser Arg Val Gly Lys Val Thr Leu
1305                1310                1315 cca gag ata acc cat ggt aaa aat aaa atc cca ttc aaa act gta cga      4375
Pro Glu Ile Thr His Gly Lys Asn Lys Ile Pro Phe Lys Thr Val Arg
```

-continued

| | |
|---|---|
| 1320 1325 1330 1335 | |
| gat tat atc cag gac ttc aca aag tta tgt tca gga gaa acc gac ccc<br>Asp Tyr Ile Gln Asp Phe Thr Lys Leu Cys Ser Gly Glu Thr Asp Pro<br>　　　　　1340　　　　　　　　1345　　　　　　　　1350 | 4423 |
| aaa gat cct tta cat agg gct gga aca ctg agc cct ctt aac cta aaa<br>Lys Asp Pro Leu His Arg Ala Gly Thr Leu Ser Pro Leu Asn Leu Lys<br>　　　1355　　　　　　　　1360　　　　　　　　1365 | 4471 |
| aga att atg cac act cca gaa gga ggg gat aga aga aat tgg cca gaa<br>Arg Ile Met His Thr Pro Glu Gly Gly Asp Arg Arg Asn Trp Pro Glu<br>1370　　　　　　　　1375　　　　　　　　1380 | 4519 |
| gag tta gtt aat aaa tgc cat aaa aat tat gat ggc cac aca gat act<br>Glu Leu Val Asn Lys Cys His Lys Asn Tyr Asp Gly His Thr Asp Thr<br>　1385　　　　　　　　1390　　　　　　　　1395 | 4567 |
| tat gga aga atg agt tgg gat aag cct gcg cct aca ctt acg acg aaa<br>Tyr Gly Arg Met Ser Trp Asp Lys Pro Ala Pro Thr Leu Thr Thr Lys<br>1400　　　　　　　　1405　　　　　　　　1410　　　　　　　　1415 | 4615 |
| tgt aat agt tac tcc aat ggt cgt ttt ggg cat cct gac ccc act caa<br>Cys Asn Ser Tyr Ser Asn Gly Arg Phe Gly His Pro Asp Pro Thr Gln<br>　　　1420　　　　　　　　1425　　　　　　　　1430 | 4663 |
| cat aga gca att agc ata aga gaa gca tca aga tta caa aca ttt cct<br>His Arg Ala Ile Ser Ile Arg Glu Ala Ser Arg Leu Gln Thr Phe Pro<br>　　　　　1435　　　　　　　　1440　　　　　　　　1445 | 4711 |
| tta agc tat gtt ttt aaa ggt tcg ctg aat tca atg gca aag caa atc<br>Leu Ser Tyr Val Phe Lys Gly Ser Leu Asn Ser Met Ala Lys Gln Ile<br>　1450　　　　　　　　1455　　　　　　　　1460 | 4759 |
| ggc aat gct gta cct tgc gaa ctc gct aga cta ttt ggg cta cat ctc<br>Gly Asn Ala Val Pro Cys Glu Leu Ala Arg Leu Phe Gly Leu His Leu<br>1465　　　　　　　　1470　　　　　　　　1475 | 4807 |
| ata gaa aat tgt act aat aag gat tca tagatatatg gctaaaataa<br>Ile Glu Asn Cys Thr Asn Lys Asp Ser<br>1480　　　　　　　　1485 | 4854 |
| gaacaaaggc tcgagctttg gac atg ctt ggc aga caa caa att gca ggt ata<br>　　　　　　　　　　　　　　Met Leu Gly Arg Gln Gln Ile Ala Gly Ile<br>　　　　　　　　　　　　　　　　　　　　　1490　　　　　　　　1495 | 4907 |
| cct act gcc ttg agt gag tta ttt aaa aat gct cat gat gcc tat gct<br>Pro Thr Ala Leu Ser Glu Leu Phe Lys Asn Ala His Asp Ala Tyr Ala<br>1500　　　　　　　　1505　　　　　　　　1510 | 4955 |
| gat aat gtc gaa gtt gat ttt ttt agg aaa gaa aat ctt ctt atc ttg<br>Asp Asn Val Glu Val Asp Phe Phe Arg Lys Glu Asn Leu Leu Ile Leu<br>1515　　　　　　　　1520　　　　　　　　1525　　　　　　　　1530 | 5003 |
| aga gat gat gga tta ggt atg aca acc gat gaa ttt gaa gag agg tgg<br>Arg Asp Asp Gly Leu Gly Met Thr Thr Asp Glu Phe Glu Glu Arg Trp<br>　　　1535　　　　　　　　1540　　　　　　　　1545 | 5051 |
| ttg act att gga acc tcc agc aaa tta atc gac gat gat gca att aat<br>Leu Thr Ile Gly Thr Ser Ser Lys Leu Ile Asp Asp Asp Ala Ile Asn<br>　　　　　1550　　　　　　　　1555　　　　　　　　1560 | 5099 |
| aaa cca gca gtg gat agt aat aaa gcc ttt cgc cct atc atg gga gag<br>Lys Pro Ala Val Asp Ser Asn Lys Ala Phe Arg Pro Ile Met Gly Glu<br>　1565　　　　　　　　1570　　　　　　　　1575 | 5147 |
| aaa gga ata ggc cgt tta tct atc gca gca att gga cca cag gtg ctg<br>Lys Gly Ile Gly Arg Leu Ser Ile Ala Ala Ile Gly Pro Gln Val Leu<br>1580　　　　　　　　1585　　　　　　　　1590 | 5195 |
| gtt ctt act agg gcc aaa aga gac aat gag ctt aag cca tta gtt gct<br>Val Leu Thr Arg Ala Lys Arg Asp Asn Glu Leu Lys Pro Leu Val Ala<br>1595　　　　　　　　1600　　　　　　　　1605　　　　　　　　1610 | 5243 |
| gca ttt gtt aat tgg agt tta ttt gct ata cca tca ctt gat ctt gat<br>Ala Phe Val Asn Trp Ser Leu Phe Ala Ile Pro Ser Leu Asp Leu Asp<br>　　　1615　　　　　　　　1620　　　　　　　　1625 | 5291 |
| gat ata gaa ata cca att aga act att atc aac gac gaa tgc ttc act | 5339 |

```
Asp Ile Glu Ile Pro Ile Arg Thr Ile Ile Asn Asp Glu Cys Phe Thr
        1630                1635                1640 aaa aaa act ctt gat gag atg att gag caa gca aga aat aat tta gac       5387
Lys Lys Thr Leu Asp Glu Met Ile Glu Gln Ala Arg Asn Asn Leu Asp
    1645                1650                1655 tct tta tca cac aaa ata tca aaa tca aaa gta tca caa ata aat aca       5435
Ser Leu Ser His Lys Ile Ser Lys Ser Lys Val Ser Gln Ile Asn Thr
1660                1665                1670 caa tta tca tct ttt gaa ttt gat cct att cta tgg gaa aaa aaa tta       5483
Gln Leu Ser Ser Phe Glu Phe Asp Pro Ile Leu Trp Glu Lys Lys Leu
1675                1680                1685                1690 ggt ggg cta aga cta tct gga gat ggg cat gga act cac ttc ata ata       5531
Gly Gly Leu Arg Leu Ser Gly Asp Gly His Gly Thr His Phe Ile Ile
        1695                1700                1705 atg cct acc gaa gaa ata tta ata gat gac att tcc acg agc gat agc       5579
Met Pro Thr Glu Glu Ile Leu Ile Asp Asp Ile Ser Thr Ser Asp Ser
        1710                1715                1720 aat aaa aca tca gag cag tct tct cgc tta gaa aaa gct tta tta ggt       5627
Asn Lys Thr Ser Glu Gln Ser Ser Arg Leu Glu Lys Ala Leu Leu Gly
    1725                1730                1735 ttt aca aac aca atg tac agt gat tca aac cct cct att ata gct cgt       5675
Phe Thr Asn Thr Met Tyr Ser Asp Ser Asn Pro Pro Ile Ile Ala Arg
1740                1745                1750 ttt aga gac tat ctg gaa gat ggt gag tgc att gac aga att agc gaa       5723
Phe Arg Asp Tyr Leu Glu Asp Gly Glu Cys Ile Asp Arg Ile Ser Glu
1755                1760                1765                1770 tca att ttt ttt aca ccg caa gaa ttc aat ctt gca gat cac cac att       5771
Ser Ile Phe Phe Thr Pro Gln Glu Phe Asn Leu Ala Asp His His Ile
        1775                1780                1785 gaa gga tgg ttc aat gaa ttt ggt caa ttc agt gga act gtt tct gtt       5819
Glu Gly Trp Phe Asn Glu Phe Gly Gln Phe Ser Gly Thr Val Ser Val
        1790                1795                1800 tat ggt gaa gag cca att cat cat gtc gtg act tgg aaa aat aat aat       5867
Tyr Gly Glu Glu Pro Ile His His Val Val Thr Trp Lys Asn Asn Asn
    1805                1810                1815 caa tta acc caa tgc ggt cca ttt aaa ata aaa tta gcg tat att cat       5915
Gln Leu Thr Gln Cys Gly Pro Phe Lys Ile Lys Leu Ala Tyr Ile His
    1820                1825                1830 ggt cgg ctt cgt gat tca cgc tta ccc atg gag ttg tgg gcc cct ctg       5963
Gly Arg Leu Arg Asp Ser Arg Leu Pro Met Glu Leu Trp Ala Pro Leu
1835                1840                1845                1850 aag gag aaa aca gat aga tat ggt ggt tta tat atc tat cga gat gga       6011
Lys Glu Lys Thr Asp Arg Tyr Gly Gly Leu Tyr Ile Tyr Arg Asp Gly
        1855                1860                1865 tta aga att ttg ccc tat gga gat tca gat acg gat ttt cta aaa ata       6059
Leu Arg Ile Leu Pro Tyr Gly Asp Ser Asp Thr Asp Phe Leu Lys Ile
        1870                1875                1880 gaa aag aga aga acg tta tcc gct tct gaa tat ttt ttc tca tat cga       6107
Glu Lys Arg Arg Thr Leu Ser Ala Ser Glu Tyr Phe Phe Ser Tyr Arg
    1885                1890                1895 cgt ttg ttt gga gca ata gaa tta aca aaa gaa aac aat gct tca tta       6155
Arg Leu Phe Gly Ala Ile Glu Leu Thr Lys Glu Asn Asn Ala Ser Leu
    1900                1905                1910 gtt gaa aaa gct ggg cga gaa gga ttc att gaa aat aag cca tat aaa       6203
Val Glu Lys Ala Gly Arg Glu Gly Phe Ile Glu Asn Lys Pro Tyr Lys
1915                1920                1925                1930 cag ttt aaa gaa atg ctt gaa aat ttc ttc atc gaa atc gca aga gat       6251
Gln Phe Lys Glu Met Leu Glu Asn Phe Phe Ile Glu Ile Ala Arg Asp
        1935                1940                1945
```

-continued

```
ttc ttt aag gac gat ggc gat atg tct gaa tta ttt gtt gag aca aag      6299
Phe Phe Lys Asp Asp Gly Asp Met Ser Glu Leu Phe Val Glu Thr Lys
        1950                1955                1960 caa cgt aga aat gaa gaa cat gat ttg tta tct aaa aga tct aaa caa      6347
Gln Arg Arg Asn Glu Glu His Asp Leu Leu Ser Lys Arg Ser Lys Gln
    1965                1970                1975 act aaa gct aaa aaa gat aga tta aag aaa gat ctg tat gat ttt ttt      6395
Thr Lys Ala Lys Lys Asp Arg Leu Lys Lys Asp Leu Tyr Asp Phe Phe
1980                1985                1990 gat aag tta gat aat gat tac tgg aat att gaa ata aat aag cta atc      6443
Asp Lys Leu Asp Asn Asp Tyr Trp Asn Ile Glu Ile Asn Lys Leu Ile
1995                2000                2005                2010 aat aaa aac gag gaa tat ttc tcc agt aca gaa ata aca gac acc aat      6491
Asn Lys Asn Glu Glu Tyr Phe Ser Ser Thr Glu Ile Thr Asp Thr Asn
            2015                2020                2025 ata gat tat gta tac aat aaa att aaa gaa caa aat gat gct atc att      6539
Ile Asp Tyr Val Tyr Asn Lys Ile Lys Glu Gln Asn Asp Ala Ile Ile
        2030                2035                2040 aaa aat cta cgt aat tct gtg gat ata aag aaa ccc tct gga gtt gga      6587
Lys Asn Leu Arg Asn Ser Val Asp Ile Lys Lys Pro Ser Gly Val Gly
    2045                2050                2055 tta aca aaa gag tta tct aat tta tgg gat aga tat caa ata gaa aga      6635
Leu Thr Lys Glu Leu Ser Asn Leu Trp Asp Arg Tyr Gln Ile Glu Arg
    2060                2065                2070 caa aaa ata ctg tta tca cta aat gag cta aaa gat aac gtt gat aga      6683
Gln Lys Ile Leu Leu Ser Leu Asn Glu Leu Lys Asp Asn Val Asp Arg
2075                2080                2085                2090 aag ctt ata gaa ctg gat aat aaa aat aat gat ttt ctc aac tta cgg      6731
Lys Leu Ile Glu Leu Asp Asn Lys Asn Asn Asp Phe Leu Asn Leu Arg
        2095                2100                2105 aag aga ctt gaa gat tct ttg aat cta caa caa agt tac tat gaa aaa      6779
Lys Arg Leu Glu Asp Ser Leu Asn Leu Gln Gln Ser Tyr Tyr Glu Lys
    2110                2115                2120 gaa cta aca aag tta tat aat gac gct aaa aat gct ttg aaa gat gtg      6827
Glu Leu Thr Lys Leu Tyr Asn Asp Ala Lys Asn Ala Leu Lys Asp Val
    2125                2130                2135 caa tct aaa gca aat agg tta att tct gat aat aag aaa aaa cat aag      6875
Gln Ser Lys Ala Asn Arg Leu Ile Ser Asp Asn Lys Lys Lys His Lys
    2140                2145                2150 agt gaa cta aaa aac att tct tat gaa ttc caa tca act aat ctc aat      6923
Ser Glu Leu Lys Asn Ile Ser Tyr Glu Phe Gln Ser Thr Asn Leu Asn
2155                2160                2165                2170 ggc aaa gat act gcg tat ata ttg gat gta aaa aga aat cta gaa agt      6971
Gly Lys Asp Thr Ala Tyr Ile Leu Asp Val Lys Arg Asn Leu Glu Ser
        2175                2180                2185 aaa att gag aat act tca aac gaa gtg att aat gaa ata aga aaa cta      7019
Lys Ile Glu Asn Thr Ser Asn Glu Val Ile Asn Glu Ile Arg Lys Leu
            2190                2195                2200 acc gac cag att gca ata att agt gat agt acc act tct gaa aat tta      7067
Thr Asp Gln Ile Ala Ile Ile Ser Asp Ser Thr Thr Ser Glu Asn Leu
        2205                2210                2215 tca tcg gct caa gta act gaa gca atc gaa act gaa ctt gaa cat tta      7115
Ser Ser Ala Gln Val Thr Glu Ala Ile Glu Thr Glu Leu Glu His Leu
    2220                2225                2230 cga gac caa caa gca aat aac gca gag tta ata cta ctt ggc atg gct      7163
Arg Asp Gln Gln Ala Asn Asn Ala Glu Leu Ile Leu Leu Gly Met Ala
2235                2240                2245                2250 ctt tct gta gta cat cat gaa ttt aat ggt aat att agg gca att aga      7211
Leu Ser Val Val His His Glu Phe Asn Gly Asn Ile Arg Ala Ile Arg
        2255                2260                2265
```

```
agt gcg cta agg gaa tta aaa gca tgg gct gac aga aat cct aag ctt         7259
Ser Ala Leu Arg Glu Leu Lys Ala Trp Ala Asp Arg Asn Pro Lys Leu
        2270                2275                2280 gat att ata tac caa aaa atc aga act agt ttt gat cac tta gat ggt         7307
Asp Ile Ile Tyr Gln Lys Ile Arg Thr Ser Phe Asp His Leu Asp Gly
        2285                2290                2295 tat tta aaa acc ttt aca cca ttg aca aga cgt tta agt cgc tct aaa         7355
Tyr Leu Lys Thr Phe Thr Pro Leu Thr Arg Arg Leu Ser Arg Ser Lys
        2300                2305                2310 acc aat ata act gga act gcc att tta gaa ttt atc aga gat gta ttc         7403
Thr Asn Ile Thr Gly Thr Ala Ile Leu Glu Phe Ile Arg Asp Val Phe
2315                2320                2325                2330 gat gat cgt ctt gag aaa gaa gga att gaa tta ttc act acc tca aag         7451
Asp Asp Arg Leu Glu Lys Glu Gly Ile Glu Leu Phe Thr Thr Ser Lys
        2335                2340                2345 ttt gtt aat caa gaa att gta act tac aca tca acc att tac cct gtc         7499
Phe Val Asn Gln Glu Ile Val Thr Tyr Thr Ser Thr Ile Tyr Pro Val
        2350                2355                2360 ttt ata aat cta att gat aac gca ata tac tgg ctt ggg aaa aca act         7547
Phe Ile Asn Leu Ile Asp Asn Ala Ile Tyr Trp Leu Gly Lys Thr Thr
        2365                2370                2375 gga gaa aaa aga ctt ata ctt gat gct act gaa aca gga ttt gtt att         7595
Gly Glu Lys Arg Leu Ile Leu Asp Ala Thr Glu Thr Gly Phe Val Ile
        2380                2385                2390 ggt gat act ggt ccc ggt gtt tca act aga gat cga gat ata ata ttt         7643
Gly Asp Thr Gly Pro Gly Val Ser Thr Arg Asp Arg Asp Ile Ile Phe
2395                2400                2405                2410 gat atg gga ttt aca cga aaa aca gga ggg cgt gga atg gga tta ttc         7691
Asp Met Gly Phe Thr Arg Lys Thr Gly Gly Arg Gly Met Gly Leu Phe
        2415                2420                2425 att tcc aaa gag tgt tta tct cga gat gga ttt act ata aga ttg gat         7739
Ile Ser Lys Glu Cys Leu Ser Arg Asp Gly Phe Thr Ile Arg Leu Asp
        2430                2435                2440 gat tac act cct gaa cag ggt gct ttc ttt att att gag cca tca gaa         7787
Asp Tyr Thr Pro Glu Gln Gly Ala Phe Phe Ile Ile Glu Pro Ser Glu
        2445                2450                2455 gaa aca agt gaa tag cggatataaa taa atg aca agc tct act gat ttt         7836
Glu Thr Ser Glu          Met Thr Ser Ser Thr Asp Phe
        2460                      2465                2470 cat aaa ctt tct gaa gac tgc gtt cgc cgt ttt tta cat tct gta gtt         7884
His Lys Leu Ser Glu Asp Cys Val Arg Arg Phe Leu His Ser Val Val
        2475                2480                2485 gct gta gat gac aat atg tct ttt gga gct ggt agt gat act ttc cct         7932
Ala Val Asp Asp Asn Met Ser Phe Gly Ala Gly Ser Asp Thr Phe Pro
        2490                2495                2500 aca gac gaa gat att aat gct tta gtt gat ccc gac gat gat cct aca         7980
Thr Asp Glu Asp Ile Asn Ala Leu Val Asp Pro Asp Asp Pro Thr
        2505                2510                2515 cca ata ata aca gca tca gca tcc cca agg ata gaa tca act aaa tca         8028
Pro Ile Ile Thr Ala Ser Ala Ser Pro Arg Ile Glu Ser Thr Lys Ser
        2520                2525                2530 aaa gca aag gta aaa aac cat cct ttt gat tac caa gct cta gca gaa         8076
Lys Ala Lys Val Lys Asn His Pro Phe Asp Tyr Gln Ala Leu Ala Glu
2535                2540                2545                2550 gct ttc gcc aaa gat ggt att gct tgt tgc gga tta tta gct aag agt         8124
Ala Phe Ala Lys Asp Gly Ile Ala Cys Cys Gly Leu Leu Ala Lys Ser
        2555                2560                2565 ttt aat gtt gaa gaa aga gat ata att aca gca tca tcc cac aag gca         8172
Phe Asn Val Glu Glu Arg Asp Ile Ile Thr Ala Ser Ser His Lys Ala
```

```
                 2570            2575            2580
gat ata aca ata ctt gac tgg gat atg caa agc gat agt ggg caa ttt     8220
Asp Ile Thr Ile Leu Asp Trp Asp Met Gln Ser Asp Ser Gly Gln Phe
        2585            2590            2595 gct att gaa ata ata aaa tcg ata atc gtt tca gat ata aat tct gga     8268
Ala Ile Glu Ile Ile Lys Ser Ile Ile Val Ser Asp Ile Asn Ser Gly
    2600            2605            2610 gga cgt tta cgt ctt ctt tct att tat act ggt gaa cat gtt act gct     8316
Gly Arg Leu Arg Leu Leu Ser Ile Tyr Thr Gly Glu His Val Thr Ala
2615            2620            2625            2630 gtt ata act aag ttg aac aat gag tta aag aaa aca tac cgt agc gta     8364
Val Ile Thr Lys Leu Asn Asn Glu Leu Lys Lys Thr Tyr Arg Ser Val
        2635            2640            2645 ata aaa aat gat gat agt att ttt att gaa gat aac tat gca ctc gaa     8412
Ile Lys Asn Asp Asp Ser Ile Phe Ile Glu Asp Asn Tyr Ala Leu Glu
    2650            2655            2660 caa tgg tgt ata gtt gtt att agt aaa gac gtt tat gaa aaa gat ctt     8460
Gln Trp Cys Ile Val Val Ile Ser Lys Asp Val Tyr Glu Lys Asp Leu
2665            2670            2675 cca aat gtg tta ata aaa aaa ttc act aac ctt aca gct ggg ttg cta     8508
Pro Asn Val Leu Ile Lys Lys Phe Thr Asn Leu Thr Ala Gly Leu Leu
    2680            2685            2690 tcc aac gcc gca ctc tct tgc att tct gaa ata aga gaa aaa acc cat     8556
Ser Asn Ala Ala Leu Ser Cys Ile Ser Glu Ile Arg Glu Lys Thr His
2695            2700            2705            2710 ggg ata tta aca aaa tat aat aat aaa tta gac act gca tat gtt tcc     8604
Gly Ile Leu Thr Lys Tyr Asn Asn Lys Leu Asp Thr Ala Tyr Val Ser
        2715            2720            2725 cac atc tta aat tta ata aaa tcc aag gag tca agg gca tat gct tat     8652
His Ile Leu Asn Leu Ile Lys Ser Lys Glu Ser Arg Ala Tyr Ala Tyr
    2730            2735            2740 gaa aat gct cat gat tat gca gta gat tta att tct gaa gaa ata aga     8700
Glu Asn Ala His Asp Tyr Ala Val Asp Leu Ile Ser Glu Glu Ile Arg
2745            2750            2755 tca ata ttg caa ata agt gaa aac tta aag aaa tct cta agc aaa aac     8748
Ser Ile Leu Gln Ile Ser Glu Asn Leu Lys Lys Ser Leu Ser Lys Asn
    2760            2765            2770 tcc tta tcc cat tgg cct att ttt cac tat gca aaa aat ggt tgt aag     8796
Ser Leu Ser His Trp Pro Ile Phe His Tyr Ala Lys Asn Gly Cys Lys
2775            2780            2785            2790 aat ttt cta tta act gga aaa aaa caa aaa gac tta tca gta gaa cat     8844
Asn Phe Leu Leu Thr Gly Lys Lys Gln Lys Asp Leu Ser Val Glu His
        2795            2800            2805 cta agg aat ata ctc tct gct gat tct tta gaa gaa att caa cac gct     8892
Leu Arg Asn Ile Leu Ser Ala Asp Ser Leu Glu Glu Ile Gln His Ala
    2810            2815            2820 att gaa cac gca tct tta ggt aaa aag gaa tac tta agc caa gat ggt     8940
Ile Glu His Ala Ser Leu Gly Lys Lys Glu Tyr Leu Ser Gln Asp Gly
2825            2830            2835 gaa gaa gat aaa aag tta atg caa tta tgc tct ctg gaa atc acg cgc     8988
Glu Glu Asp Lys Lys Leu Met Gln Leu Cys Ser Leu Glu Ile Thr Arg
        2840            2845            2850 agg agt tta aga tat cat tct cat ata gat aat gtg tcc tta aaa caa     9036
Arg Ser Leu Arg Tyr His Ser His Ile Asp Asn Val Ser Leu Lys Gln
2855            2860            2865            2870 gga act tta ctt tta gat gca tat aat ttt gtc tat cta tgc ata caa     9084
Gly Thr Leu Leu Leu Asp Ala Tyr Asn Phe Val Tyr Leu Cys Ile Gln
        2875            2880            2885 cca tta tgt gat agc gtc aga ttg cat gaa aaa gcc gat ttt tta ttc     9132
```

```
                                                    -continued

Pro Leu Cys Asp Ser Val Arg Leu His Glu Lys Ala Asp Phe Leu Phe
        2890                2895                2900 ctc agg gga aca ctg gac gat aat aat tac aat ttg tta atc gaa gat      9180
Leu Arg Gly Thr Leu Asp Asp Asn Asn Tyr Asn Leu Leu Ile Glu Asp
        2905                2910                2915 gaa tat ggc ggt ttt tat aaa att aaa atg ccg gca aaa gct tct aat      9228
Glu Tyr Gly Gly Phe Tyr Lys Ile Lys Met Pro Ala Lys Ala Ser Asn
        2920                2925                2930 att att tca ttt tca ttt gga gtc gaa aat gga aac ggt gtc atc ata      9276
Ile Ile Ser Phe Ser Phe Gly Val Glu Asn Gly Asn Gly Val Ile Ile
2935                2940                2945                2950 ggg aaa aag aac aat cta gtt aat act gac tat atc tca ttc gtt cct      9324
Gly Lys Lys Asn Asn Leu Val Asn Thr Asp Tyr Ile Ser Phe Val Pro
        2955                2960                2965 tta ctc gtt gaa aaa ata tct act cca aaa gta ttg aaa tgg atc ggg      9372
Leu Leu Val Glu Lys Ile Ser Thr Pro Lys Val Leu Lys Trp Ile Gly
        2970                2975                2980 gaa ata aaa aca acg tac gcg caa aaa ata aca act gat att gtt gct      9420
Glu Ile Lys Thr Thr Tyr Ala Gln Lys Ile Thr Thr Asp Ile Val Ala
        2985                2990                2995 aat ctg tca aga ata ggt tta gat caa cat gag tgg tta cga ata aaa      9468
Asn Leu Ser Arg Ile Gly Leu Asp Gln His Glu Trp Leu Arg Ile Lys
        3000                3005                3010 tca aaa gat ata taaatgatta tatatgccgt cgttttataa aaactggcgg          9520
Ser Lys Asp Ile
3015 catgtatatc tagttagtcc atcatagaag tcaagaaatt tagtttgccc tatatcttat    9580 agaaaatata ttttatatgc ttaaaaaaca ccatctttct aagatggcat ttatgtgctt    9640 tgtttcgatc aattacaact gatatattac catattgatt aattttatgt tatttaccaa    9700 agtaacggca tcttaatata tcgtcataat atagtgcgcg ttctgactct aatactgaaa    9760 aatttatttg ttctatttta cacttactgc aaatagcatc cagtttatca tatagtgtcg    9820 catcaattgg cgcag atg tca tca cgc caa atc ctt gag cat tat aat gct     9871
              Met Ser Ser Arg Gln Ile Leu Glu His Tyr Asn Ala
                          3020                3025                3030 cta aca tat ccc cta cat caa tca atc ttg ttg cag ata atg act tcg      9919
Leu Thr Tyr Pro Leu His Gln Ser Ile Leu Leu Gln Ile Met Thr Ser
        3035                3040                3045 aat ttg tta tca gtt tgc act gga aaa tcc att tac gag gat atc tcc      9967
Asn Leu Leu Ser Val Cys Thr Gly Lys Ser Ile Tyr Glu Asp Ile Ser
        3050                3055                3060 ggc agt tct tgg aat atc ata cac ttc aat atc cct ctc ccc atc tct     10015
Gly Ser Ser Trp Asn Ile Ile His Phe Asn Ile Pro Leu Pro Ile Ser
        3065                3070                3075 aga gcg aga ctt tcc ata ttt tct tat tgt gtc aga att aaa cct tgg     10063
Arg Ala Arg Leu Ser Ile Phe Ser Tyr Cys Val Arg Ile Lys Pro Trp
        3080                3085                3090 atg agt atg gat tac atg taaccggctc atttaaaccg tctggtctgt            10111
Met Ser Met Asp Tyr Met
3095            3100 ttcctccggt tttacaaaaa ta atg tcc atc att ttt aat gga cac tat cgt    10163
                       Met Ser Ile Ile Phe Asn Gly His Tyr Arg
                                  3105                3110 atg aaa cac cgg act tgg atc act gaa gct tta cgt ctt cac ttt gaa     10211
Met Lys His Arg Thr Trp Ile Thr Glu Ala Leu Arg Leu His Phe Glu
        3115                3120                3125 gaa cat tta ccc cag gtt gtg gtc ggg cgt cgc ctg ggc gta cca aaa     10259
Glu His Leu Pro Gln Val Val Val Gly Arg Arg Leu Gly Val Pro Lys
```

```
                3130              3135              3140
tca aca gct tgt ggt atg ttc gtg cgc ttt cgc aaa gct ggc ttt tca    10307
Ser Thr Ala Cys Gly Met Phe Val Arg Phe Arg Lys Ala Gly Phe Ser
        3145              3150              3155 tgg cct ctg ccc gca ggt atg tcg gag cgg gag ctt gat ggc cgt ctt    10355
Trp Pro Leu Pro Ala Gly Met Ser Glu Arg Glu Leu Asp Gly Arg Leu
    3160              3165              3170 tac ggg agt acc tcc aca gta cct gtc gta ctt tgt agt gga tcg gta    10403
Tyr Gly Ser Thr Ser Thr Val Pro Val Val Leu Cys Ser Gly Ser Val
3175              3180              3185              3190 att cag gac acc tcg aaa tcc tgt taatgttaaa acagtgaaaa tgaggtgatg    10457
Ile Gln Asp Thr Ser Lys Ser Cys
            3195 c atg atc aaa act cgt cgg act aaa cgt acc ttt tcc ccg gag ttc aag    10506
  Met Ile Lys Thr Arg Arg Thr Lys Arg Thr Phe Ser Pro Glu Phe Lys
          3200              3205              3210 ctt gaa gct ttc gag cag gtg gtg gtt aaa tac cag cgt gat gtc aga    10554
Leu Glu Ala Phe Glu Gln Val Val Val Lys Tyr Gln Arg Asp Val Arg
3215              3220              3225              3230 gaa gtc gcg cag gca ctc gag ctc aac cct gac cat ttg cgt aaa tgg    10602
Glu Val Ala Gln Ala Leu Glu Leu Asn Pro Asp His Leu Arg Lys Trp
            3235              3240              3245 ata cgg ttg tat aag cag gaa ctt cag ggt att gag cca gct ggt aat    10650
Ile Arg Leu Tyr Lys Gln Glu Leu Gln Gly Ile Glu Pro Ala Gly Asn
        3250              3255              3260 gct att acc cct gaa caa cgc gaa att cag cag ctt aaa gcg cag ata    10698
Ala Ile Thr Pro Glu Gln Arg Glu Ile Gln Gln Leu Lys Ala Gln Ile
    3265              3270              3275 aag cgc gtt gag atg gaa aaa gaa ata cta aag cag gct gcc gtg ctg    10746
Lys Arg Val Glu Met Glu Lys Glu Ile Leu Lys Gln Ala Ala Val Leu
3280              3285              3290 atg agc gaa atc ccc ggg aag ctg tcg cgc taatcacaca gctgaaagca    10796
Met Ser Glu Ile Pro Gly Lys Leu Ser Arg
3295              3300 aagtggccag tgtgggttat ttgtcattta ttcggtatta accgtagcgt ttattacgcg    10856
caggtgaagc gtcctgttaa tgtgcaaaga attgaattac gaagccgggt gagggctttc    10916
catgctctca gtcgtggcgc agccgggtag ccgggcaatc agtcagatgt tgcgccagag    10976
tggcgttgat gcaggccggt ggctggcatg acgactgatg cgggaatgag ggctgacaag    11036
tcgacagccg gttaaacatc acaaccgggt aaacgaagac aaaagtccgc cattgccaaa    11096
tttactgaac cggcaatttc accccgccgc accaaactgc gtctggtgcg gcgacatcag    11156
ttttattcg                                                            11165

<210> SEQ ID NO 35
<211> LENGTH: 366
<212> TYPE: PRT
<213> ORGANISM: Escherichia coli

<400> SEQUENCE: 35

Ser Asp Met Gln Arg Gly Ile Gln Ala Ala Thr Ala Ala Leu Gln Gly
1               5                   10                  15

Leu Val Gly Gly Asn Met Ala Gly Ala Leu Ala Gly Ala Ser Ala Pro
            20                  25                  30

Glu Leu Ala Asn Ile Ile Gly His His Ala Gly Ile Asp Asp Asn Thr
        35                  40                  45

Ala Ala Lys Ala Ile Ala His Ala Ile Leu Gly Gly Val Thr Ala Ala
    50                  55                  60
```

-continued

Leu Gln Gly Asn Ser Ala Ala Gly Ala Ile Gly Ala Gly Thr Gly
65                  70                  75                  80

Glu Val Ile Ala Ser Ala Ile Ala Lys Ser Leu Tyr Pro Gly Val Asp
                85                  90                  95

Pro Ser Lys Leu Thr Glu Asp Gln Lys Gln Thr Val Ser Thr Leu Ala
            100                 105                 110

Thr Leu Ser Ala Gly Met Ala Gly Ile Ala Ser Gly Asp Val Ala
        115                 120                 125

Gly Ala Ala Ala Gly Ala Gly Ala Lys Asn Val Val Glu Asn Asn
130                 135                 140

Ala Leu Ser Leu Val Ala Arg Gly Cys Ala Val Ala Ala Pro Cys Arg
145                 150                 155                 160

Thr Lys Val Ala Glu Gln Leu Leu Glu Ile Gly Ala Lys Ala Gly Met
                165                 170                 175

Ala Gly Leu Ala Gly Ala Ala Val Lys Asp Met Ala Asp Arg Met Thr
            180                 185                 190

Ser Asp Glu Leu Glu His Leu Ile Thr Leu Gln Met Met Gly Asn Asp
        195                 200                 205

Glu Ile Thr Thr Lys Tyr Leu Ser Ser Leu His Asp Lys Tyr Gly Ser
210                 215                 220

Gly Ala Ala Ser Asn Pro Asn Ile Gly Lys Asp Leu Thr Asp Ala Glu
225                 230                 235                 240

Lys Val Glu Leu Gly Gly Ser Gly Ser Gly Thr Gly Thr Pro Pro Pro
                245                 250                 255

Ser Glu Asn Asp Pro Lys Gln Gln Asn Glu Lys Thr Val Asp Lys Leu
            260                 265                 270

Asn Gln Lys Gln Glu Ser Ala Ile Lys Lys Ile Asp Asn Thr Ile Lys
        275                 280                 285

Asn Ala Leu Lys Asp His Asp Ile Ile Gly Thr Leu Lys Asp Met Asp
290                 295                 300

Gly Lys Pro Val Pro Lys Glu Asn Gly Gly Tyr Trp Asp His Met Gln
305                 310                 315                 320

Glu Met Gln Asn Thr Leu Arg Gly Leu Arg Asn His Ala Asp Thr Leu
                325                 330                 335

Lys Asn Val Asn Asn Pro Glu Ala Gln Ala Ala Tyr Gly Arg Ala Thr
            340                 345                 350

Asp Ala Ile Asn Lys Ile Glu Ser Ala Leu Lys Gly Tyr Gly
        355                 360                 365

<210> SEQ ID NO 36
<211> LENGTH: 128
<212> TYPE: PRT
<213> ORGANISM: Escherichia coli

<400> SEQUENCE: 36

Met Ile Thr Leu Arg Lys Leu Ile Gly Asn Ile Asn Met Thr Lys Glu
1               5                   10                  15

Pro Glu Gln Gln Ser Pro Leu Glu Leu Trp Phe Glu Arg Ile Ile Asp
                20                  25                  30

Val Pro Leu Glu Lys Leu Thr Val Glu Asp Leu Cys Arg Ala Ile Arg
            35                  40                  45

Gln Asn Leu Cys Ile Asp Gln Leu Met Pro Arg Val Leu Glu Val Leu
        50                  55                  60

Thr Lys Glu Pro Leu Ala Gly Glu Tyr Tyr Asp Gly Glu Leu Ile Ala

-continued

```
                65                  70                  75                  80
Ala Leu Ser Thr Ile Lys Gly Glu Asp Leu Lys Asp Gln Lys Ser Thr
                    85                  90                  95

Phe Thr Gln Ile Arg Gln Leu Ile Asn Gln Leu Glu Pro Ser Asp Ile
                100                 105                 110

Asn Asp Asp Leu Arg Lys Asp Ile Leu Lys Ile Asn Gln Ile Ile Val
            115                 120                 125

<210> SEQ ID NO 37
<211> LENGTH: 107
<212> TYPE: PRT
<213> ORGANISM: Escherichia coli

<400> SEQUENCE: 37

Met Val Ala Lys Ala Phe Ala Tyr Ala Leu Asn Gln Trp Pro Ala Leu
  1               5                  10                  15

Thr Tyr Tyr Ala Asn Asp Gly Trp Val Glu Ile Asp Asn Asn Ile Ala
                 20                  25                  30

Glu Asn Ala Leu Arg Ala Val Ser Leu Gly Arg Lys Asn Phe Leu Phe
             35                  40                  45

Phe Gly Ser Asp His Gly Gly Glu Arg Gly Ala Leu Leu Tyr Ser Leu
         50                  55                  60

Ile Gly Thr Cys Lys Leu Asn Asp Val Asp Pro Glu Ser Tyr Leu Arg
 65                  70                  75                  80

His Val Leu Ala Val Ile Ala Asp Trp Pro Val Asn Arg Val Ser Glu
                 85                  90                  95

Leu Leu Pro Trp Arg Ile Ala Leu Pro Ala Glu
            100                 105

<210> SEQ ID NO 38
<211> LENGTH: 86
<212> TYPE: PRT
<213> ORGANISM: Escherichia coli

<400> SEQUENCE: 38

Met Leu Met Ser Val Gln Lys Glu Lys Asn Val Ala Glu Ser Val Val
  1               5                  10                  15

Ser Glu Thr His Thr Gly Asp Ser Val Tyr Ala Ser Leu Phe Glu Lys
                 20                  25                  30

Ile Asn Leu Asn Pro Val Ser Ala Leu Ser Ala Leu Asp Asn Pro Phe
             35                  40                  45

Arg Ser Ala Asp Asn Ala Thr Gly Arg Ile Thr Ser Ser Ile Gln Pro
         50                  55                  60

Ala Val Gln Cys Ala Ala Ala Ala Thr Glu Gly Ser Cys Pro Arg
 65                  70                  75                  80

Gln Ser Pro Cys Ser Gly
                 85

<210> SEQ ID NO 39
<211> LENGTH: 111
<212> TYPE: PRT
<213> ORGANISM: Escherichia coli

<400> SEQUENCE: 39

Met Val Asp Asn Trp Gln Lys Ser Val Arg Ser Arg Ala Leu Pro Glu
  1               5                  10                  15

Glu Ala Met Thr Gly Trp Asn Glu Gly Met Ile Arg Leu Gln Gln Leu
                 20                  25                  30
```

```
Ala Glu Arg Leu Asn Arg Gln Asp Glu Gln Arg Gly Lys Tyr Met Thr
         35                  40                  45

Val Ser Glu Leu Lys Thr Glu Val Phe Gly Ile Met Gln Ala Phe Asn
 50                  55                  60

Arg His Ile Pro Ala Glu Gln Leu Arg Arg Tyr Gly Glu Val Arg
 65                  70                  75                  80

Asn Gln Asn Gly Ser Glu Gln Gln Lys Gln Ala Glu Met Ala Leu
                 85                  90                  95

Asn Gln Leu Ile Asn Arg Tyr Gln Met Ile Arg Ala Gly Lys Gln
            100                 105                 110
```

<210> SEQ ID NO 40
<211> LENGTH: 143
<212> TYPE: PRT
<213> ORGANISM: Escherichia coli

<400> SEQUENCE: 40

```
Met Val Gly Cys Ala Trp Leu Ala Glu Gln Ala Phe Ser Asp His Ala
 1               5                  10                  15

Leu Ser Pro His Ser Ala Trp Pro Tyr Ser Ala Ser Arg Asp Ala Gly
            20                  25                  30

Leu Ala Asp Thr Gly Ala Gly Gly Tyr Pro Thr Cys Lys Gln Arg Trp
         35                  40                  45

Ala Asp Asp Thr Val Gly Leu Lys Ala Arg Leu Leu Gln Leu Pro Ala
 50                  55                  60

Leu Asp Ile Trp Thr Ala Phe Lys Lys Ile Asp Gln Ser Gln Val Val
 65                  70                  75                  80

Tyr Glu Glu Ala Val Leu Arg Ser Arg Val Ser Glu Arg Asn Met Gln
                 85                  90                  95

Val Ser Gln Asn Gly Arg Val Tyr Pro Ser Tyr Gly Gly Asn Val Asp
            100                 105                 110

Gly Thr Val Ala Asn Ala Ala Thr Arg Leu Ala Ser Gly Ala Arg Asn
         115                 120                 125

Ile Leu Gly Ser Ile Ala Ala Cys Thr Ala Phe Asp Ser Val Arg
 130                 135                 140
```

<210> SEQ ID NO 41
<211> LENGTH: 118
<212> TYPE: PRT
<213> ORGANISM: Escherichia coli

<400> SEQUENCE: 41

```
Met Val Gln Ala Gln Leu Gln Ile Ala Leu Val Ile Cys Ile Pro Leu
 1               5                  10                  15

Ile Thr Leu Cys Ser Ala Trp Asp Val Lys Val Val Met Thr Leu Thr
            20                  25                  30

Phe Val Gln Phe Ala Leu Phe Phe Leu Thr Phe Trp Glu Leu Ala
         35                  40                  45

Arg Trp Leu Asp Ser Trp Leu Leu Asp Val Leu Tyr Asn Ser Asp Thr
 50                  55                  60

His Ser Ser Trp Asn Leu Ala Gly Ile Gln Asn Thr Gln Asp Asp Val
 65                  70                  75                  80

Ile Ile Asn Leu Val Met Arg Leu Met Phe Leu Val Leu Pro Thr Phe
                 85                  90                  95

Trp Leu Gly Ala Met Thr Trp Ala Gly Val Arg Val Gly Val Ala Leu
            100                 105                 110
```

```
Asn Gly Ala Leu Ala Gly
        115

<210> SEQ ID NO 42
<211> LENGTH: 81
<212> TYPE: PRT
<213> ORGANISM: Escherichia coli

<400> SEQUENCE: 42

Met Lys Tyr Leu Phe Phe Glu Asn Ile His Ser Ile Phe Leu Thr Phe
  1               5                  10                  15

Ser Leu Phe Arg Thr Ser Val Ser Pro Asp Phe Pro Met Ile Phe Ala
             20                  25                  30

Leu Pro Ser Ile Ile Leu Gly Gln Phe Thr Thr Asn Gln Leu Thr Asn
         35                  40                  45

Phe Val Ile Cys Met Gly Asn Thr Val Glu Arg Arg Leu Gly Val Val
     50                  55                  60

His Asn Pro Phe Lys Arg Ser Gly Asp Gly His Asp Leu Arg Ala Val
 65                  70                  75                  80

Ala

<210> SEQ ID NO 43
<211> LENGTH: 348
<212> TYPE: PRT
<213> ORGANISM: Escherichia coli

<400> SEQUENCE: 43

Leu Ile Val Ile Asp Phe Phe Cys Gly Cys Gly Gly Ala Ser Glu Gly
  1               5                  10                  15

Leu Arg Gln Ala Gly Phe Asp Ile Glu Leu Gly Leu Asp Ile Asp Gln
             20                  25                  30

Gln Ala Ser Glu Thr Phe Lys Ala Asn Phe Pro Asp Ala Lys Phe Ile
         35                  40                  45

Gln Asp Asp Ile Arg Lys Ile Glu Pro Gln Asp Ile Ser Asp Ile Ile
     50                  55                  60

Asp Ile Lys Ala Lys Arg Pro Leu Leu Leu Ser Ala Cys Ala Pro Cys
 65                  70                  75                  80

Gln Pro Phe Ser Gln Asn Lys Asn Lys Thr Ser Asp Asp Ser Arg
                 85                  90                  95

Arg Asn Leu Leu Asn Glu Thr His Arg Phe Ile Arg Glu Leu Leu Pro
            100                 105                 110

Glu Tyr Ile Met Leu Glu Asn Val Pro Gly Met Gln Lys Ile Asp Glu
            115                 120                 125

Glu Lys Glu Gly Pro Phe Gln Glu Phe Ile Lys Leu Leu Lys Glu Leu
        130                 135                 140

Glu Tyr Asn Tyr Ile Ser Phe Ile Ala Asn Ala Glu Asn Tyr Gly Ile
145                 150                 155                 160

Pro Gln Arg Arg Lys Arg Leu Val Leu Leu Ala Ser Arg Val Gly Lys
                165                 170                 175

Val Thr Leu Pro Glu Ile Thr His Gly Lys Asn Lys Ile Pro Phe Lys
            180                 185                 190

Thr Val Arg Asp Tyr Ile Gln Asp Phe Thr Lys Leu Cys Ser Gly Glu
            195                 200                 205

Thr Asp Pro Lys Asp Pro Leu His Arg Ala Gly Thr Leu Ser Pro Leu
        210                 215                 220
```

```
Asn Leu Lys Arg Ile Met His Thr Pro Glu Gly Gly Asp Arg Arg Asn
225                 230                 235                 240

Trp Pro Glu Glu Leu Val Asn Lys Cys His Lys Asn Tyr Asp Gly His
            245                 250                 255

Thr Asp Thr Tyr Gly Arg Met Ser Trp Asp Lys Pro Ala Pro Thr Leu
        260                 265                 270

Thr Thr Lys Cys Asn Ser Tyr Ser Asn Gly Arg Phe Gly His Pro Asp
    275                 280                 285

Pro Thr Gln His Arg Ala Ile Ser Ile Arg Glu Ala Ser Arg Leu Gln
    290                 295                 300

Thr Phe Pro Leu Ser Tyr Val Phe Lys Gly Ser Leu Asn Ser Met Ala
305                 310                 315                 320

Lys Gln Ile Gly Asn Ala Val Pro Cys Glu Leu Ala Arg Leu Phe Gly
                325                 330                 335

Leu His Leu Ile Glu Asn Cys Thr Asn Lys Asp Ser
            340                 345

<210> SEQ ID NO 44
<211> LENGTH: 974
<212> TYPE: PRT
<213> ORGANISM: Escherichia coli

<400> SEQUENCE: 44

Met Leu Gly Arg Gln Gln Ile Ala Gly Ile Pro Thr Ala Leu Ser Glu
 1               5                  10                  15

Leu Phe Lys Asn Ala His Asp Ala Tyr Ala Asp Asn Val Glu Val Asp
            20                  25                  30

Phe Phe Arg Lys Glu Asn Leu Leu Ile Leu Arg Asp Asp Gly Leu Gly
        35                  40                  45

Met Thr Thr Asp Glu Phe Glu Glu Arg Trp Leu Thr Ile Gly Thr Ser
    50                  55                  60

Ser Lys Leu Ile Asp Asp Ala Ile Asn Lys Pro Ala Val Asp Ser
65                  70                  75                  80

Asn Lys Ala Phe Arg Pro Ile Met Gly Glu Lys Gly Ile Gly Arg Leu
                85                  90                  95

Ser Ile Ala Ala Ile Gly Pro Gln Val Leu Val Leu Thr Arg Ala Lys
            100                 105                 110

Arg Asp Asn Glu Leu Lys Pro Leu Val Ala Ala Phe Val Asn Trp Ser
        115                 120                 125

Leu Phe Ala Ile Pro Ser Leu Asp Leu Asp Asp Ile Glu Ile Pro Ile
    130                 135                 140

Arg Thr Ile Ile Asn Asp Glu Cys Phe Thr Lys Lys Thr Leu Asp Glu
145                 150                 155                 160

Met Ile Glu Gln Ala Arg Asn Asn Leu Asp Ser Leu Ser His Lys Ile
                165                 170                 175

Ser Lys Ser Lys Val Ser Gln Ile Asn Thr Gln Leu Ser Ser Phe Glu
            180                 185                 190

Phe Asp Pro Ile Leu Trp Glu Lys Lys Leu Gly Gly Leu Arg Leu Ser
        195                 200                 205

Gly Asp Gly His Gly Thr His Phe Ile Ile Met Pro Thr Glu Glu Ile
    210                 215                 220

Leu Ile Asp Asp Ile Ser Thr Ser Asp Ser Asn Lys Thr Ser Glu Gln
225                 230                 235                 240

Ser Ser Arg Leu Glu Lys Ala Leu Leu Gly Phe Thr Asn Thr Met Tyr
                245                 250                 255
```

-continued

```
Ser Asp Ser Asn Pro Ile Ile Ala Arg Phe Arg Asp Tyr Leu Glu
        260                 265                 270
Asp Gly Glu Cys Ile Asp Arg Ile Ser Glu Ser Ile Phe Phe Thr Pro
        275                 280                 285
Gln Glu Phe Asn Leu Ala Asp His His Ile Glu Gly Trp Phe Asn Glu
        290                 295                 300
Phe Gly Gln Phe Ser Gly Thr Val Ser Val Tyr Gly Glu Pro Ile
305                 310                 315                 320
His His Val Val Thr Trp Lys Asn Asn Gln Leu Thr Gln Cys Gly
                    325                 330                 335
Pro Phe Lys Ile Lys Leu Ala Tyr Ile His Gly Arg Leu Arg Asp Ser
        340                 345                 350
Arg Leu Pro Met Glu Leu Trp Ala Pro Leu Lys Glu Lys Thr Asp Arg
        355                 360                 365
Tyr Gly Gly Leu Tyr Ile Tyr Arg Asp Gly Leu Arg Ile Leu Pro Tyr
        370                 375                 380
Gly Asp Ser Asp Thr Asp Phe Leu Lys Ile Glu Lys Arg Arg Thr Leu
385                 390                 395                 400
Ser Ala Ser Glu Tyr Phe Phe Ser Tyr Arg Arg Leu Phe Gly Ala Ile
                405                 410                 415
Glu Leu Thr Lys Glu Asn Asn Ala Ser Leu Val Glu Lys Ala Gly Arg
            420                 425                 430
Glu Gly Phe Ile Glu Asn Lys Pro Tyr Lys Gln Phe Lys Glu Met Leu
            435                 440                 445
Glu Asn Phe Phe Ile Glu Ile Ala Arg Asp Phe Phe Lys Asp Asp Gly
        450                 455                 460
Asp Met Ser Glu Leu Phe Val Glu Thr Lys Gln Arg Arg Asn Glu Glu
465                 470                 475                 480
His Asp Leu Leu Ser Lys Arg Ser Lys Gln Thr Lys Ala Lys Lys Asp
                485                 490                 495
Arg Leu Lys Lys Asp Leu Tyr Asp Phe Phe Asp Lys Leu Asp Asn Asp
            500                 505                 510
Tyr Trp Asn Ile Glu Ile Asn Lys Leu Ile Asn Lys Asn Glu Glu Tyr
        515                 520                 525
Phe Ser Ser Thr Glu Ile Thr Asp Thr Asn Ile Asp Tyr Val Tyr Asn
530                 535                 540
Lys Ile Lys Glu Gln Asn Asp Ala Ile Ile Lys Asn Leu Arg Asn Ser
545                 550                 555                 560
Val Asp Ile Lys Lys Pro Ser Gly Val Gly Leu Thr Lys Glu Leu Ser
                565                 570                 575
Asn Leu Trp Asp Arg Tyr Gln Ile Glu Arg Gln Lys Ile Leu Leu Ser
            580                 585                 590
Leu Asn Glu Leu Lys Asp Asn Val Asp Arg Lys Leu Ile Glu Leu Asp
        595                 600                 605
Asn Lys Asn Asn Asp Phe Leu Asn Leu Arg Lys Arg Leu Glu Asp Ser
        610                 615                 620
Leu Asn Leu Gln Gln Ser Tyr Tyr Glu Lys Glu Leu Thr Lys Leu Tyr
625                 630                 635                 640
Asn Asp Ala Lys Asn Ala Leu Lys Asp Val Gln Ser Lys Ala Asn Arg
                645                 650                 655
Leu Ile Ser Asp Asn Lys Lys His Lys Ser Glu Leu Lys Asn Ile
            660                 665                 670
```

```
Ser Tyr Glu Phe Gln Ser Thr Asn Leu Asn Gly Lys Asp Thr Ala Tyr
        675                 680                 685

Ile Leu Asp Val Lys Arg Asn Leu Glu Ser Lys Ile Glu Asn Thr Ser
690                 695                 700

Asn Glu Val Ile Asn Glu Ile Arg Lys Leu Thr Asp Gln Ile Ala Ile
705                 710                 715                 720

Ile Ser Asp Ser Thr Thr Ser Glu Asn Leu Ser Ser Ala Gln Val Thr
                725                 730                 735

Glu Ala Ile Glu Thr Glu Leu Glu His Leu Arg Asp Gln Gln Ala Asn
            740                 745                 750

Asn Ala Glu Leu Ile Leu Leu Gly Met Ala Leu Ser Val Val His His
        755                 760                 765

Glu Phe Asn Gly Asn Ile Arg Ala Ile Arg Ser Ala Leu Arg Glu Leu
    770                 775                 780

Lys Ala Trp Ala Asp Arg Asn Pro Lys Leu Asp Ile Ile Tyr Gln Lys
785                 790                 795                 800

Ile Arg Thr Ser Phe Asp His Leu Asp Gly Tyr Leu Lys Thr Phe Thr
                805                 810                 815

Pro Leu Thr Arg Arg Leu Ser Arg Ser Lys Thr Asn Ile Thr Gly Thr
            820                 825                 830

Ala Ile Leu Glu Phe Ile Arg Asp Val Phe Asp Arg Leu Glu Lys
        835                 840                 845

Glu Gly Ile Glu Leu Phe Thr Thr Ser Lys Phe Val Asn Gln Glu Ile
    850                 855                 860

Val Thr Tyr Thr Ser Thr Ile Tyr Pro Val Phe Ile Asn Leu Ile Asp
865                 870                 875                 880

Asn Ala Ile Tyr Trp Leu Gly Lys Thr Thr Gly Glu Lys Arg Leu Ile
                885                 890                 895

Leu Asp Ala Thr Glu Thr Gly Phe Val Ile Gly Asp Thr Gly Pro Gly
            900                 905                 910

Val Ser Thr Arg Asp Arg Asp Ile Ile Phe Asp Met Gly Phe Thr Arg
        915                 920                 925

Lys Thr Gly Gly Arg Gly Met Gly Leu Phe Ile Ser Lys Glu Cys Leu
    930                 935                 940

Ser Arg Asp Gly Phe Thr Ile Arg Leu Asp Asp Tyr Thr Pro Glu Gln
945                 950                 955                 960

Gly Ala Phe Phe Ile Ile Glu Pro Ser Glu Glu Thr Ser Glu
                965                 970

<210> SEQ ID NO 45
<211> LENGTH: 555
<212> TYPE: PRT
<213> ORGANISM: Escherichia coli

<400> SEQUENCE: 45

Met Thr Ser Ser Thr Asp Phe His Lys Leu Ser Glu Asp Cys Val Arg
1               5                   10                  15

Arg Phe Leu His Ser Val Val Ala Val Asp Asp Asn Met Ser Phe Gly
            20                  25                  30

Ala Gly Ser Asp Thr Phe Pro Thr Asp Glu Asp Ile Asn Ala Leu Val
        35                  40                  45

Asp Pro Asp Asp Asp Pro Thr Pro Ile Ile Thr Ala Ser Ala Ser Pro
    50                  55                  60

Arg Ile Glu Ser Thr Lys Ser Lys Ala Lys Val Lys Asn His Pro Phe
65                  70                  75                  80
```

-continued

```
Asp Tyr Gln Ala Leu Ala Glu Ala Phe Ala Lys Asp Gly Ile Ala Cys
                85                  90                  95
Cys Gly Leu Leu Ala Lys Ser Phe Asn Val Glu Glu Arg Asp Ile Ile
            100                 105                 110
Thr Ala Ser Ser His Lys Ala Asp Ile Thr Ile Leu Asp Trp Asp Met
            115                 120                 125
Gln Ser Asp Ser Gly Gln Phe Ala Ile Glu Ile Lys Ser Ile Ile
    130                 135                 140
Val Ser Asp Ile Asn Ser Gly Gly Arg Leu Arg Leu Leu Ser Ile Tyr
145                 150                 155                 160
Thr Gly Glu His Val Thr Ala Val Ile Thr Lys Leu Asn Asn Glu Leu
                165                 170                 175
Lys Lys Thr Tyr Arg Ser Val Ile Lys Asn Asp Ser Ile Phe Ile
            180                 185                 190
Glu Asp Asn Tyr Ala Leu Glu Gln Trp Cys Ile Val Val Ile Ser Lys
            195                 200                 205
Asp Val Tyr Glu Lys Asp Leu Pro Asn Val Leu Ile Lys Lys Phe Thr
    210                 215                 220
Asn Leu Thr Ala Gly Leu Leu Ser Asn Ala Ala Leu Ser Cys Ile Ser
225                 230                 235                 240
Glu Ile Arg Glu Lys Thr His Gly Ile Leu Thr Lys Tyr Asn Asn Lys
                245                 250                 255
Leu Asp Thr Ala Tyr Val Ser His Ile Leu Asn Leu Ile Lys Ser Lys
            260                 265                 270
Glu Ser Arg Ala Tyr Ala Tyr Glu Asn Ala His Asp Tyr Ala Val Asp
        275                 280                 285
Leu Ile Ser Glu Glu Ile Arg Ser Ile Leu Gln Ile Ser Glu Asn Leu
    290                 295                 300
Lys Lys Ser Leu Ser Lys Asn Ser Leu Ser His Trp Pro Ile Phe His
305                 310                 315                 320
Tyr Ala Lys Asn Gly Cys Lys Asn Phe Leu Leu Thr Gly Lys Lys Gln
                325                 330                 335
Lys Asp Leu Ser Val Glu His Leu Arg Asn Ile Leu Ser Ala Asp Ser
            340                 345                 350
Leu Glu Glu Ile Gln His Ala Ile Glu His Ala Ser Leu Gly Lys Lys
        355                 360                 365
Glu Tyr Leu Ser Gln Asp Gly Glu Asp Lys Lys Leu Met Gln Leu
    370                 375                 380
Cys Ser Leu Glu Ile Thr Arg Arg Ser Leu Arg Tyr His Ser His Ile
385                 390                 395                 400
Asp Asn Val Ser Leu Lys Gln Gly Thr Leu Leu Leu Asp Ala Tyr Asn
                405                 410                 415
Phe Val Tyr Leu Cys Ile Gln Pro Leu Cys Asp Ser Val Arg Leu His
            420                 425                 430
Glu Lys Ala Asp Phe Leu Phe Leu Arg Gly Thr Leu Asp Asp Asn Asn
        435                 440                 445
Tyr Asn Leu Leu Ile Glu Asp Glu Tyr Gly Phe Tyr Lys Ile Lys
    450                 455                 460
Met Pro Ala Lys Ala Ser Asn Ile Ile Ser Phe Ser Phe Gly Val Glu
465                 470                 475                 480
Asn Gly Asn Gly Val Ile Ile Gly Lys Lys Asn Asn Leu Val Asn Thr
                485                 490                 495
```

```
Asp Tyr Ile Ser Phe Val Pro Leu Leu Val Glu Lys Ile Ser Thr Pro
            500                 505                 510
Lys Val Leu Lys Trp Ile Gly Glu Ile Lys Thr Thr Tyr Ala Gln Lys
            515                 520                 525
Ile Thr Thr Asp Ile Val Ala Asn Leu Ser Arg Ile Gly Leu Asp Gln
            530                 535                 540
His Glu Trp Leu Arg Ile Lys Ser Lys Asp Ile
545                 550                 555

<210> SEQ ID NO 46
<211> LENGTH: 82
<212> TYPE: PRT
<213> ORGANISM: Escherichia coli

<400> SEQUENCE: 46

Met Ser Ser Arg Gln Ile Leu Glu His Tyr Asn Ala Leu Thr Tyr Pro
1               5                   10                  15
Leu His Gln Ser Ile Leu Leu Gln Ile Met Thr Ser Asn Leu Leu Ser
            20                  25                  30
Val Cys Thr Gly Lys Ser Ile Tyr Glu Asp Ile Ser Gly Ser Ser Trp
        35                  40                  45
Asn Ile Ile His Phe Asn Ile Pro Leu Pro Ile Ser Arg Ala Arg Leu
    50                  55                  60
Ser Ile Phe Ser Tyr Cys Val Arg Ile Lys Pro Trp Met Ser Met Asp
65                  70                  75                  80
Tyr Met

<210> SEQ ID NO 47
<211> LENGTH: 98
<212> TYPE: PRT
<213> ORGANISM: Escherichia coli

<400> SEQUENCE: 47

Met Ser Ile Ile Phe Asn Gly His Tyr Arg Met Lys His Arg Thr Trp
1               5                   10                  15
Ile Thr Glu Ala Leu Arg Leu His Phe Glu His Leu Pro Gln Val
            20                  25                  30
Val Val Gly Arg Arg Leu Gly Val Pro Lys Ser Thr Ala Cys Gly Met
        35                  40                  45
Phe Val Arg Phe Arg Lys Ala Gly Phe Ser Trp Pro Leu Pro Ala Gly
    50                  55                  60
Met Ser Glu Arg Glu Leu Asp Gly Arg Leu Tyr Gly Ser Thr Ser Thr
65                  70                  75                  80
Val Pro Val Val Leu Cys Ser Gly Ser Val Ile Gln Asp Thr Ser Lys
            85                  90                  95
Ser Cys

<210> SEQ ID NO 48
<211> LENGTH: 106
<212> TYPE: PRT
<213> ORGANISM: Escherichia coli

<400> SEQUENCE: 48

Met Ile Lys Thr Arg Arg Thr Lys Arg Thr Phe Ser Pro Glu Phe Lys
1               5                   10                  15
Leu Glu Ala Phe Glu Gln Val Val Lys Tyr Gln Arg Asp Val Arg
            20                  25                  30
```

```
Glu Val Ala Gln Ala Leu Glu Leu Asn Pro Asp His Leu Arg Lys Trp
         35                  40                  45

Ile Arg Leu Tyr Lys Gln Glu Leu Gln Gly Ile Glu Pro Ala Gly Asn
         50                  55                  60

Ala Ile Thr Pro Glu Gln Arg Glu Ile Gln Gln Leu Lys Ala Gln Ile
 65                  70                  75                  80

Lys Arg Val Glu Met Glu Lys Glu Ile Leu Lys Gln Ala Ala Val Leu
                 85                  90                  95

Met Ser Glu Ile Pro Gly Lys Leu Ser Arg
                100                 105
```

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Oligonucleotide

<400> SEQUENCE: 49
tgctctagag ccattactca gaatggg                    27

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Oligonucleotide

<400> SEQUENCE: 50
cgcgagctcg acgactgaat gatccc                     26

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Oligonucleotide

<400> SEQUENCE: 51
tcccccgggt actgcagcac tcaacc                     26

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Oligonucleotide

<400> SEQUENCE: 52
gatcccggga ccactgaaat gcgtgc                     26

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Oligonucleotide

<400> SEQUENCE: 53
tcgtctagag atgatggtga tggagcg                    27

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
gaactgcagc caaatactga taccaccc                                    28

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
gaactgcagg ctaaaacaga agacgcg                                     27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 56
catgcatgca ctccatatga caaccgc                                     27

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 57
tcgtctagaa tgaagctgcg catgagg                                     27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 58
caactgcagt cgcaaattgc gaactgg                                     27

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 59
caactgcaga ccgcaacttt tcgacgc                                     27

```
<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 60
catgcatgcc agtgagccat tgttccc                                   27

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 61
tgctctagat acgactctga caggagg                                   27

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 62
tcagatatca actaccagca gtttgg                                    26

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63
tcagatatcc ataaagagtg acgtggc                                   27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 64
tgctctagaa aacgtggcaa cagagcg                                   27

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 65
tgctctagaa ggcgttgtcg atcctg                                    26
```

```
<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 66
gaactgcagg aaaaggccga gcagactg                              28

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 67
gaactgcagt acagccatgt ttacggt                               27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 68
catgcatgcg gtgtacgaca gtttgcg                               27

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 69
tgctctagac acatcatggg cacacc                                26

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 70
gaactgcaga accgtccaca tcaggcg                               27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 71
gaactgcaga ccctgcttgc cattccg                               27

<210> SEQ ID NO 72
```

-continued

```
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 72
catgcatgca taagcgtcga acaggcg                                              27
```